US008241607B2

(12) United States Patent
Heaney et al.

(10) Patent No.: US 8,241,607 B2
(45) Date of Patent: Aug. 14, 2012

(54) USE OF FRUCTOSE-BASED COMPOUNDS FOR THE DIAGNOSIS OF CANCER

(75) Inventors: Anthony P. Heaney, Los Angeles, CA (US); Hongxiang Hui, Los Angeles, CA (US); Alan Waxman, Manhattan Beach, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 215 days.

(21) Appl. No.: 12/064,496

(22) PCT Filed: Aug. 24, 2006

(86) PCT No.: PCT/US2006/033643
§ 371 (c)(1),
(2), (4) Date: Jan. 29, 2009

(87) PCT Pub. No.: WO2007/025282
PCT Pub. Date: Mar. 1, 2007

(65) Prior Publication Data
US 2009/0175787 A1     Jul. 9, 2009

Related U.S. Application Data

(60) Provisional application No. 60/710,762, filed on Aug. 24, 2005, provisional application No. 60/715,514, filed on Sep. 9, 2005.

(51) Int. Cl.
*A61K 49/00* (2006.01)
(52) U.S. Cl. ...... 424/9.1; 424/1.11; 424/1.65; 424/1.73; 424/1.89
(58) Field of Classification Search .................. 424/1.11, 424/1.65, 1.73, 1.81, 1.85, 1.89, 9.1, 9.3, 424/9.4, 9.5, 9.6, 9.7, 9.8; 206/223, 569, 206/570
See application file for complete search history.

(56) References Cited

U.S. PATENT DOCUMENTS

| 5,093,106 | A | 3/1992 | Dzbanovsky et al. |
| 5,476,842 | A | 12/1995 | Rubin |
| 5,629,412 | A | 5/1997 | Glinskii |
| 5,639,737 | A | 6/1997 | Rubin |
| 5,760,008 | A | 6/1998 | Rubin |
| 5,795,875 | A | 8/1998 | Holme et al. |
| 2006/0051291 | A1 | 3/2006 | Adam et al. |

FOREIGN PATENT DOCUMENTS

| JP | 2002/179574 | | 6/2002 |
| WO | 95/18145 | A1 | 7/1995 |
| WO | 97/32590 | A1 | 9/1997 |
| WO | WO 97/32590 | * | 9/1997 |
| WO | 02/32963 | A1 | 4/2002 |
| WO | 03/086312 | A2 | 10/2003 |
| WO | WO 2004/013347 | | 2/2004 |
| WO | WO 2004/039412 | | 5/2004 |
| WO | 2007/025282 | A3 | 8/2007 |
| WO | 2007/025238 | A3 | 12/2008 |

OTHER PUBLICATIONS

Haradahira et al (Nucl. Med. Biol, 1995, vol. 22, No. 6, pp. 719-725).*
Wang et al (Nuclear Medicine and Biology, May 2005, vol. 32, pp. 367-375).*
Atsumi, T., et al., "High expression of inducible 6-phosphofructo-2-kinase/fructose-2,6-bisphosphatase (iPFK-2; PFKFB3) in human cancers," Cancer Res., 62:5881-87, 2002.
Bantle, J.P., et al., "Effects of dietary fructose on plasma lipids in healthy subjects 1-3," Am. J. Clin. Nutr., 72:1128-1134, 2000.
Bares, R.et al., "F-18 fluorodeoxyglucose PET in vivo evaluation of pancreatic glucose metabolism for detection of pancreatic cancer," Radiology, 192:79-86, 1994.
Brand-Miller, J.C., "Glycemic index in relation to coronary disease," Asia Pac. J. Clin. Nutr., 13:S3, 2004.
Calle, E.E., et al., "Overweight, obesity and cancer: epidemiological evidence and proposed mechanisms," Nat. Rev. Cancer, 4:579-91, 2004.
Chesney, J., et al., "An inducible gene product for 6-phosphofructo-2-kinase with an AU-rich instability element: role in tumor cell glycolysis and the Warburg effect," Proc. Natl. Acad. Sci., USA 96:3047-3052, 1999.
Conti, P.S., et al., "PET and [18F]-FDG in oncology: a clinical update," Nucl. Med. & Biol., 23:717-735,1996.
Darville, M.I., et al., "Complete nucleotide sequence coding for rat liver 6-phosphofructo-2-kinase/fructose-2 ,6-bis phosphatase derived from a cDNA clone," FEBS Letters 224:317-321, 1987.
Di Chiro, G., et al., "Glucose utilization of cerebral gliomas measured by [18F] fluoro-deoxyglucose and posilron emission tomography," Neurology, 32:1323-1329, 1982.
Gatenby, R.A., et al., "Why do cancers have high aerobic glycolysis," Nat. Rev. Cancer, 4(11):891-9, 2004.
Gouyon, F., et al., "Fructose modulates GLUT5 mRNA stability in differentiated Caco-2 cells: Role of cAMP-signalling pathway and PABP (polyadenylated-binding protein)-interacting protein (Paip) 2," J. Biochem., 375:167-174, 2003.
Haradahira, et al. "Radiosynthesis, rodent biodistribution, and metabolism of 1-deoxy-1-[18F]Fluoro-D-Fructose," Nucl. Med. Biol., 22(6):719-725, 1995.
Henry, R.R., et al., "Current issues in fructose metabolism," Ann. Rev. Nutr. 11:21-39, 1991.
Hollenbeck, C.B., "Dietary fructose effects on lipoprotein metabolism and risk for coronary artery disease," Am. J. Clin. Nutr. 58 (suppl) 800S-9S, 1993.

(Continued)

*Primary Examiner* — D L Jones
(74) *Attorney, Agent, or Firm* — Linda B. Huber, Esq.; Nixon Peabody LLP

(57) ABSTRACT

This invention relates to compositions, methods utilizing fructose and other monosaccharides for the diagnosis of cancer. Cancer cells have shown a higher level of fructose utilization as compared to glucose. Further, cancer cells have shown a preferential use of fructose for nucleic acid synthesis. The present invention takes advantage of these features and provides for fructose or fructose-based compositions for the diagnosis of cancer using imaging techniques such as positron emission tomography.

23 Claims, 25 Drawing Sheets

OTHER PUBLICATIONS

Hue, L., et al., "Fructose 2,6-bisphosphate and the control of glycolysis by growth factors, tumor promoters and oncogenes," Adv. Enzyme Regul., 33:97-110, 1993.

Kawaguchi, T., et al., "Regulation of energy metabolism in macrophages during hypoxia. Roles of fructose 2,6-bisphosphate and ribose 1,5-bisphosphate," J. Biol. Chem., 276:28554-61, 2001.

Kim, J., et al., "Multifaceted roles of glycolytic enzymes," Trends Biochem. Sci., 30:142-50, 2005.

Koh, E.T., et al., "Effects of fructose feeding on lipid parameter in obese and lean, diabetic and nondiabetic Zucker rats," J. Nutr., 115:1274-84, 1985.

Liao, et al., "Genetic evidence for a common pathway mediating oxidative stress, inflammatory gene induction, and aortic fatty streak formation in mice," J. Clin. Invest., 94(2):877-884, 1994.

Macheda, M.L., et al., "Molecular and cellular regulation of glucose transporter (GLUT) proteins in cancer," J. Cellular Physiol., 202:654-662, 2005.

McGuinness, O.P., et al. "Effects of fructose on hepatic glucose metabolism," Curr. Opin. Clin. Nutr. Metab. Care, 6:441-8, 2003.

Medina, R.A, et al., "Glucose transporters: Expression, regulation and cancer," Biol. Res., 35(1):9-26,. 2002.

Miatello, et al., "Aortic Smooth Muscle Cell Proliferation and Endothelial Nitric Oxide Synthase Activity in Fructose-fed Rats," Am. J. of Hypertension, 14 (11, Pt. 1), 1135-1141, 2001.

Michaud, D.S., et al., "Dietary sugar, glycemic load, and pancreatic cancer risk in prospective study," J. Natl. Cancer Inst., 94:1293-300, 2002.

Noguchi, Y., et al., "Suppression of facilitative glucose transporter 1 mRNA can suppress tumor growth," Cancer Letters, 154:175-182, 2000.

Okar, D.A., et al., "Fructose-2,6-bisphosphate and control of carbohydrate metabolism in eukaryotes," Biofactors, 10:1-14, 1999.

Pilkis, S.J., et al., "6-Phosphofructo-2-kinase/fructose-2,6-bisphosphatase: a metabolic signaling enzyme," Ann. Rev. Biochem., 64:799-835, 1995.

Rodriguez-Enriquez, S. et al., "Multisite Control of the Crabtree Effect in Ascites Hepatoma Cells," Eur. J. of Bioche.,. 268(8), 2512-2519, 2001.

Rogers, S., et al., "Differential expression of GLUT12 in breast cancer and normal breast tissue," Cancer Letters, 193(2):225-233, 2003.

Silvera, et al., "Glycemic index, glycemic load and pancreatic cancer risk (Canada)," Cancer Causes Control, May 16 (4):431-436, 2005.

Sleder, J., et al., "Hyperinsulinemia in fructose-induced hypertriglyceridemia in the rat, Metabolis.," 29:303-305, 1980.

Smith ,T.A., "Facilitative glucose transporter expression in human cancer tissue," Brit. J. Biomed. Sci., 56(4):285-292, 1999.

Tharanathan, R.N., "Food-derived carbohydrates: structural complexity and functional diversity," Crit. Rev. Biotechnol., 22:65-84, 2002.

Vakkila, et al., "Inflammation and necrosis promote tumour growth," Nat. Rev. Immunol., 4:641-8, 2004.

Walenta, S., et al., "High lactate levels predict likelihood of metastases, tumor recurrence, and restricted patient survival in human cervical cancers," Cancer Res., 60: 916-921,2000.

Walenta, S., et al., "Correlation of high lactate levels in head and neck tumors with incidence of metastasis," Am. J. Pathol., 150:409-415,1997.

Wang, H. et al., "Evaluation of F-18-labeled Amino Acid Derivatives and [18F]FDG as PET Probes in a Brain Tumor-bearing Animal Model," Nuc. Med. and Bio., 32(4), 367-375, 2005.

Watanabe, S., et al., "Polyol content of cerebrospinal fluid in brain-tumor patients," J. of Neurosurg.,70(2), 183-189, Feb. 1989.

Zakim, D., "The effects of fructose on hepatic synthesis of fatty acids," Acta. Med. Scand., 542:5-14, 1972.

Zamora-León, S.P., et al., "Expression of the fructose transporter GLUT5 in human breast cancer," Proc. Natl. Acad. Sci., 93:1847-52, 1996.

Boros et al., Oxythiamine and Dehydroepiandrosterone Inhibit the Nonoxidative Synthesis of Ribose and Tumor Cell Proliferation, Cancer Research, (Oct. 1, 1997), pp. 4242-4248, 57.

Buchholz et al., Concomitant Boron-Neutron Capture Therapy During Fast-Neutron Irradiation of a Rat Glioma, Radiology, (Jun. 1994), pp. 863-867, 191(3).

Gupta et al., Synthesis, Characterization, and Some Immunological Properties of Conjugates Composed of the Detoxified Lipopolysaccharide of Vibrio Cholerae O1 Serotype Inaba Bound to Cholera Toxin, Infection and Immunity, (Aug. 1992), pp. 3201-3208, 60(8).

Yamamoto et al., Properties of the Active Thiamine Transport System in Ehrlich Ascites Tumor Cells, Journal of Biochemistry, (1981), pp. 809-816, 89(3), (Abstract Only).

International Preliminary Report on Patentability issuance date Feb. 26, 2008 for PCT/US2006/033643.

International Search Report and Written Opinion mailed Sep. 26, 2008 for PCT/US2006/033444.

International Preliminary Report on Patentability issuance date Oct. 28, 2008 for PCT/US2006/033444.

European Search Report dated Sep. 16, 2010 for European patent application No. 06824852.5.

Rais B et al Oxythiamine and dehydroepiandrosterone induce a G1 phase cycle arrest in Ehrlich's tumor cells through inhibition of the pentose cycle, Febs letters, Elsevier, Amsterdam, vol. 456, No. 1, Jul. 30, 1999, pp. 113-118.

Glass-Marmor Lea et al., Calmodulin antagonists decrease glucose 1, 6-bisphosphate, fructose 1, 6-bishosphate, ATP and viability of melanoma cells, European Journal of Pharmacology, vol. 313, No. 3, 1996, pp. 265-271.

Cascante M. et al., Role of thiamin (vitamin b-1) and transketolase in tumor cell proliferation, Nutrition and Cancer, London, Jan. 1, 2000, vol. 26, No. 2, pp. 150-154.

Chan K K et al., Inhibition of cell proliferation in human breast tumor cells by antisense oligonucleotides against facilitative glucose transporter 5, Journal of Cellular Biochemistry, Dec. 15, 2004, vol. 93, No. 6, pp. 1134-1142.

Giovannucci Edward et al., Calcium and fructose intake in relation to risk of prostate cancer, Cancer Research, vol. 58, No. 3, Feb. 1, 1998, pp. 442-447.

EP 06824858.2 Extended Search Report dated Apr. 6, 2011.

U.S. Appl. No. 12/064,491 Final Office Action dated Jan. 13, 2012.

U.S. Appl. No. 12/064,491 Non-Final Office Action dated Aug. 5, 2011.

U.S. Appl. No. 12/064,491 Restriction Requirement dated Jan. 6, 2011.

Orkin, S. et al. Report and Recommendations of the Panel to Assess the NIH Investment in Research on Gene Therapy. NIH Home Page (1995).

Stull, R. et al. Antigene, Ribozyme and Aptamer Nucleic Acid Drugs: Progress and Prospects. Pharmaceutical Research. (1995), 12(4):465-483.

* cited by examiner

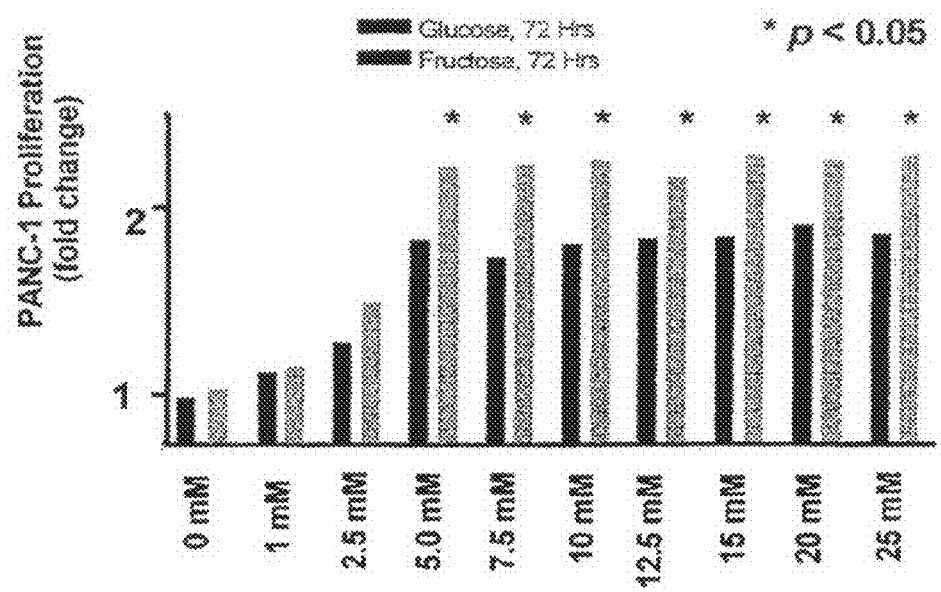

2mM glucose 5.5mM glucose 5.5mM fructose

*, p < 0.01
**, P < 0.001

USE OF FRUCTOSE-BASED COMPOUNDS FOR THE DIAGNOSIS OF CANCER

This application is the National Phase of International Application PCT/US06/33643, filed Aug. 24, 2006, which designated the U.S. and that International Application was published under PCT Article 21(2) in English. This application also includes a claim of priority under 35 U.S.C. §119(e) to U.S. provisional patent application No. 60/715,514, filed Sep. 9, 2005 and U.S. provisional patent application No. 60/710,762, filed Aug. 24, 2005.

GOVERNMENT LICENSE RIGHTS

The U.S. Government has a paid-up license in this invention and the right in limited circumstances to require the patent owner to license others on reasonable terms as provided for by the terms of Grant No. R01CA123273 awarded by the National Institutes of Health.

FIELD OF INVENTION

This invention relates to compositions, methods utilizing fructose and other monosaccharides for the diagnosis of cancer.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

The prevalence of obesity in the United States, and worldwide is increasing. Approximately 35 percent of U.S. adults 20 or older are overweight (i.e., have a body mass index [BMI] of 25 to 29.9), and an additional 30 percent are obese (i.e., have a BMI that is greater than or equal to 30). Among children, an estimated 16 percent of children ages 6-11 are overweight, over twice as many as two decades ago. Among adolescents ages 12-19, the percentage of obesity has more than tripled from 5 to 16 percent. Although extreme obesity has received the most attention in the clinical setting, moderate obesity is more common in the general population. However, even moderate obesity can contribute to chronic metabolic abnormalities characteristic of the insulin resistance syndrome, such as dyslipidemia, hypertension, insulin resistance, and glucose intolerance particularly when it is associated with intra-abdominal fat deposition (i.e. central obesity). Although it is likely that no single factor is responsible for the increased prevalence of moderate obesity, it is likely that environmental elements are interacting with predisposing genetic factors, and identification of the acquired causes contributing to an increase in the prevalence of obesity is key to developing public health policy and dietary and physical activity recommendations. Existing research indicates that weight, physical activity, and nutrition alter cancer risk and carcinogenesis for many cancers, and evidence is accumulating on the effect of these health factors on cancer prognosis and quality of life among cancer survivors. A recent study of a very large prospective cohort of 900,000 U.S. adults estimated that overweight and obesity in the US could account for 14 percent of all deaths from cancer in men and 20 percent of those in women. An International Agency Research on Cancer (IARC) review entitled, "Weight Control and Physical Activity", summarized the evidence across basic and population research, and estimated that between one-quarter and one-third of the cases of many common cancers may be attributable to the combined effect of increased body weight and inadequate physical activity.

The role of dietary changes as contributing factors to the development of obesity are under investigation, and along with an increase in total energy consumption over the past few decades, a clear shift in the types of nutrients consumed in the American diet has been highlighted. Specifically, the consumption of fructose has increased dramatically, primarily because of increased consumption of beverages that are high in fructose and the consumption of other foods such as breakfast cereals, baked goods, condiments, and prepared desserts sweetened with sucrose and high-fructose corn syrup (HFCS). HFCS is produced by the enzymatic isomerization of dextrose to fructose, and most HFCS used in beverages contains about 55% fructose. Its commercial use increased in the 1970s so that by 1985, HFCS accounted for about 35% of the total amount of sweeteners by dry weight in the food supply. Intakes based on the 1977-1978 US Department of Agriculture Nationwide Food Consumption Survey estimated the mean individual consumption of fructose in adolescents and adults was about 40 g/d, the range being 29-54 g/d. Thirteen of the 40 g of dietary fructose was estimated to come from naturally occurring sources of fructose, and 27 g from added sources of fructose. More recent data on fructose consumption in the United States are not available, but food disappearance data, which can serve as an indicator of trends in consumption over time show that although the per capita use of sucrose has decreased moderately from 46.4 kg (102 lb) in 1970 to 30.5 kg (67 lb) in 1997, the per capita use of HFCS has increased from a negligible 0.23 kg (0.5 lb) in 1970 to 28.4 kg (62.4 lb) in 1997. This means that the combined consumption of sucrose, and high fructose corn syrup have increased by 26% from 64 g/day in 1970 to 81 g/day in 1997. This represents an average daily energy intake from added fructose of about 1356 kJ (324 kcal). In fact, just two 355-mL (12-oz) soft drinks can supply up to 50 g/fructose (about 840 kJ, or 200 kcal) or >10% of the daily energy requirements for an average-weight woman, without considering any other dietary sources of fructose. Thus, fructose consumption now makes up a significant proportion of energy intake in the American diet, and this increase in fructose consumption has coincided with the increased prevalence of obesity over the past 2 decades. These observations raise the question as to whether current fructose intakes could contribute to weight gain and its metabolic sequelae, including cancer.

Pancreatic cancer is the fourth leading cause of death in the US (Czito B. Willett C. Clark J. et al: Chemoradiation for unresectable pancreatic cancer. in Cameron J L (ed). Pancreatic Cancer. Hamilton. Ontario. Canada. B C Decker. 2001), 5-year survival is only 5%. Present molecular pathology, and cancer genetic studies indicate that pancreatic adenocarcinoma originates from pancreatic ductal cells, arises via a series of progressive structural stages of neoplastic growth, termed pancreatic intraepithelial neoplasia (PanINs), that are precursors to pancreatic adenocarcinomas, and associated with genetic alterations occurring in a temporal sequence (Bardeesy N, DePinho R A. Pancreatic Cancer Biology, and genetics Nat Rev Cancer 2: 897-909, 2002; Cubila A L, Fitzgerald P J. Morphological lesions associated with human primary invasive nonendocrine pancreas cancer. Cancer Res 36, 2690-9, 1976). The earliest abnormalities include activating KRAS mutations, detectable in ~30% of the earliest PanIN (Kinstra D S, Longnecker D S. K-ras mutations in pancreatic ductal proliferative lesions. Am J pathol 145, 1547-50, 1994; Rozenblum E et al. Tumor-suppressive pathways in pancreatic cancer. Cancer Res 57, 1731-4, 1997), and altered epidermal growth factor (EGF) signaling (both ERBB2 or Her2/neu, and ERBB3) (Korc M et al. Overexpression of the epidermal growth factor receptor in human pancreatic cancer is associated with concomitant increases in the levels of epidermal growth factor and transforming growth factor alpha. J Clin Invest 90, 1352-60 1992; Friess H et al. Pancreatic cancer: the potential clinical relevance of growth factors and their receptors. J Mol Med 74; 35-42 1996; Siblia M et al. The EGF receptor provides an essential survival signal for SOS-dependent skin tumor development. Cell 102, 211-220 2000). In late stage PanINs, inactivation of INK4A (Rozenblum E et al. Tumor-suppressive pathways in pancreatic cancer. Cancer Res 57, 1731-4, 1997), and TP53 (Rozenblum E et al. Tumor-suppressive pathways in pancreatic cancer. Cancer Res 57, 1731-4, 1997) are observed, the former cooperatively accentuating RAS oncogenicity (Chin L et al. Cooperative effects of INK4A, and RAS in melanoma susceptibility in vivo. Genes Dev 11, 2822-2834 1997), and the latter facilitating genetic instability, including telomere dysfunction (Chin L et al. P53 deficiency rescues the adverse effects of telomere loss and cooperates with telomere dysfunction to accelerate carcinogenesis. Cell 97 527-538 1999). Inherited BRCA2 mutations, typically associated with familial breast, and ovarian tumors are found in ~17% of late stage pancreatic cancers in families harboring BRCA2 mutations (Cancer risks in BRCA2 mutation carriers. The breast cancer linkage consortium. J Natl Cancer Inst 91; 1310-1316 1999; Goggins M, Hruban R H, Kern S E. BRCA2 is inactivated in the development of pancreatic intraepithelial neoplasia: evidence and implications. Am J Pathol 156; 1767-1771, 2000), and late PanINs frequently manifest loss of SMAD/DPC4, which encodes a key transcriptional regulator of transforming growth factors-γ family signaling (Hahn S A et al. DPC4, a candidate tumor suppressor gene at human chromosome 19q21.1. Science 271 350-353 1996; Luttges J et al. Allelic loss is often the first hit in the biallelic inactivation of the p53 and DPC4 genes during pancreatic carcinogenesis. Am J Pathol 158 1677-1683 2001).

The only well-established environmental etiologic factor is cigarette smoking, although chronic pancreatitis has been reported to confer a 20-fold excess risk (Lowenfels A B, Maisonneuve P, Cavallini G, et al., Pancreatitic and the risk of pancreatic cancer. N Engl J Med 1993; 328: 1433-7), and evidence points to an association between diabetes mellitus and pancreas cancer, but whether these diseases are due to a common exposure or are causally connected remains unknown (Anderson K E, Potter J D, Mack T M. Pancreatic cancer. In: Schottenfeld D, Fraumeni J Jr, eds. Cancer epidemiology and prevention. New York, N.Y.: Oxford University Press, 1996: 725-71; Everhart J, Wright D. Diabetes mellitus as a risk factor for pancreatic cancer: a meta-analysis. JAMA 1995; 273: 1605-9). Additionally, higher fasting plasma glucose (>140 mg/dl) (Jee S H, Ohrr H, Sull J W, Yun J E, Samet J M. Fasting serum glucose level and cancer risk in Korean men and women. JAMA 2005; 293: 194-202), or postload (Gapstur S M, Gann P H, Lowe W, et al. Abnormal glucose metabolism and pancreatic cancer mortality. JAMA 2000; 283: 2552-8) plasma glucose levels have been associated with increased pancreas cancer mortality. A number of studies have investigated the role of dietary factors in pancreatic cancer risk. As with other epithelial cancers, a diet high in vegetables and fruit—and perhaps specifically high in folate has been associated with a lower risk, though not consistently (World Cancer Research Fund Panel. Food, nutrition, and the prevention of cancer a global perspective. Washington, D.C.: American Institute for Cancer Research, 1997; Nkondjock A, Krewski D, Johnson K C, Ghadirian P, and the Canadian Cancer Registries Epidemiology Research Group. Dietary patterns and risk of pancreatic cancer. Int J Cancer May 1; 114(5):817-823, 2005.). Other studies have identified dietary intake of lycopene or vitamin C as potentially protective factors (Nkondjock A, Ghadirian P, Johnson K C, Krewski D and the Canadian Cancer Registries Epidemiology Research Group. Dietary intake of lycopene is associated with reduced pancreatic cancer risk. J Nutr 135:592-597, 2004; Lin Y, Tamakoska A, Hayakawa T, Narus S, Kitagawa M and Ohno Y. Nutritional factors and risk of pancreatic cancer: A population-based case-control study based on direct interview in Japan. J Gastroenterol. March 40(3):324-325, 2005). Some studies have reported increased pancreatic cancer risk associated with high cholesterol intake (Lin Y, Tamakoska A, Hayakawa T, Narus S, Kitagawa M and Ohno Y. Nutritional factors and risk of pancreatic cancer: A population-based case-control study based on direct interview in Japan. J Gastroenterol. March 40(3):324-325, 2005), and at least six case control studies have reported a positive association between meat intake, and pancreatic cancer risk (Gapstur S M, Gann P H, Lowe W, et al. Abnormal glucose metabolism and pancreatic cancer mortality. JAMA 2000; 283: 2552-8; Howe G R and Burch J D. Nutrition and pancreatic cancer. Cancer Causes Control 7:69-82, 1996). However, in the large prospective 18-year follow-up Nurse Health Study of 121,700 women, no relationship between total fat, fat type, and cholesterol was observed in the 178 women who developed pancreatic cancer (Michaud D S, Giovannucci E, Willett W C, Colditz G A and Fuchs C S. Dietary meat, dairy products, fat and cholesterol and pancreatic cancer risk in a prospective study. J Epidemiol 157(12):1115-1125, 2003).

SUMMARY OF THE INVENTION

The following embodiments and aspects thereof are described and illustrated in conjunction with compositions and methods which are meant to be exemplary and illustrative, not limiting in scope.

The present invention provides for methods and kits for the diagnosis of cancer.

One embodiment of the present invention provides for a method for diagnosing cancer in a mammal, comprising providing a labeled fructose, analog or derivative thereof; administering a detectable quantity of the labeled fructose, analog or derivative thereof to the mammal; and imaging the mammal at least 60 minutes after administering the detectable quantity of the labeled fructose, analog or derivative thereof to the mammal to detect a signal from the label, wherein an abnormal accumulation of the signal from the label indicates a presence of cancer in the mammal.

In one embodiment, the mammal may have intolerance to glucose.

In one embodiment, the labeled fructose, analog or derivative thereof may be capable of being metabolized by the cell or utilized for nucleic acid synthesis.

In one embodiment, the label may be a radiolabel. In one embodiment, the radiolabel may be a radioactive isotope of fluorine, iodine, gallium, technetium, indium or copper. In another embodiment, the radiolabel may be a radioactive isotope of fluorine. In one embodiment, the label may be on the first and/or the second carbon atom of the labeled fructose, analog or derivative thereof. In another embodiment, the labeled fructose analog may be deoxyfructose. In one embodiment, the labeled fructose analog may be deoxyfluorofructose. In another embodiment, the deoxyfluorofructose may be 1-deoxy-1-fluoro-fructose and imaging the mammal may comprise imaging the mammal at least 120 minutes after administering the deoxyfluorofructose to the mammal. In another embodiment, the deoxyfluorofructose may be 1-deoxy-2-fluoro-fructose.

In various embodiments, imaging the mammal may comprise imaging the mammal after an amount of time after administering the detectable quantity of labeled fructose, analog or derivative thereof, wherein the amount of time may be at least 120 minutes, at least 180 minutes, at least 4 hours, at least 24 hours, at least 36 hours, at least 48 hours or combinations thereof. In another embodiment, imaging the mammal may comprise imaging the mammal after the labeled fructose, analog or derivative thereof is utilized by the cell for nucleic acid synthesis.

In another embodiment, imaging the mammal may comprise using a technique selected from the group consisting of positron emission tomography (PET), computed tomography, magnetic resonance imaging, and combinations thereof.

Another embodiment of the present invention provides for a method for diagnosing cancer in a mammal, comprising providing a radioactive fructose, analog or derivative thereof; administering a detectable quantity of the radioactive fructose, analog or derivative thereof to the mammal; and imaging the mammal to detect a radioactive signal, wherein the detection of an abnormal accumulation of radioactivity indicates the presence of cancer in the mammal.

In one embodiment, the radioactive fructose, analog or derivative thereof may be capable of being metabolized by the cell or utilized for nucleic acid synthesis.

In one embodiment, the radioactive fructose, analog or derivative thereof may comprise a radioactive carbon isotope at the first and/or the second carbon atom.

In one embodiment, imaging the mammal may comprise imaging the mammal after the radioactive fructose, analog or derivative thereof is utilized by the cell for nucleic acid synthesis.

In another embodiment, imaging the mammal may comprise using positron emission tomography (PET), computed tomography, magnetic resonance imaging or combinations thereof.

Another embodiment of the present invention provide for a kit for the diagnosis of cancer in a mammal, comprising a composition selected from the group consisting of a labeled fructose, analog or derivative thereof, radioactive fructose, analog or derivative thereof, and combinations thereof; instructions to use the composition for the diagnosis of cancer comprising instructions to administer the composition to the mammal; instructions to image the mammal at least 60 minutes after administering the composition to detect a signal from the label or from the radioactive isotope of fructose, analog or derivative thereof, wherein an abnormal accumulation of the signal indicates the presence of cancer in the mammal.

In one embodiment, the label is a radiolabel. In another embodiment, the radiolabel is a radioactive isotope of fluorine, iodine, gallium, technetium, indium or copper.

In another embodiment, the instructions may further comprise instructions to image the mammal after the composition is utilized by the cell for nucleic acid synthesis.

In another embodiment, the instructions further comprise instructions to use positron emission tomography, computed tomography, magnetic resonance imaging or combinations thereof to image the mammal.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 14 depicts proliferation rates of pancreatic cells in different fructose or glucose concentrations in accordance with an embodiment of the present invention. PANC-1 cells were plated in a range of fructose or glucose concentrations (5-25 mM) for 72 h, after which proliferative rates were measured using an MTS assay. *, p<0.05 for concentrations between 5-25 mM fructose versus glucose.

PANC-1 pancreatic cancer cells and a primary culture of a surgically resected pancreatic tumor were incubated in 2 mM glucose, 5.5 mM glucose or 5.5 mM fructose for 48 h, after which nuclear extracts were incubated with a biotinylated AP-1 probe, and detected by an antibody-linked colorimetric method. *, p<0.01

Figure 25:
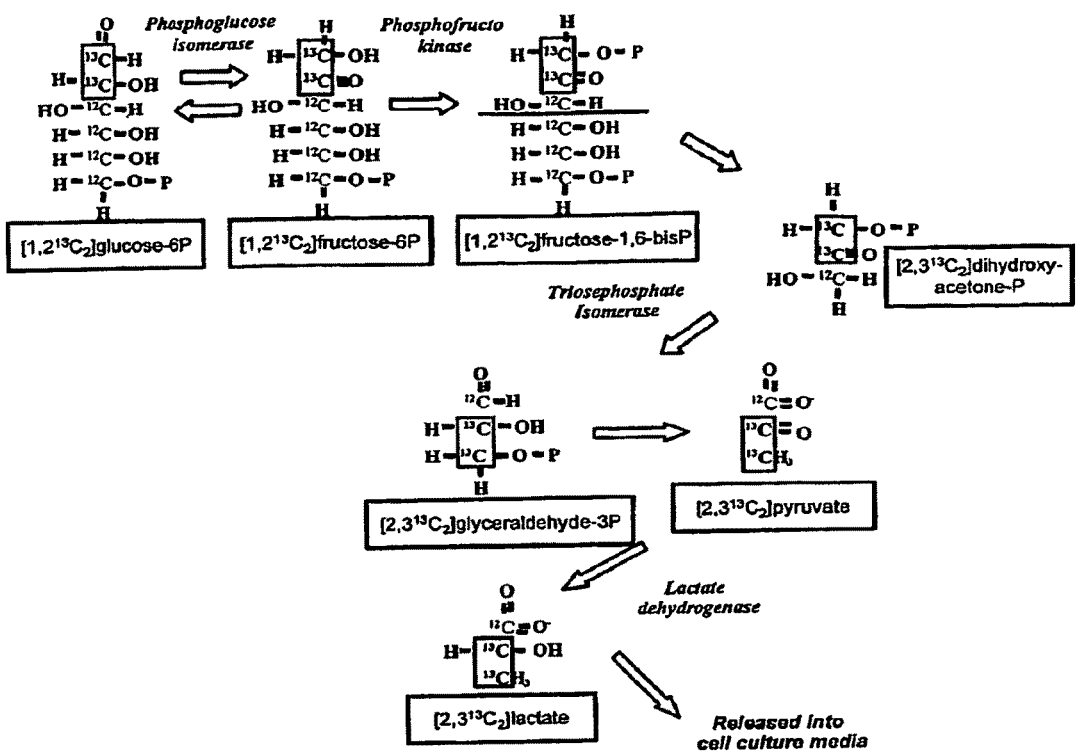

FIG. 25 depicts a schematic representation illustrating how carbohydrate mass isoptomers may be utilized to map their metabolism via glycolysis, in this example to generate energy (ATP), pyruvate, which can enter the tricarboxylic acid cycle, and lactate, which is released into the culture medium in accordance with an embodiment of the present invention.

Figure 26:
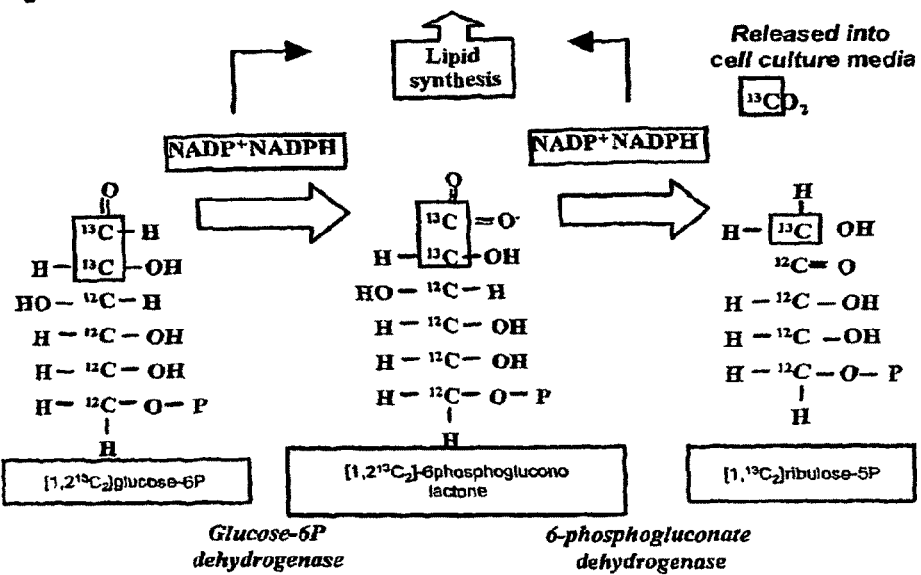

FIG. 26 depicts a schematic representation illustrating carbohydrate metabolism for lipid synthesis, and how carbohydrate mass isoptomers may be utilized to map these pathways in accordance with an embodiment of the present invention.

Figure 27:
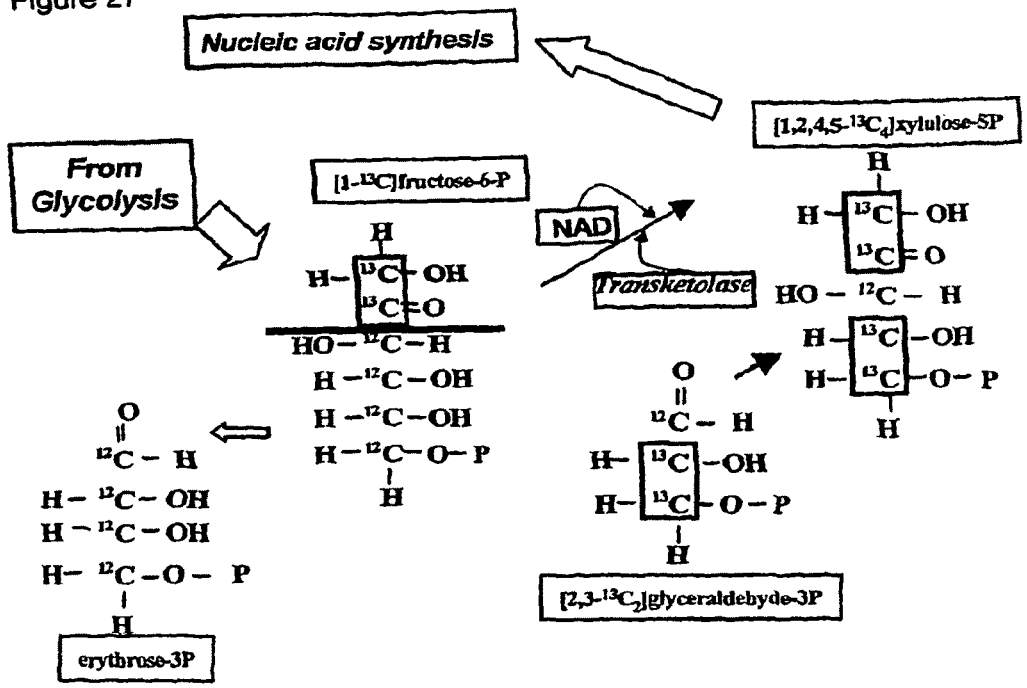

FIG. 27 depicts a schematic representation of the steps via the pentose phosphate pathway, by which carbohydrates can be metabolized to provide sugars for nucleic acid synthesis in accordance with an embodiment of the present invention.

Figure 28:
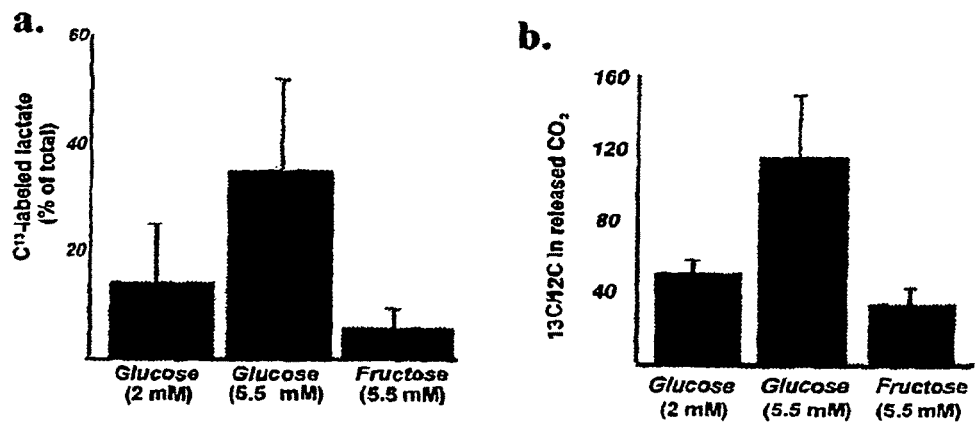

FIG. 28 depicts the metabolism of fructose and glucose in pancreatic cancer cells in accordance with an embodiment of the present invention. Lactate generation from glycolysis (a), and hexose oxidation in the pentose and tricarboxylic acid cycles (b) following treatment of PANC-1 cells with 2 mM glucose, 5.5 mM glucose, and 5.5 mM fructose for 72 h. In (a) the fraction of $^{13}C$-labeled lactate is expressed as the percentage of total lactate measured demonstrating the contribution of each treatment to lactate generation. In (b), the $^{13}C$ to $^{12}C$ ratio in the $CO_2$ released from the PANC-1 cells is presented.

Figure 29:
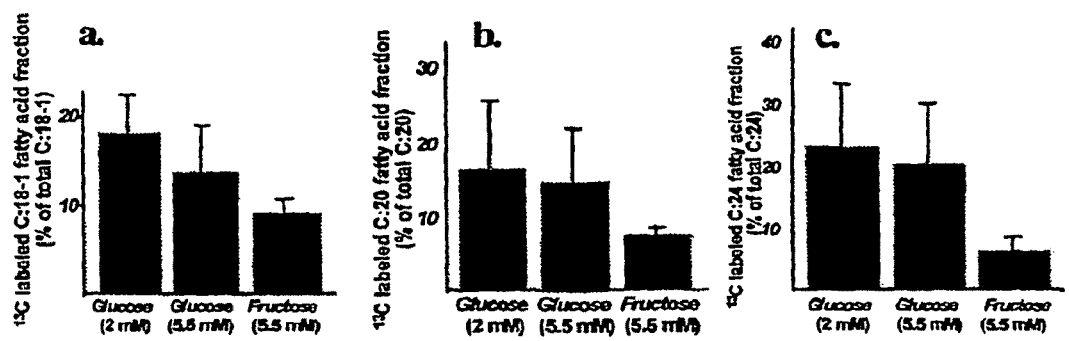

FIG. 29 depicts fatty acid synthesis from glucose versus fructose in accordance with an embodiment of the present invention. Fatty acid synthesis represented by (a), $^{13}C$-labelled oleate, (b) $^{13}C$-labelled arachidic acid, and (c) $^{13}C$-labelled 24-carbon fatty acid fraction following treatment of PANC-1 cells with 2 mM, and 5.5 mM glucose, and 5.5 mM fructose for 72 h. For the fatty acids, the fraction of $^{13}C$-labeled oleate, arachidic acid or 24-carbon fatty acid is expressed as percentage of total oleate, arachidic acid or 24-carbon fatty acids, respectively.

Figure 30:
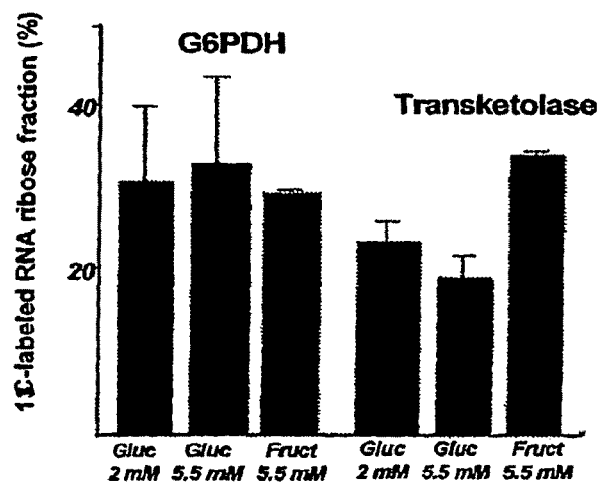

FIG. 30 depicts ribose and deoxyribose synthesis following glucose and fructose treatment in accordance with an embodiment of the present invention. Pentose phosphate shunt activity following treatment of PANC-1 cells with 2 mM glucose, 5.5 mM glucose, and 5.5 mM fructose for 72 h demonstrates that glucose was primarily metabolized via the oxidative pathway (regulated by glucose-6-phosphate dehydrogenase (G6PDH), which shuttles 5-carbon sugars back to the glycolytic pathway, whereas fructose was metabolized via the non-oxidative pathway, which is regulated by the enzyme transketolase (TKK), to synthesize nucleic acids.

Figure 31:
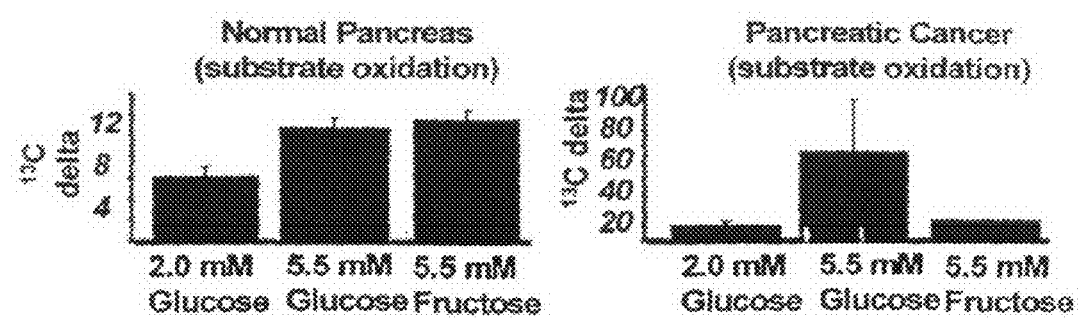

FIG. 31 depicts substrate oxidation in accordance with an embodiment of the present invention. Substrate oxidation in a primary culture of a normal pancreas (left), and a pancreatic cancer (right) following incubation in 2 mM, or 5 mM glucose, or 5 mM fructose for 72 h.

Figure 32:
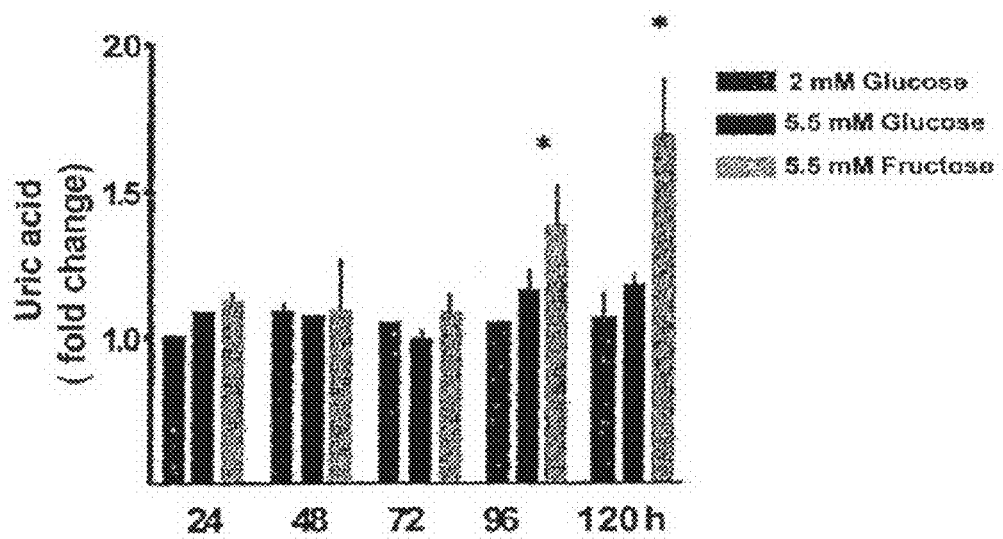

FIG. 32 depicts uric acid production in PANC-1 cells in accordance with an embodiment of the present invention. Uric acid production in pancreatic cancer PANC-1 cells following incubation in 2 mM glucose, 5.5 mM glucose, and 5.5 mM fructose for 24 h, 48, 72, and 96 h respectively, p<0.01 5.5 mM fructose versus 5.5 mM glucose.

Figure 33:
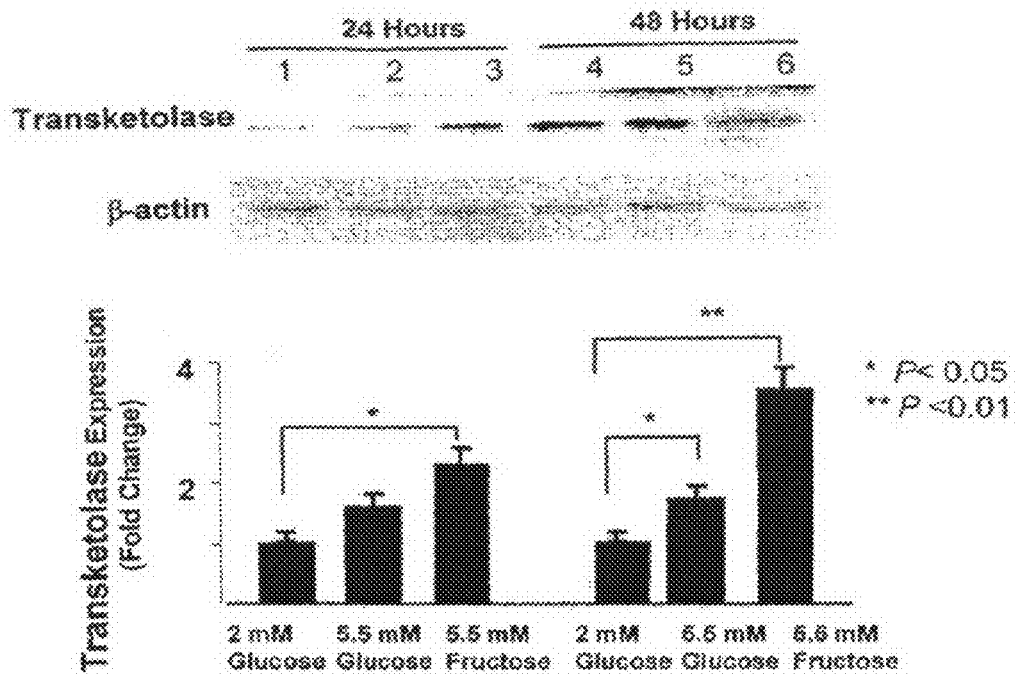

FIG. 33 depicts Western blot analysis of transketolase expression in pancreatic cancer PANC-1 cells following incubation in 2 mM glucose (lanes 1 & 4), 5.5 mM glucose (lanes 2 & 5), and 5.5 mM fructose for 24 h, and 48 h, respectively, in accordance with an embodiment of the present invention. Quantitation of TKK protein levels is depicted in the lower panel.

Figure 34:
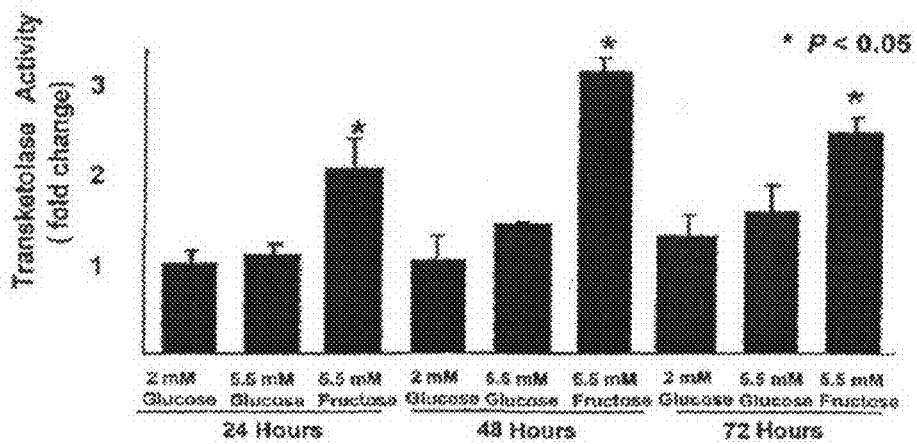

FIG. 34 depicts quantitation of transketolase activity in pancreatic cancer PANC-1 cells following incubation in 2 mM glucose, 5.5 mM glucose, and 5.5 mM fructose for 24 h, 48 h, and 72 h respectively, in accordance with an embodiment of the present invention.

Figure 35:
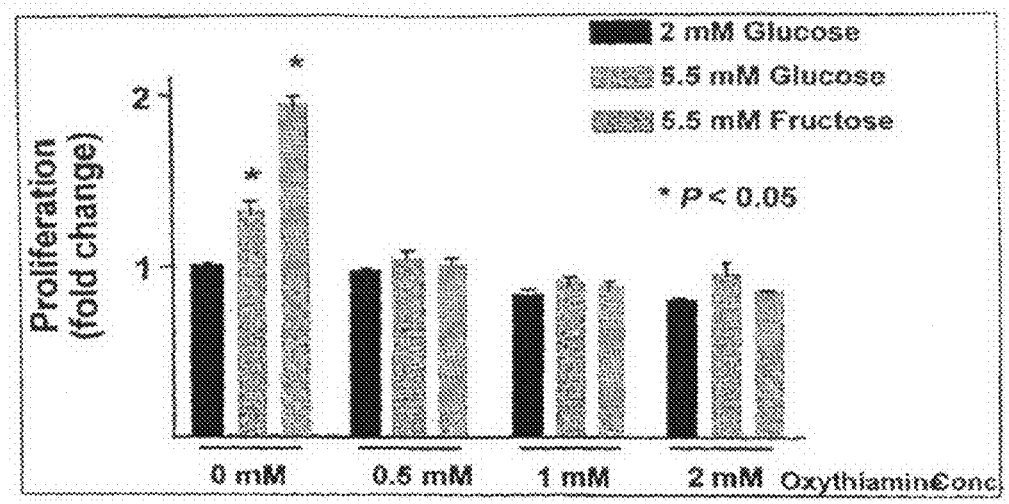

FIG. 35 depicts inhibition of pancreatic cancer PANC-1 cell proliferation by incubation with the transketolase inhibitor, oxythiamine (0.5-2 mM) for 72 h in accordance with an embodiment of the present invention. Proliferative rates were measured using the MTS proliferation assay.

Figure 36:
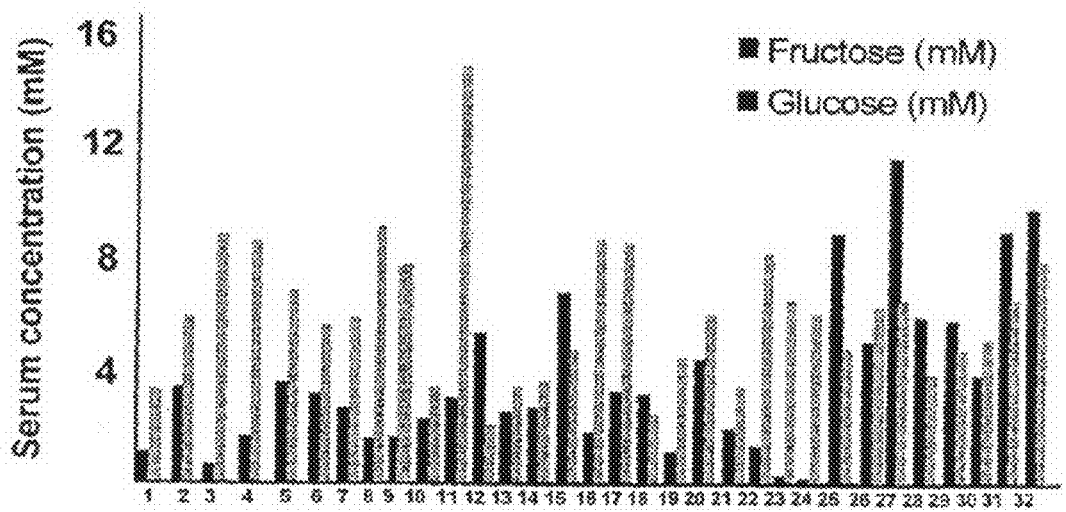

FIG. 36 depicts random serum fructose, and glucose levels in 32 hospital inpatients with unknown diagnosis in accordance with an embodiment of the present invention. Serum fructose was measured using an ELISA based assay as described herein.

Figure 37:
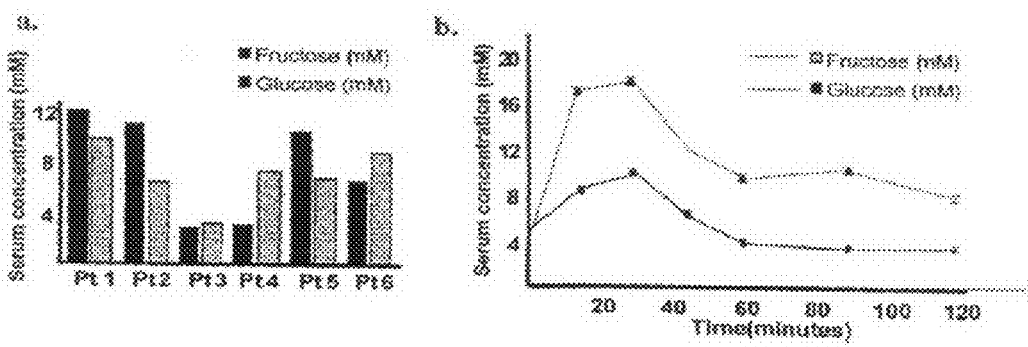

FIG. 37 depicts fasting serum fructose and glucose levels in patients with pancreatic cancer and in normal volunteers in accordance with an embodiment of the present invention. (a) Fasting serum fructose and glucose levels in 6 patients with pancreatic cancer on the morning of resection. (b) Serum fructose, and glucose levels (Mean±SEM) in 3 normal volunteers after a 10 h fast, followed by ingestion of two cans of soda, containing 76 g of carbohydrate in the form of high fructose corn syrup (55% fructose, 45% glucose).

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994); March, *Advanced Organic Chemistry Reactions, Mechanisms and Structure* 4th ed., J. Wiley & Sons (New York, N.Y. 1992); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Abnormal accumulation" refers to an accumulation of the signal (e.g., radioactive signal, including but not limited to gamma rays) that differs from the accumulation that would be expected in healthy, noncancerous tissue or the tissue of a subject without cancer. The accumulation may be higher than the accumulation that may be expected in healthy, noncancerous tissue.

"Cancer" and "cancerous" refer to or describe the physiological condition in mammals that is typically characterized by unregulated cell growth. Examples of cancer include, but are not limited to, colorectal cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, brain cancer, and breast cancer; including, but not limited to, ductal carcinoma, lobular carcinoma, Paget's disease, inflammatory breast cancer, medullary carcinoma, tubular carcinoma, mucinous carcinoma, cribriform carcinoma, papillary carcinoma, and phyllodes tumors.

"Conditions" and "disease conditions," as used herein may include, but are in no way limited to any form of cancer; in particular, pancreatic cancer and breast cancer, including but not limited to ductal carcinoma, lobular carcinoma, Paget's disease, inflammatory breast cancer, medullary carcinoma, tubular carcinoma, mucinous carcinoma, cribriform carcinoma, papillary carcinoma, and phyllodes tumors.

"Fructose-based" as used herein includes compositions and diagnostics which include fructose, its analogs or its derivatives.

"Mammal" as used herein refers to any member of the class Mammalia, including, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Metabolic pathway" as used herein refers to a series of consecutive enzymatic reactions that produce specific products.

"Pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

"Detectable amount" as used herein refers to that amount which is capable of achieving detection by imaging techniques, including for example, positron emission tomography, computed tomography and magnetic resonance imaging. A detectable effective amount can be determined on an individual basis and will be based, at least in part, on consideration of the physiological characteristics of the mammal, the type of delivery system or imaging technique used, the type of label or radioactive label, and/or the time of administration relative to the progression of the disease.

"Tumor," as used herein refers to all neoplastic cell growth and proliferation, whether malignant or benign, and all pre-cancerous and cancerous cells and tissues.

The inventors' data show that fructose induces higher cancer proliferative rates than glucose, and the metabolic studies clearly demonstrate that cancer cells differentially utilize glucose, and fructose, preferentially metabolizing fructose via transketolase for nucleic acid synthesis. The inventors believe that increased cancer proliferation rates due to fructose are not limited to pancreatic cancer or breast cancer. Indeed, fructose induces high proliferation rates in all cancers since fructose may be utilized as an energy source. To place these in vitro observations in the context of human disease, the inventors demonstrated that human circulating fructose concentrations are at levels higher than those which mediate pro-proliferative effects in pancreatic cancer, and that the capacity to control serum fructose levels after a refined fructose load appears inferior to that which controls blood glucose.

Embodiments of the present invention are based on the inventors' discovery as described herein. The present invention includes compositions, methods and kits for the diagnosis of cancer in a mammal, such as a human, utilizing monosaccharide-based approaches.

In various embodiments of the present invention, the monosaccharide may be a pentose and/or a hexose. Examples of pentose monosaccharides include but are not limited to, arabinose, lyxose, ribose, ribulose, xylose, and xylulose. Examples of hexose monosaccharides include but are not limited to, allose, altrose, fructose, galactose, gulose, idose, mannose, psicose, sorbose, tagatose, and talose. In particular embodiments, the monosaccharide may be fructose.

In other embodiments of the present invention, the monosaccharide may be a ketose. Examples of ketoses include but are not limited to erythrulose, ribulose, xylulose, fructose, psicose, sorbose, and tagatose. In one embodiment, the ketose is fructose.

It is believed that all cancers may be diagnosed in accordance with various embodiments of the present invention. In one embodiment of the present invention, the cancer may be breast cancer. In another embodiment, the cancer may be pancreatic cancer.

The inventors believe that fructose-based compositions in which fructose is preferentially used by cancer cells, is effective in targeting the cancer cells for diagnosis, wherein it may provide a view of the cancer cells and/or their metabolic pathways when used in conjunction with imaging techniques.

Embodiments of the present invention include methods for diagnostic studies of cancer cells. In one embodiment of the present invention thus may be accomplished by administering a fructose-based composition to a mammal and studying the metabolism of the fructose-based composition.

In various embodiments of the present invention, methods are provided for diagnostic imaging of cancer cells.

One embodiment of the present invention may be accomplished by positron emission tomography (PET) utilizing a monosaccharide based radiopharmaceutical. It is known that fluorodeoxyglucose is an acceptable radiopharmaceutical used for PET scans to detect cancer. Based on the preferential use and uptake of fructose by cancer cells, fructose may be similarly modified to produce a fructose-based radiopharmaceutical which produces a superior image during a PET scan. In one particular embodiment, the radiopharmaceutical may be fructose-based and/or fructose analog-based. The radioactive label and/or isotope of the radiopharmaceutical may be any acceptable radioactive label and/or isotope and will be readily apparent to those skilled in the art. The radioactive label and/or isotope may be any atom that may be conjugated to fructose, its analog or its derivative. Examples include but are not limited to radioactive isotopes of fluorine, iodine, gallium, technetium, indium or copper. Additional radioactive isotopes will be readily recognized by those skilled in the art. In one embodiment, radioactive label and/or isotope may be fluorine. In one embodiment, the radioactive isotope may be $^{18}$-fluorine ($^{18}F$). In another embodiment, the radioactive isotope may be $^{19}$-fluorine ($^{19}F$). In various embodiments, the radioactive label and/or isotope may be linked to any of the carbon atoms of the monosaccharide, for example in fructose, the radioactive label and/or isotope can be linked to one or more of the six carbon atoms. In one embodiment, the radioactive label and/or isotope may be linked to the first carbon atom. In another embodiment, the radioactive label and/or isotope may be linked to the second carbon atom. In other embodiments, the radioactive label and/or isotope may be linked to the third, fourth, fifth and/or sixth atom(s). A fluorine-labeled fructose molecule may be made by any appropriate technique, as will be readily appreciated by those of skill in the art. See e.g., U.S. Publication No. 2006/0051291 and Haradahira et al. "Radiosynthesis, Rodent Biodistribution, and metabolism of 1-Deoxy-1-[$^{18}$F]Fluoro-D-Fructose," *Nucl. Med. Biol.* 22(6):719-725 (1995), herein incorporated by reference and though fully set forth in their entirety.

In one embodiment deoxy-fructose may be used. This analog of fructose may be utilized by the cell in the glycolitic pathway of fructose metabolism. Further, this analog may be utilized in nucleic acid synthesis in the cell. While Haradahira et al. have used 1-deoxy-1-[$^{18}$F]fluoro-D-fructose, to determine its potential as a metabolic trapping tracer, they were unable to show any feature of a metabolic trapping tracer. While not wishing to be bound by any particular theory, the inventors believe that Haradahira et al. did not allow sufficient time for the uptake of 1-deoxy-[$^{18}$F]fluoro-D-fructose, which may have resulted in the 1-deoxy-1-[$^{18}$F]fluoro-D-fructose not being incorporated into nucleic acids synthesized by the cells. The present invention allows for sufficient time prior to imaging studies. The amount of time after administering the fructose or fructose-based compositions for an imaging study will depend on a variety of factors, such as the type of fructose-based compound, and whether the detection is for the initial uptake or for nucleic acid synthesis utilizing the fructose or fructose-based compounds. While additional time may be advantageous in conjunction with the use of 1-deoxy-1-[$^{18}$F]fluoro-D-fructose, additional time prior to imaging studies using other fructose-based compounds may not be necessary.

In another embodiment, the diagnostic is based on the use of a fructose-based composition that is capable of being metabolized and utilized for nucleic acid synthesis. The radioactive moiety of the fructose-based or fructose-analog based radiopharmaceutical may be incorporated into the cell's nucleic acid (e.g., DNA, RNA). The portion of the radiopharmaceutical that is not utilized for nucleic acid synthesis may leave the cell. Thus, after an appropriate amount of time, the target to background ratio of the cancerous cells versus normal cells may be increased and the detection of cancerous cells may be made. Additionally, due to the preferential use of fructose by cancerous cells, the target to background ratio may be increase and the detection of cancerous cells may be made.

The PET scan may be performed by a standard methodology that generally involves the following steps: (1) administering a fructose-based and/or a fructose analog-based radiopharmaceutical to a mammal, such as a human; (2) positioning the mammal in a PET scanner; (3) having the scanner detect and record the radioactive rays, such as gamma rays, and create an image map of the area and/or areas where the radiopharmaceutical is located and/or used.

In one embodiment, the detection of the radioactive rays may be performed after a period of time after administering the fructose-based and/or fructose analog-based radiopharmaceutical to the mammal. In one embodiment, detection may be performed after 60 minutes. In another embodiment, detection may be performed after 120 minutes. In another embodiment, detection may be performed after 180 minutes. In other embodiments, detection may be performed after 6 hours, 12 hours or 18 hours. In another embodiment, detection may be performed after 24 hours, 36 hours, 48 hours or longer. In various embodiments, the detection may be performed several days after the administration of the fructose-based or fructose analog-based radiopharmaceutical to the mammal; for example, detection may be made after about 5-7 days. In various embodiments, the detection may be done serially; for example, an initial image is taken after 2 hours and another image is taken after 24 hours. One skilled in the art will be able to determine the timing may be appropriate for the detection of cancer. Factors that may determine the appropriate timing for the detection may be based on the type of radiopharmaceutical used. For example, the half-life of the isotope may be a factor for the imaging studies. Another factor may be the desirability to achieve a high target to background ratio. For example, the target to background ratio may depend on the isotope and basis of the detection (e.g., initial uptake or nucleic acid synthesis). One skilled in the art will also be able to determine the frequency that may be appropriate for the detection of cancer. For example, one may wish to obtain an initial image after 3 hours and an additional image after the radioisotope has been incorporated in the cells' DNA, which may be after 24 hours, 36 hours, 48 hours, or more. Fructose stays in circulation for a longer period of time as compared to glucose and allows for more time for the accumulation of fructose in cells and cancer cells. Furthermore, fructose is preferentially used to synthesize nucleic acids and thus a longer period of time may be advantageous prior to detection of the radioactive isotopes into nucleic acids.

In another embodiment, fructose or its analog or derivative may comprise radioactive isotopes of carbon, oxygen and/or hydrogen. In one embodiment, the first carbon may be a radioactive isotope. In another embodiment, the second carbon may be a radioactive isotope. In other embodiments, the third, fourth, fifth, and/or sixth carbon may be the radioactive isotope. In various embodiments, carbon isotopes may be, for example, $^{11}$C or $^{13}$C. In another embodiment, $^{15}$O may be used. One skilled in the art will recognize additional appropriate carbon isotopes as well as oxygen and hydrogen isotopes.

Further embodiments of the present invention include computed tomography—positron emission tomography fusion studies (CT-PET). Still further embodiments of the present invention includes magnetic resonance imaging—positron emission tomography fusion studies (MR-PET). CT-PET fusion studies may be accomplished by simultaneous imaging using CT and PET and utilizing a computer and computer programs to generate an image and location of the cancer cells. MR-PET fusion studies may be accomplished by simultaneous imaging of using MR and PET and utilizing a computer and computer programs to generate an image and location of the cancer cells.

The fructose-based compositions and/or therapies may be administered by any appropriate technique, as will be readily appreciated by those of skill in the art. By way of example and not to be interpreted as limiting, the composition and/or therapy may be administered via oral administration or intravenous administration.

Additional embodiments of the present invention relate to diagnostic studies of metabolic pathways related to cancer cells. Examples of metabolic pathways include, but are not limited to, monosaccharide metabolism such as glucose metabolism and fructose metabolism; and glycolysis. Other embodiments include models for the studies of metabolic pathways related to cancer.

Another embodiment of the present invention provide for diagnosing cancer in patients who have a level of intolerance to glucose; for example, diabetic individuals or insulin deficient individuals. Currently, the use of fluorodeoxyglucose (FDG) in PET imaging may be problematic to these individuals because their glucose and/or insulin levels may require close monitoring to prevent any adverse effects from the administered fluorodeoxyglucose. Short term increases of fructose do not affect insulin resistance. Thus, these individuals may benefit from a fructose-based diagnostic method, although the use of the present invention is not limited to this patient population.

In various embodiments, the present invention provides pharmaceutical compositions including a pharmaceutically acceptable excipient along with a therapeutically effective amount of fructose or fructose based composition described herein. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in an image detectable quantity. The precise image detectable quantity is that quantity of the composition that will yield the most effective results in terms of efficacy of diagnosis in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of composition), the nature of the pharmaceutically acceptable carrier or carriers in the formulation, and the route of administration. One skilled in the clinical and pharmacological arts will be able to determine an image detectable quantity through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

The present invention is also directed to kits to diagnose cancer. The kit is an assemblage of materials or components, including at least one of the inventive compositions. Thus, in some embodiments the kit contains a composition including fructose or a fructose-based composition as described herein.

The exact nature of the components configured in the inventive kit depends on its intended purpose. For example, some embodiments are configured for the purpose of diagnosing cancer. In one embodiment, the kit is configured particularly for the purpose of diagnosing mammalian subjects. In another embodiment, the kit is configured particularly for the purpose of diagnosing human subjects. In further embodiments, the kit is configured for veterinary applications, diagnosing subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to diagnose cancer in a mammal. Instructions may comprise, for example, instructions to administer the composition to the mammal; instructions to image the mammal at least 60 minutes after administering the composition to detect a signal from the label or from a radioactive isotope of fructose, analog or derivative thereof, wherein an accumulation of the signal indicates the presence of cancer in the mammal; Instructions to image the mammal after the composition is utilized by the cell for nucleic acid synthesis; and/or instructions to use positron emission tomography, computed tomography, magnetic resonance imaging or combinations thereof.

Optionally, the kit also contains other useful components, such as, diluents, buffers, pharmaceutically acceptable carriers, syringes, catheters, applicators, pipetting or measuring tools, or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit are those customarily utilized in diagnosing cancer and/or containing radioactive compositions. As used herein, the term "package" refers to a suitable solid matrix or material such as glass, plastic, paper, foil, and the like, capable of holding the individual kit components. Thus, for example, a package can be a glass vial used to contain suitable quantities of the fructose or the fructose-based compositions as described herein. The packaging material generally has an external label which indicates the contents and/or purpose of the kit and/or its components.

Refined Carbohydrates, Fructose and Cancer

Insulin Resistance and Insulin-Mediated Growth Promoting Actions

High carbohydrate intake has been hypothesized to be a risk factor for breast cancer, possibly mediated by elevated levels of free insulin, estrogen and insulin-like growth factor-1. This hypothesis is supported by population-based case-control studies. In a Mexican population characterized by relatively high fat and high carbohydrate intakes, carbohydrate intake was positively associated with breast cancer risk, and among carbohydrate components, the strongest associations were observed for sucrose and fructose (Romieu I, Lazcano-Ponce E, Sanchez-Zamorano L M, Willett W, Hernandez-Avila M. Carbohydrates and the risk of breast cancer among Mexican women. Cancer Epidemiol Biomarkers Prev 13:1283-9, 2004).

In humans, epidemiological studies support an association between fructose-intake specifically, and cancer risk. Food-frequency questionnaires, documenting CHO intake, glycemic load, in addition to sucrose, and fructose intake, collected from a cohort of US women (n=88,802) participating in the Nurse Health Study, revealed a 53% increased risk of pancreatic cancer development in women who had a high glycemic intake, and particularly in the cohort who reported a high fructose-intake (57% increased risk) (Michaud D S, Liu S, Giovannucci E, Willett W C, Colditz G A, Fuchs C. Dietary sugar, glycemic load, and pancreatic cancer risk in prospective study. J Natl Cancer Inst. 94: 1293-300, 2002).

Fructose intake stimulates lipogenesis in animals, and although data in humans is less conclusive, several studies have demonstrated significant increases in lipid parameters on fructose versus glucose diets (Silvera et al., Glycemic index, glycemic load and pancreatic cancer risk (Canada). Cancer Causes Control May 16(4):431-436, 2005; Brand-Miller J C. Glycemic index in relation to coronary disease. Asia Pac J Clin Nutr 13: S3, 2004; Laio et al., Genetic evidence for a common pathway mediating oxidative stress, inflammatory gene induction, and aortic fatty streak formation in mice. J Clin Invest 94(2): 877-884, 1994; Vakkila et al., Inflammation and necrosis promote tumour growth. Nat Rev Immunol. 4: 641-8, 2004; Calle et al., Overweight, obesity and cancer: epidemiological evidence and proposed mechanisms. Nat Rev Cancer 4: 579-91, 2004).

Carbohydrate Metabolism

Dietary carbohydrate from which humans gain energy enters the body in complex forms, such as disaccharides and the polymers starch (amylose and amylopectin) and glycogen. The first step in the metabolism of digestible carbohydrate is the conversion of the higher polymers to simpler, soluble forms that can be transported across the intestinal wall and delivered to the tissues. The breakdown of polymeric sugars begins in the mouth by the enzyme lingual amylase. Once the food has arrived in the stomach, acid hydrolysis contributes to its degradation. In the small intestine the main polymeric-carbohydrate digesting enzyme is pancreas-derived α-amylase, which has similar activity to salivary amylase, producing disaccharides and trisaccharides. The latter are converted to monosaccharides by intestinal saccharidases, including maltases that hydrolyze di- and trisaccharides, and the more specific disaccharidases, sucrase, lactase, and trehalase. The net result is the almost complete conversion of digestible carbohydrate to its constituent monosaccharides. The resultant simple carbohydrates such as glucose, and fructose are transported across the intestinal wall to the hepatic portal vein and then to liver parenchymal cells and other tissues for oxidation in a process known as glycolysis.

Glucose and fructose are the two most important simple sugars for human consumption. They have the same molecular formula, $C_6H_{12}O_6$, but have different structures. The sugars differ in the bond environment of the oxygen atom in the sugar, but each is a carbohydrate comprising 6 water molecules and 6 carbon dioxide molecules with the yield of 6 oxygen molecules. They are classified differently as hydrocarbon derivatives, glucose being classified as an aldehyde and fructose as a ketone, but are otherwise structurally identical. Although both glucose and fructose metabolism is similar in many respects, there are important differences that the inventors believe may be important in cancer growth. Transport of glucose or fructose across the cell membrane is the first rate-limiting step for sugar metabolism and is facilitated by glucose/fructose transport (GLUT) proteins, twelve (GLUT1-12) of which have been identified (Bantle et al., Effects of dietary fructose on plasma lipids in healthy subjects 1-3. Am J Clin Nutr 72: 1128-1134, 2000). Once in the cell, glucose is oxidized to either lactate or pyruvate, and under aerobic conditions, the dominant product in most tissues is pyruvate. In cancer cells, high glycolytic flux is required for rapid tumor growth, and glucose uptake, and lactic acid levels correlate with tumor progression, invasiveness, patient morbidity, and mortality (Henry et al., Current issues in fructose metabolism. Ann Rev Nutr 11: 21-39, 1991; Hollenbeck C B. Dietary fructose effects on lipoprotein metabolism and risk for coronary artery disease. Am J Clin Nutr 58 (suppl) 800S-9S, 1993; Tharanathan R N. Food-derived carbohydrates: structural complexity and functional diversity. Crit Rev Biotechnol. 22:65-84, 2002; Kim et al., Multifaceted roles of glycolytic enzymes Trends Biochem Sci. 30:142-50, 2005; Medina R A and Owen. Glucose transporters: Expression, regulation and cancer. Biol Res 35(1):9-26, 2002; Gatenby R A, Gillies R J. Why do cancers have high aerobic glycolysis Nat Rev Cancer, 4(11):891-9, 2004.). Additionally, cancer cells maintain an abnormally high glycolytic rate even in the presence of oxygen, a phenomena first described by Otto Warburg (Warburg effect) (Eigenbrodt E. Glycolysis: one of the keys to cancer? Trends Pharmacol Sci 1: 240-245, 1980; Hennipman et al., Glycolytic enzyme activities in breast cancer metastases. Tumour Biol 9: 241-248, 1988; Warburg et al, On the metabolism of cancer cells. Biochem Z 152: 319-344, 1924; Bares et al., F-18 fluorodeoxyglucose PET in vivo evaluation of pancreatic glucose metabolism for detection of pancreatic cancer. Radiology, 192: 79-86, 1994). High glycolytic flux is required for rapid tumor growth, and glucose uptake, and lactic acid levels accurately predict tumor progression, invasiveness, metastatic tendency, and overall patient morbidity, and mortality (Bares, R., Klever, P., Hau-Plmann, S., Hellwig, D., Fass, J., Crerius, U., Schurnpelick, V., Mittemtayer, C., and Bull, U. F-18 fluorodeoxyglucose PET in vivo evaluation of pancreatic glucose metabolism for detection of pancreatic cancer. Radiology, 192: 79-86, 1994; Conti, P. S., Lilien, D. L., Hawley, K., Keppler, J., Grafton, S. T., and Bading, J. R. PET am [18F]-FDG in oncology: a clinical update. Nucl. Moo. Biol., 23: 717-735, 1996; Walenta, S., Wetterling, M., Lehrice, M., Schwicken, G., Sundfor, K., Rofstad, E. K., and Mueller-Klieser, W. High lactate levels in head and neck cancers predict likelihood of metastases, tumor recurrence, and restricted patient survival in human cervical cancers. Cancer Res., 60: 916-921, 2000; Walenta, S., Salameh, A., Lyng, H., Evensen, J. F., Mitze, M., Rofslad, E. K., and Mueller-Klieser, W. Correlation of high lactate levels in head and neck tumors with incidence of metastasis. Am. J. Pathol., 150: 409-415, 1997; Di Chiro, G., DeLaPaz, R. L., Brooks, R. A., Sokoloff, L., Komblith, P. L., Smith, B. H., Patronas, N. J., Kufta, C. V., Kessler, R. M., Johnston, G. S. Manning, R. G., and Wolf, A. P. Glucose utilization of cerebral gliomas measured by [18F] fluorodeoxyglucose and positron emission tomography. Neurology, 32: 1323-1329, 1982; Noguchi, Y., Saito, A., Miyagi, Y., Yamanaka, S., Macat, D., Doi, C., Yoshikawa, T., Tsuburaya, A., Ito, T., and Satoh, S. Suppression of facilitative glucose transporter 1 mRNA can suppress tumor growth. Cancer Lett., 154: 175-182, 2000).

Fructose Metabolism

Figure 1:
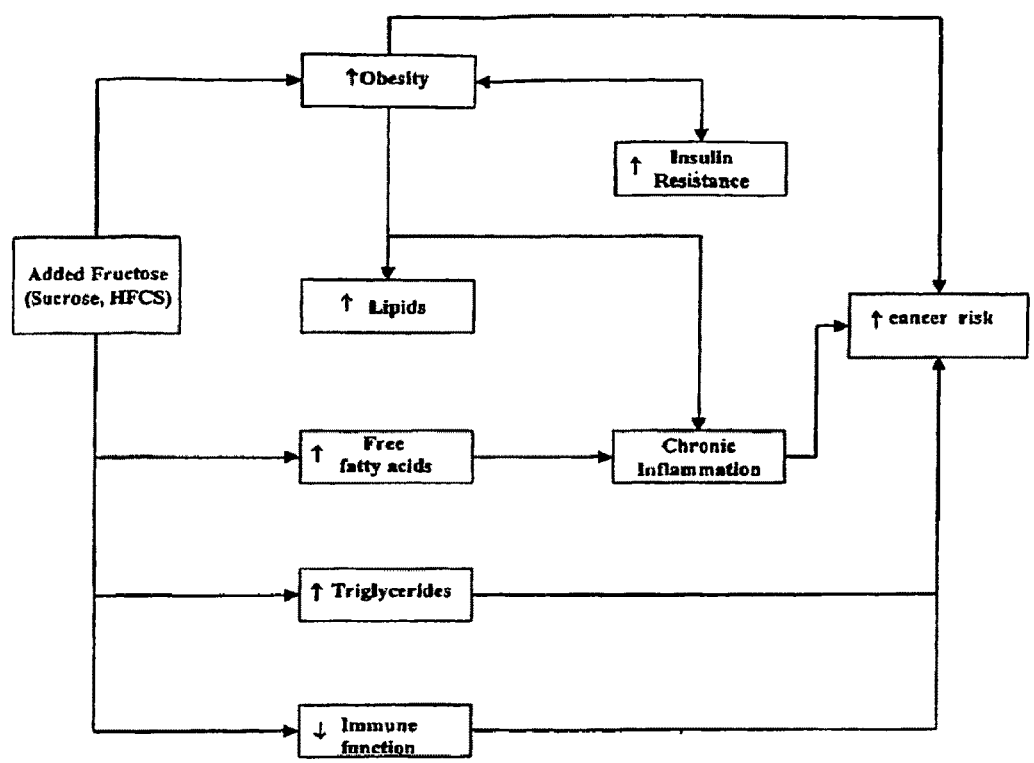
FIG. 1 depicts a summary of potential mechanisms linking increased refined fructose consumption and cancer in accordance with an embodiment of the present invention.
Figure 2:
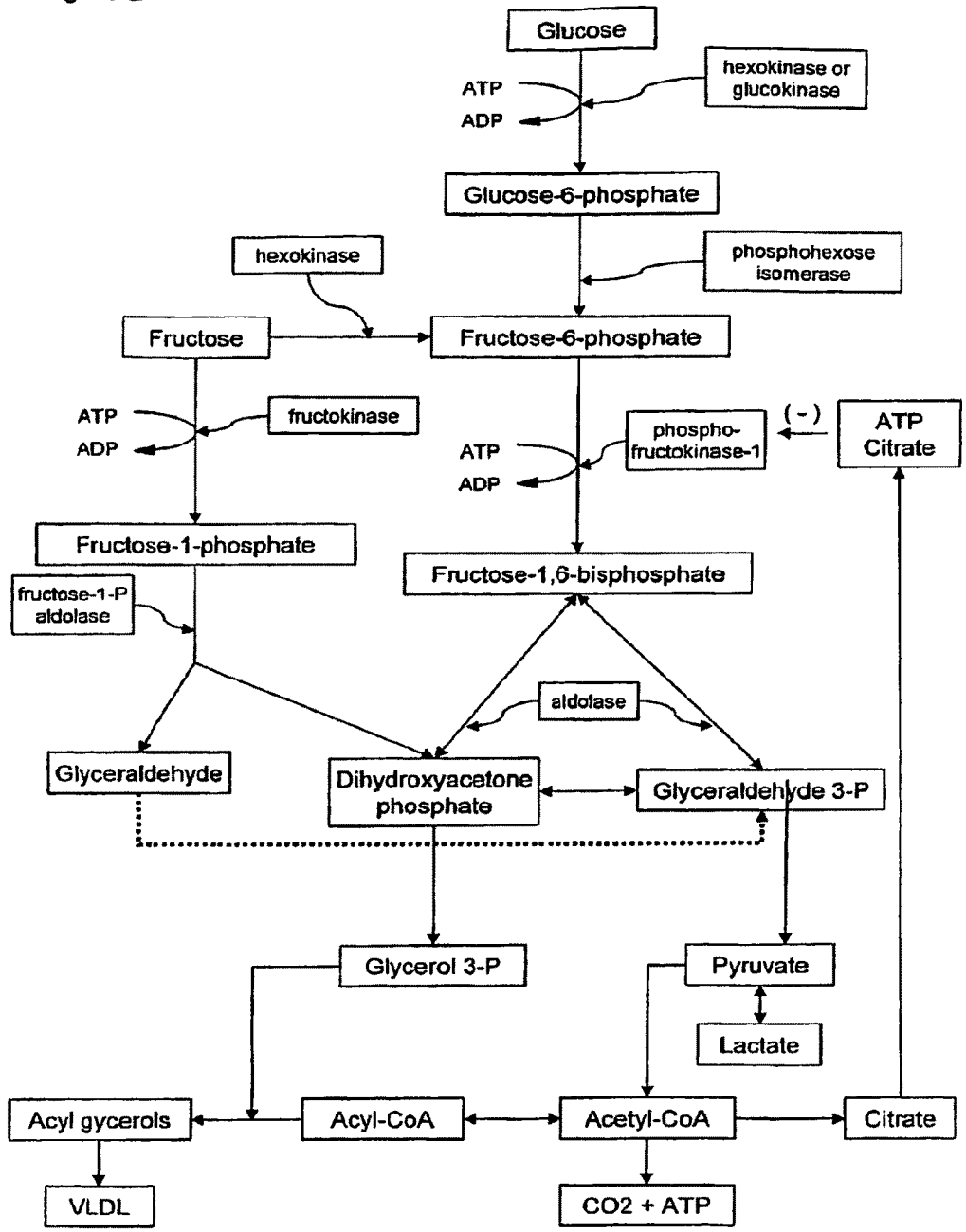
FIG. 2 depicts a schematic of carbohydrate metabolism in accordance with an embodiment of the present invention. Glucose-derived carbon may enter the glycolytic pathway in to generate pyruvate or lactate, a process limited by feedback inhibition of citrate and ATP on the rate limiting enzyme phosphofructokinase. Fructose can also enter glycolysis via hexokinase to form fructose-6-phosphate or can also be metabolized by fructokinase, thereby allowing fructose derived carbon to enter the glycolytic pathway at the triose-phosphate level (left side of panel) (dihydroxyacetone phosphate and glyceraldheyde-3-phosphate). Thus, fructose may bypass the rate limiting phosphofructokinase control point, and can serve as an unregulated source of both glycerol-3-phosphate and acetyl CoA for hepatic lipogenesis.

Diets containing large amounts of fructose or sucrose (a disaccharide of glucose and fructose) can utilize the fructose as a major source of energy. Like glucose, fructose is taken into the cell by 3 fructose-selective GLUTs 2, and 5, and 7. (Bantle et al., Effects of dietary fructose on plasma lipids in healthy subjects 1-3. *Am J Clin Nutr* 72: 1128-1134, 2000; Conti et al., PET am [18F]-FDG in oncology: a clinical update. *Nucl. Moo. Biol.,* 23: 717-735, 1996; Walenta et al., High lactate levels in head and neck cancers predict likelihood of metastases, tumor recurrence, and restricted patient survival in human cervical cancers. *Cancer Res.,* 60: 916-921, 2000). Fructose can enter the metabolic pathway in two ways, depending on which tissue is involved (muscle or liver). As most tissues contains only the enzyme hexokinase, fructose is phosphorylated at the sixth carbon atom, competing with glucose for the hexokinase involved (FIG. 2). However, fructose may also be phosphorylated on the first carbon atom in a reaction catalyzed by the specific fructokinase-1, to generate fructose 1-phosphate (FIG. 2). Generally speaking, appreciable quantities of fructose are metabolized by this route only in the intestines and the liver, but some studies have postulated that cancer cells may possess fructokinase-1 activity (McGuinness O P, Chemington A D. Effects of fructose on hepatic glucose metabolism. Curr Opin Clin Nutr Metab Care. 6: 441-8, 2003), and in the data the inventors demonstrate that breast cancer cells express fructokinase-1 mRNA. Fructose-1-phosphate can then be split into dihydroxyacetone phosphate and glyceraldehydes (FIG. 2). The glyceraldehyde is next phosphorylated, and then along with dihydroxyacetone phosphate enters the latter steps of the Embden-Meyerhof pathway. The significance of this is that fructose can enter the glycolytic pathway distal to the glycolysis rate limiting enzyme phosphofructokinase-1 to facilitate hepatic triacylglycerol production, and therefore unlike glucose, fructose can serve as a relatively unregulated source of acetyl-CoA. Alternatively, fructose-1-phosphate may also be phosphorylated to form fructose-1,6-diphosphate, and transit the glycolytic pathway in a similar manner to glucose.

Figure 3:
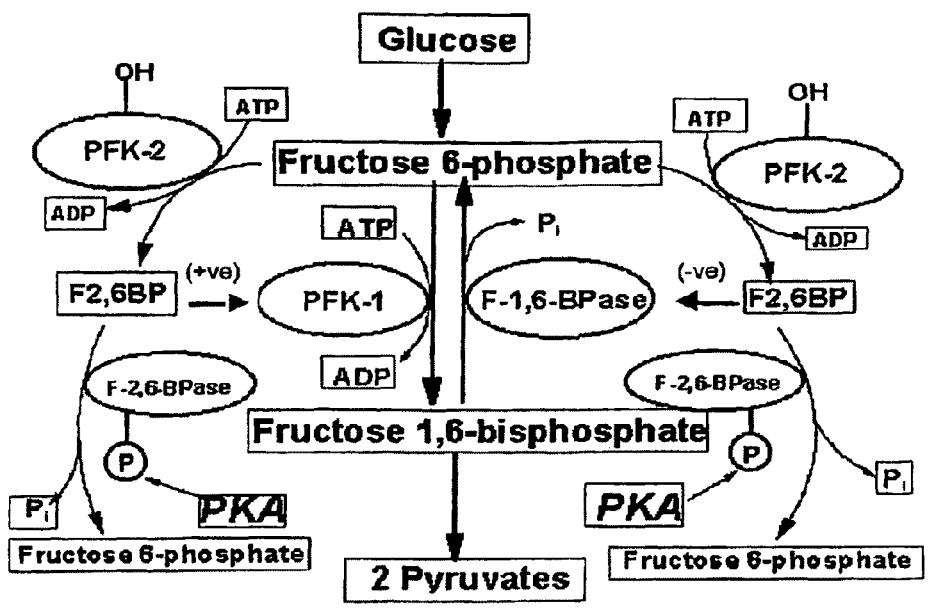
FIG. 3 depicts the regulation of glycolysis and gluconeogenesis by fructose 2, 6-bisphosphate (F2, 6BP) in accordance with an embodiment of the present invention. The major sites for regulation of glycolysis and gluconeogenesis are the phosphofructokinase-1 (PFK-1) and fructose-1, 6-bisphosphatase (F-1, 6-BPase) catalyzed reactions. PFK-2 is the kinase activity and F-2, 6-BPase is the phosphatase activity of the bi-functional regulatory enzyme, phosphofructokinase-2/fructose-2, 6-bisphosphatase that generates/dephosphorylates 2, 6 BP, the potent positive regulator of glycolysis. Protein kinase A (PKA) is a cAMP-dependent protein kinase which phosphorylates PFK-2/F-2, 6-BPase turning on the phosphatase activity. (+ve) and (−ve) refer to positive and negative activities, respectively.

While not wishing to be bound by any particular theory, it is believed that the glycolytic reactions (FIG. 2) catalyzed by hexokinase, and PFK-1 proceed with a relatively large free energy decrease. Although, these enzymes are allostearically controlled to regulate the flux through glycolysis, the rate limiting step in glycolysis is the reaction catalyzed by PFK-1 (McGuinness O P, Chemington A D. Effects of fructose on hepatic glucose metabolism. Curr Opin Clin Nutr Metab Care. 6: 441-8, 2003). PFK-1 is a tetrameric enzyme, and ATP is both a substrate and an allostearic inhibitor of PFK-1. Relatively recently, fructose 2,6-bisphosphate, F2, 6BP, which is not an intermediate in glycolysis or in gluconeogenesis was identified as the most potent activator of glycolysis (Kawaguchi T, Veech R L, Uyeda K Regulation of energy metabolism in macrophages during hypoxia. Roles of fructose 2,6-bisphosphate and ribose 1,5-bisphosphate J Biol. Chem. 276:28554-61, 2001; Hue L, Rousseau G G Fructose 2,6-bisphosphate and the control of glycolysis by growth factors, tumor promoters and oncogenes Adv Enzyme Regul. 33:97-110, 1993; Okar D A, Lange A J. Fructose-2,6-bisphosphate and control of carbohydrate metabolism in eukaryotes. Biofactors. 10:1-14, 1999; Pilkis S J, Claus T H, Kurland I J, Lange A J. 6-Phosphofructo-2-kinase/fructose-2,6-bisphosphatase: a metabolic signaling enzyme Annu Rev Biochem. 64:799-835, 1995). This substrate exerts considerable control over the rate of glucose utilization by allostearically activating phosphofructo-1-kinase (PFK-1), and inhibiting the gluconeogenic enzyme fructose 1,6 bisphosphatase (F1,6 BPase-1) (FIG. 3). Synthesis, and breakdown of fructose 2,6 bisphosphate (Fru-2, 6-BP) is catalyzed by the bifunctional enzyme 6-phosphofructo-2-kinase/fructose 2,6 bisphosphatase (PFK-2/F 2,6 BPase) (FIG. 3). Four different genes coding different isoenzymes (PFKFB1-4) have been identified, and differ not only in their tissue distribution but also in their kinetic, and regulatory properties (Manzano A, Perez J X, Nadal M, Estivill X, Lange A, and Bartrons R. Cloning, expression and chromosomal localization of a human testis 6-phospho-fructo-2-kinase/fructose-2,6-biophosphatase.
Gene (Amst.), 229: 83-90, 1999; Heine-Suner D, Diaz-Guillen M A, Lange A G, and Rodriguez de Corcoba S. Sequence and structure of the human 6-phosphofructo-2-kinase/fructose-2,6-biophosphatase heart isoform gene (PFKFB2). Eur J Biochem, 254: 103-110, 1998; Lange A G and Pilkis S G. Sequence of human liver 6-phosphofructo-2-kinase/fructose, 2,6-biophosphatase. Nucleic Acids Res 18: 3652, 1990). Of the four PFK-2 isoenzymes, only inducible PFK (iPFK/PFKFB-3) lacks a critical serine phosphorylation site that is required for the down-regulation of kinase activity (Sakakibara R, Kato M, Okamura N, Nakagawa T, Komada Y, Tominaga N, Shimojo M, and Fukusawa M. Characterization of a human placental fructose-6-phosphate, 2-kinase/fructose-2,6-biophosphatase. J Biochem (Tokyo) 122: 122-128, 1997). Consequently, PFKFB-3 has the highest kinase:phosphatase activity ratio, and thus maintains highly elevated F-2, 6-BP levels, which in turn sustains high glycolytic rates. Significantly, iPFK/PFKFB-3 is constitutively expressed in several human cancer cell lines having high proliferative rates that require the activity of the enzyme for the synthesis of 5-ribosyl-1-pyrophosphate, a precursor for purine, and pyrimidines (Atsumi T, Chesney J, Metz C, Leng L, Donnelly S, Makita Z, Mitchell R, Bucala R. High expression of inducible 6-phosphofructo-2-kinase/fructose-2,6-bisphosphatase (iPFK-1; PFKFB3) in human cancers. Cancer Res 62: 5881-87, 2002; Chesney J, Mitchell R, Benigni F, bacher M, Spiegel L, Al-Abed Y, Ham J H, Metz C, Bucala R. An inducible gene product for 6-phosphofructo-2-kinase with an AU-rich instability element: role in tumor cell glycolysis and the Warburg effect. Proc Natl Acad Sci, USA 96: 3047-3052, 1999). Indeed, the activity of this enzyme has been proposed as part of the explanation for the Warburg effect, where high glycolytic rates are observed in transformed cells even in the presence of oxygen (Darville M I. Crepin K M, Vandekerckhove J, Van-Damme J, Octave I N, Rider M H, March and M J, Hue L, and Rousseau G G. Complete nucleotide sequence coding for rat liver 6-phosphofructo-2-kinase/fructose-2,6-bis phosphatase derived from a cDNA clone. FEBS Lett 224: 317-321, 1987). As noted, rapidly proliferating transformed cells constitutively express iPFK-2 (PFKFB-3) mRNA and protein in vitro, and inhibition of iPFK-2 expression decreases tumor growth in experimental animal models (Peez J X, Roig T, Manzano A, Dalmau M, Boada J, Ventura F, Rosa J L, Bermudez J, Bartrons R. Overexpression of fructose 2, 6 bisphosphatase decreases glycolysis and delays cell cycle progression. Am J Physiol Cell Physiol 279: C1359-65, 2000). In addition, iPFK-2 (PFKFB-3) is induced by hypoxia, and the iPFK-2 (PFKFB-3) promoter has response elements to several transcription factors including myc, and NfkappaB (Norris J L and Baldwin A S Jr. Oncogenic ras enhances NF-κB transcriptional activity through Raf-dependent and Raf-independent mitogen-activated protein kinase signaling pathways. J Biol Chem 274: 13841-13846, 1999; Minchenko A, Leschinsky I, Opentanova I, Sang N, Srinivas V, Armstead V and Caro J. Hypoxia-inducible factor-1-mediated expression of the 6-phosphofructo-2-kinase/fructose-2,6-bisphosphatase-3 (PFKFB3) gene. Its possible role in the Warburg effect. J Biol Chem 277: 6183-6187, 2002).

In T47-D breast cancer cells, progestin treatment led to increased PFK-2 expression, and increased the number of cells in S-phase (Hamilton J A, Callaghan M J, Sutherland R L, and Watts, C K. Identification of PRG1, a novel progestin-responsive gene with sequence homology to 6-phosphofructo-2-kinase/fructose, 2,6-biophosphatase. Mol Endocrinol 11: 490-502, 1997). In summary, fructose conversion to fructose 2,6 bisphosphate by the isoforms of PFK-2 acts to speed transit of fructose, and glucose through the glycolytic pathway to increase energy availability for cell proliferation. While not wishing to be bound by any particular theory, the inventors believe that the increased fructose-induced breast cancer proliferative rates are due to increased inducible PFK-2 (iPFK-2/PFKFB-3) levels generating fructose-2,6-bisphophate that in turn potently stimulates phosphofructo-1-kinase, thereby transiting both glucose and fructose faster through the glycolytic pathway to generate increased energy for cell proliferation. The data demonstrate that MCF-7 breast cancer cells express fructokinase-1 (FK-1). This enzyme potentially enables breast cancer cells to metabolize fructose directly to fructose-1-phosphate (FIG. 2), to enter the glycolytic pathway distal to the glycolysis rate limiting enzyme phosphofructokinase-1, and to generate higher ATP levels for cell proliferation. Therefore, unlike glucose, fructose can serve as a relatively unregulated source of acetyl-CoA.

Additionally, the data demonstrate pancreatic cancer FK-1, and fructose-1-P-aldolase mRNA expression, and increased GLUT-5 mRNA levels following fructose-treatment.

While not wishing to be bound to any particular theory, it is believed that the form in which fructose is ingested, is extremely important. Clearly, fruit, and vegetables contain fructose, but this is mixed with significant quantities of fiber, which limits fructose absorption rates, and contains antioxidant vitamins, particularly vitamins C and A, and additional components that provide anticancer benefits. While not wishing to be bound by any particular theory, the inventors believe that it is dietary sources of refined fructose that are the real risk, in the form of fructose corn syrup. The inventors also believed that the increased proliferative actions of fructose are not restricted to breast cancers with disrupted EGFR-signaling.

While not wishing to be bound by any particular theory, the inventors also believed that refined fructose is an independent risk factor for in vivo breast cancer development and progression. The effects of fructose in vivo may be multifactorial and include effects due to increased insulin resistance, effects due to an enhanced inflammatory state, and effects due to associated obesity.

In vitro data demonstrated that breast cancer cells proliferate more rapidly in medium containing fructose than glucose, and express fructo-kinase-1 (FK-1), a glycolytic enzyme that is usually only found in significant amounts in normal hepatic and intestinal cells. While not wishing to be bound by any particular theory, it is believed that aberrant breast cancer FK-1 expression and increased expression of a second key glycolytic enzyme, inducible phospho-fructokinase-2 (iPFK-2/PFKFB-3) underlie the increased fructose-mediated proliferation the inventors have observed. Fructo-kinase-1 expression allows breast cancer cells to metabolize fructose to fructose-1-phosphate, thereby bypassing key rate limiting steps that regulate glucose metabolism. The second enzyme, iPFK-2/PFKFB-3 generates fructose 2, 6 bisphosphate (F 2,6 BP), which is a potent inducer of phosphofructokinase-1 activity, the rate-limiting enzyme of glycolysis.

The inventors' demonstration (FIG. 10) that fructose may be able to self-regulate its own transporter, GLUT-5, support the rationale to use SiRNA approaches to silence GLUT-5 expression or transiently over express GLUT-5 in the breast cancer cells, and examine proliferative rates in fructose-related breast cancer cells. The inventors have demonstrated that breast cancer cells express significant levels of fructose kinase-1 (FK-1), and fructose-1-P aldolase (FPA), two enzymes that potentially enable cancer cells to metabolize fructose by additional glycolytic pathways to glucose, and emphasizing the importance of the proposed study of the metabolic pathways utilized by fructose, and glucose respectively. Further, Western blot analysis using phospho-specific antibodies to pMEK, p90RSK, and pCREB levels in protein lysates harvested from MCF-7, and MDA-MB231 cells cultured in fructose, and glucose for 24 h indicate that the MAPK pathway is involved in fructose-mediated increased breast cancer proliferative rates (FIG. 11), and support the examination of transcriptional activation in fructose-, and glucose-treated MCF-7, and MDA-MB231 cells, transiently transfected with CRE-luciferase, AP-1-luciferase, and SRE-luciferase reporter constructs.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Breast Cancer Cells Exhibit Increased In Vitro Proliferative Rates in Fructose Versus Glucose Standard media for breast cancer cell culture contain either 5-7 mM (low) and 12-25 mM (high) glucose concentrations. Estrogen receptor (ER) positive MCF-7, and ER negative MDA-MB231 cells were cultured overnight in 2 mM glucose standard DMEM medium containing 10% fetal bovine serum prior to incubation for periods between 8, and 72 hours in standard DMEM medium containing 10% fetal bovine serum, and 5 mM glucose or 5 mM fructose.

Figure 4:
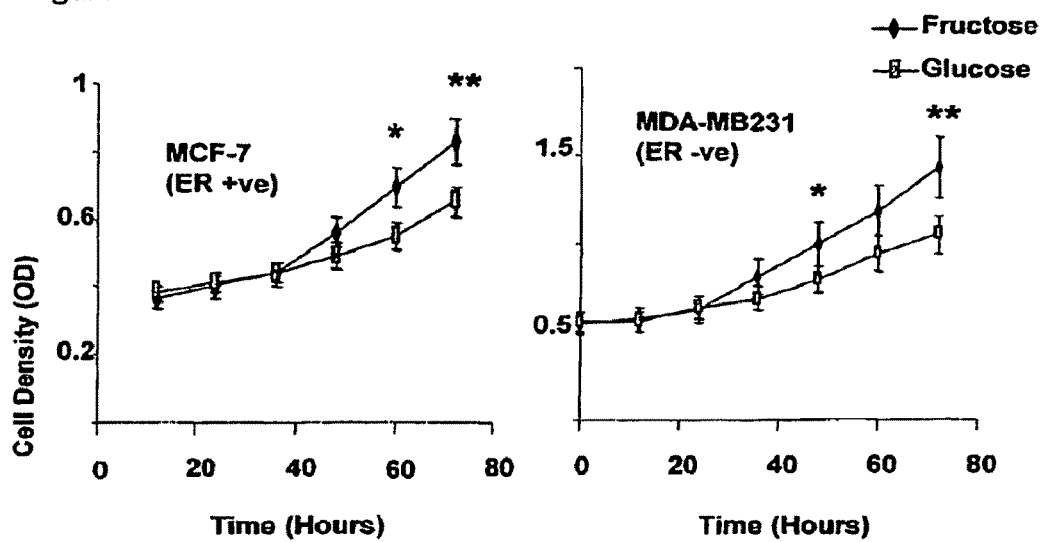
FIG. 4 shows that breast cancer cells proliferate more rapidly in fructose (5 mM) than glucose (5 mM) containing medium in accordance with an embodiment of the present invention. Estrogen receptor (ER) positive MCF-7, and ER negative MDA-MB231 cells were plated in 5 mM fructose or glucose for times between 8-72 h, and proliferative rates measured using MTT assay. *, $p<0.05$; **, $p<0.01$.
Figure 5:
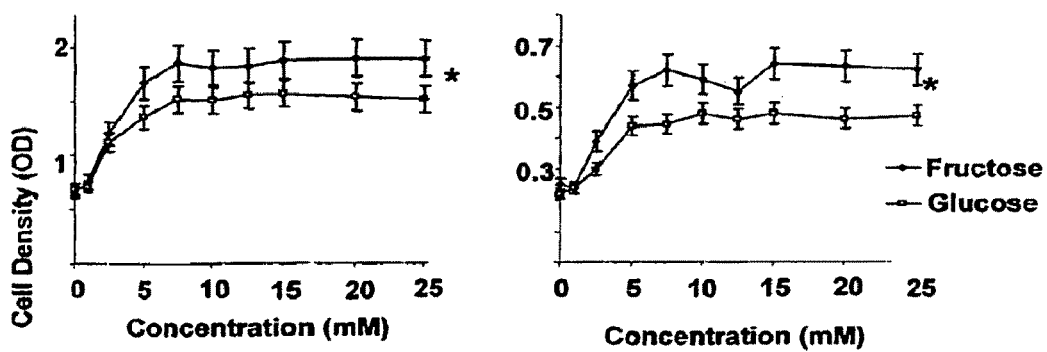
FIG. 5 depicts fructose-mediated increased breast cancer proliferation in accordance with an embodiment of the present invention. ER positive MCF-7, and ER negative MDA-MB231 cells were plated in a range of fructose or glucose concentrations (5-25 mM) for 72 h, after which proliferative rates were measured using an MTT assay. *, $p<0.05$ for concentrations between 5-25 mM fructose versus glucose.
Figure 6:
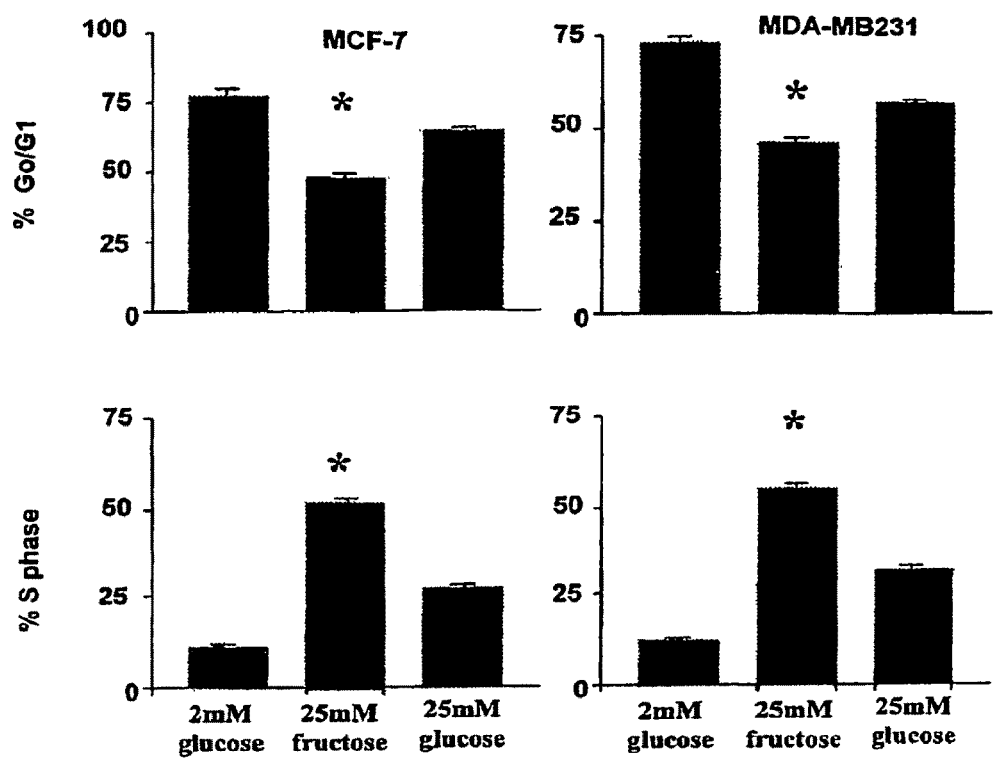
FIG. 6 depicts cell cycle profiles in accordance with an embodiment of the present invention. FACS analysis of MCF-7, and MDA-MB231 breast cancer cells after culture in 2 mM glucose, 25 mM glucose, and 25 mM fructose, depicting percentage of cells in G0/G1, and S-phase. *, $p<0.01$.

Proliferative rates were then measured in replicate (minimum of 6) aliquot wells of the breast cancer cells grown in glucose, or fructose containing medium. As depicted in FIG. 4, both ER negative MDA-MB231, and ER positive MCF-7 breast cancer cells exhibited higher proliferative rates in 5 mM fructose, compared to cells grown in 5 mM glucose, but otherwise identical conditions. In separate experiments, proliferative rates of the MCF-7, and MDA-MB231 breast cancer cells were compared following culture in a range of fructose, and glucose concentrations (2-25 mM) for 72 hours. As depicted in FIG. 5, the fructose-mediated increased breast cancer proliferation was observed over a range of concentrations of fructose, and as depicted in FIG. 5, cells grown for 72 hours in 5 mM fructose exhibited higher proliferative rates to cells grown in 5-fold higher glucose concentrations (25 mM).

Example 2

Breast Cancer Cells Express Fructokinase-1 mRNA

Figure 7:
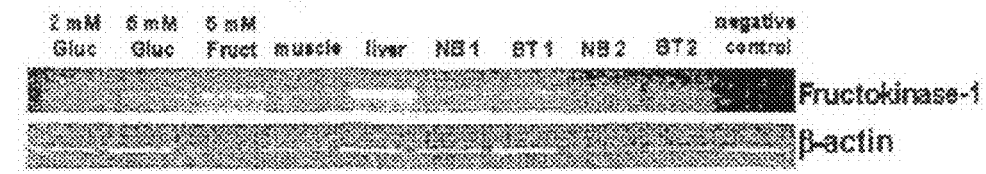
FIG. 7 depicts fructokinase-1 expression in accordance with an embodiment of the present invention. Breast cancer cells (MCF-7) express Fructokinase-1 (FK-1). RT-PCR was used to measure fructokinase-1 (FK-1) mRNA levels in MCF-7 cells following growth in 2 mM glucose, 5.5 mM glucose, or 5.5 mM fructose for 24 h, and in two human breast cancers (BT 1 & 2), and matched adjacent normal breast tissue (NB 1 & 2) from the same individual. Low level fructokinase was seen in human muscle. Human liver, and exclusion of template served as positive and negative controls.

While not wishing to be bound by any particular theory, it is believed that the increased breast cancer proliferative rates are due to increased expression of several key glycolytic enzymes, including fructokinase-1, and inducible phosphofructokinase (iPFK-2/PFKFB-3) levels. The inventors used RT-PCR analysis and specific primer pairs (SEQ ID NO: 1 (3'cctgccagatgtgtctgcta), SEQ ID NO: 2 (5'aagtgcttggccacatcttt)) to examine fructokinase-1 (FK-1) mRNA levels in glucose- or fructose-treated breast cancer cells. As depicted in FIG. 7, MCF-7 cells cultured in 2 mM glucose exhibited minimal FK-1 mRNA expression, slightly higher levels were seen in cells grown in 5 mM glucose, but highest FK-1 levels were seen in breast cancer cells grown in 5 mM fructose. As expected human hepatic tissue exhibited high, and muscle low FK-1mRNA expression. Also examined were FK-1 mRNA levels in two surgically resected human breast cancers, and paired adjacent normal breast tissue from the same individual. FK-1 mRNA was detectable in both normal and tumor tissue.

Example 3

Breast Cancer Cells Express Fructokinase-1 and Fructose-1-P Aldolase mRNA

Figure 8:
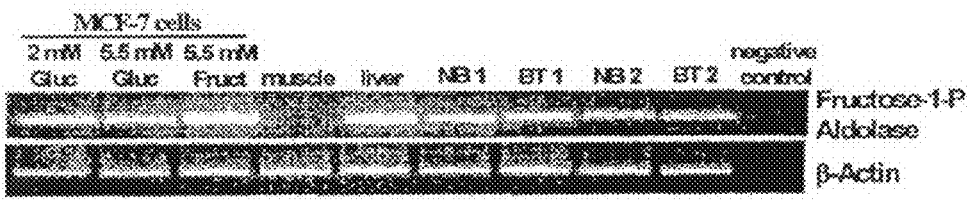
FIG. 8 depicts fructose-1-P aldolase expression in accordance with an embodiment of the present invention. Breast cancer cells (MCF-7) express the β-isoform of fructose 1-P-aldolase (FPA). RT-PCR was used to measure FPA mRNA levels in MCF-7 cells following growth in 2 mM glucose, 5.5 mM glucose, or 5.5 mM fructose for 24 h, and in two human breast cancers (BT 1 & 2), and matched adjacent normal breast tissue (NB 1 & 2) from the same individual. As expected the FPA β-isoform was present in human liver, and negative in human muscle tissue. Primer exclusion served as an additional negative control.

FK-1 catalyzes the conversion of fructose to fructose-1-phosphate, the first step by which fructose can enter the fatty acid synthesis pathway. The data demonstrate that breast cancer cells also express fructose 1-P-aldolase (FPA) mRNA, the second enzyme in this pathway. As depicted in FIG. 8, RT-PCR analysis employing specific primer pairs for the β-isoform of FPA demonstrated FPA mRNA expression using total RNA derived from MCF-7 cells cultured in 2 mM glucose, 5.5 mM glucose, and 5.5 mM fructose. As expected human hepatic tissue exhibited FPA mRNA, whereas muscle, which does not express the FPA β-isoform, was negative. Also observed was FPA mRNA expression in two surgically resected human breast cancers and in paired adjacent normal breast tissue from the same individual. These results support the inventors' belief that breast cancer cells can potentially utilize fructose via alternative metabolic pathways to glucose to generate higher ATP levels for the enhanced growth rates.

Figure 9:
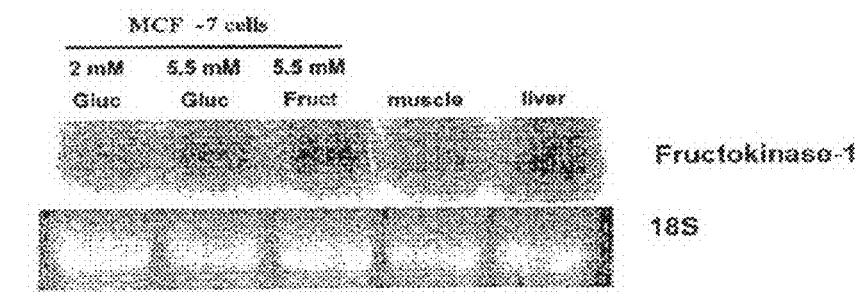
FIG. 9 depicts Northern blot analysis of fructokinase-1 mRNA levels in MCF-7 breast cancer cells in accordance with an embodiment of the present invention. 20 μg total RNA was used to measure FK-1 mRNA levels in the MCF-7 cells following growth in 2 mM glucose, 5.5 mM glucose, or 5.5 mM fructose for 24 h. FK-1 was also detected in human liver, with lower levels in muscle tissue.

In additional studies, the inventors used Northern blot to confirm significant FK-1 mRNA expression in the breast cancer cells. As depicted in FIG. 9, fructokinase-1 mRNA expression was detected in MCF-7 cells cultured in 2, and 5.5 mM glucose, and 5.5 mM fructose, and in human muscle and liver tissue. Highest FK-1 expression was observed in liver tissue and intriguingly in the MCF-7 cells cultured in 5.5 mM fructose, suggesting that fructose treatment may actually induce this key metabolic enzyme for fructose metabolism via the alternative pathway described herein.

Example 4

Fructose Treatment Induces GLUT-5

Figure 10:
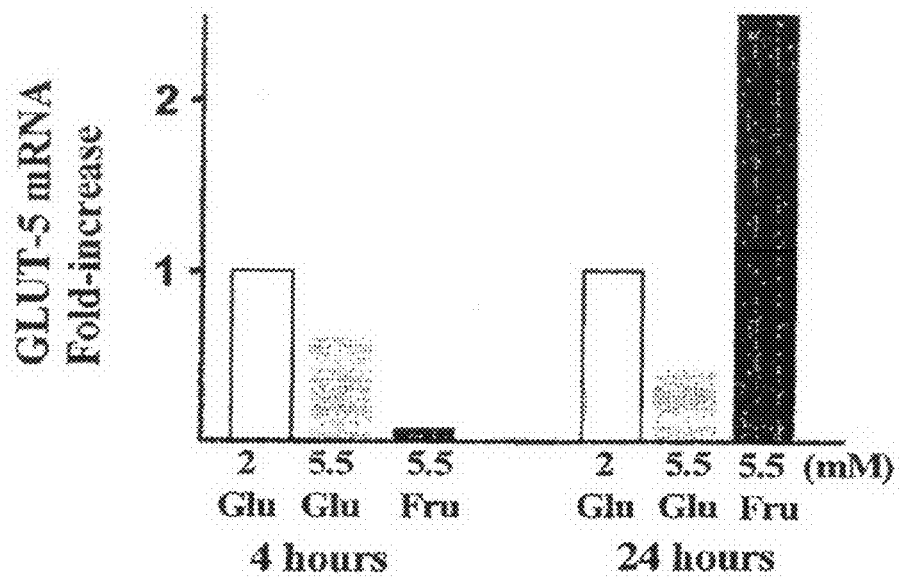
FIG. 10 depicts GLUT-5 expression levels in accordance with an embodiment of the present invention. MCF-7 breast cancer cells were incubated in 2 mM glucose (Glu), 5.5 mM glucose (Glu) or 5.5 mM fructose (Fru) for 4 or 24 hours, after which GLUT-5 expression was quantified using real-time RT-PCR, normalized to GAPDH levels, and expressed as fold-increase compared to GLUT-5 levels detected in MCF-7 cells cultured in 2 mM glucose for a similar time period.
Figure 11:
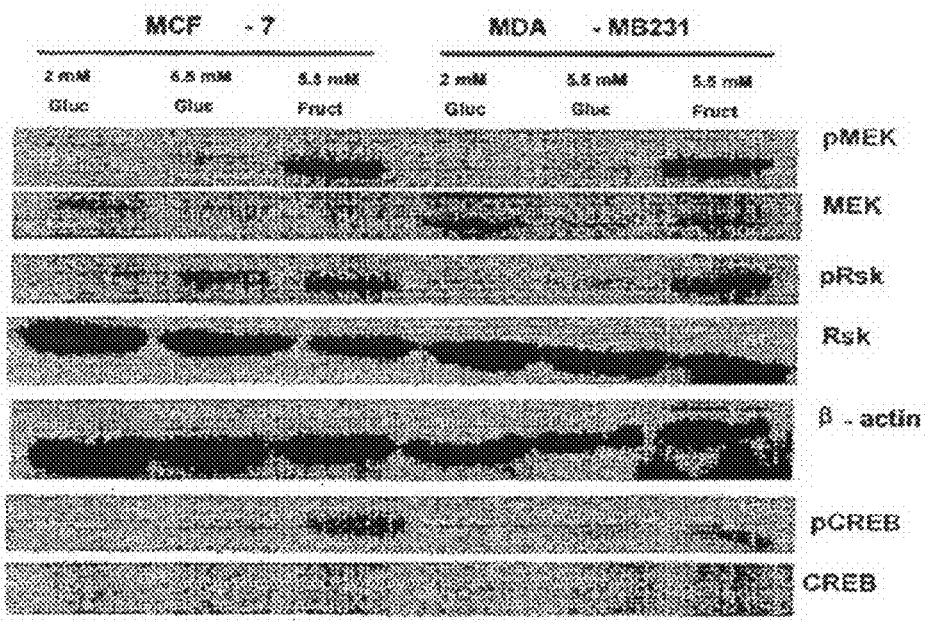
FIG. 11 depicts increased breast cancer phosphorylated-MEK, phosphorylated Rsk, and phosphorylated CREB in accordance with an embodiment of the present invention. MCF-7 breast cancer cells were incubated in 2 mM glucose, 5 mM glucose or 5 mM fructose for 24 hours, after which Western blot analysis on total protein lysates was employed to examine components of the MAP kinase pathway. Increased breast cancer phosphorylated-MEK (pMEK), phosphorylated Rsk (pRsk), and phosphorylated CREB (pCREB) levels were observed in MCF-7 cells after incubation in 5 mM fructose compared to levels seen in 5 mM, and 2 mM glucose for 24 h. Total MEK, Rsk, and CREB levels, and β-actin served as loading controls.

Cellular fructose uptake is facilitated by a member of solute carrier family 2, called glucose transporter type 5 (GLUT-5). Following incubation of MCF-7 breast cancer cells in 2 mM, 5.5 mM glucose or 5.5 mM fructose for 48 h, total RNA was harvested, and analyzed by quantitative real-time RT-PCR analysis using GLUT-5 specific primers to quantify GLUT-5 mRNA expression. GLUT-5 expression was normalized to GAPGH mRNA expression, and expressed as fold-change in comparison to control breast cancer cells incubated in 2 mM glucose for 4, and 24 hours. As depicted in FIG. 10, no significant change in GLUT-5 mRNA expression was observed following incubation of the breast cancer cells in 5.5 mM glucose or 5 mM fructose for 4 hours, but after 24 hour incubation, a two-fold increase in the specific fructose transporter, GLUT-5, was observed in cells incubated in 5.5 mM fructose compared to GLUT-5 expression in cells incubated in 5.5 mM glucose.

Example 5

Fructose-Treatment Induces the MAPK Pathway in Breast Cancer Cells

Figure 12:
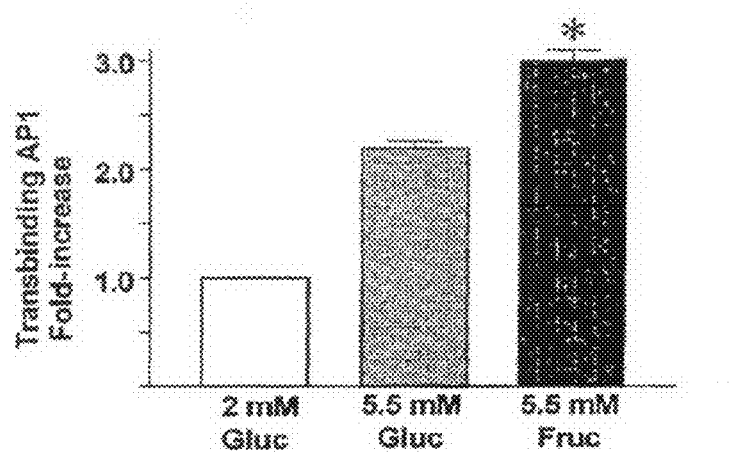
FIG. 12 depicts an increase in AP1 activation in fructose-treated cells in accordance with an embodiment of the present invention. MCF-7 breast cancer cells were incubated in 2 mM glucose, or 5 mM glucose or fructose for 24 h, after which nuclear extracts were incubated with a biotinylated AP-1 probe in binding buffer. AP-1/AP1 probe complexes were next conjugated to a streptavidin-coated assay plate and detected using an AP-1 specific antibody, followed by binding of a horseradish-peroxidase conjugated secondary antibody, and detection by a colorimetric reagent. *, p<0.001.

Although several signal transduction pathways are likely involved in the fructose-mediated enhanced breast cancer growth and while not wishing to be bound by any particular theory, the inventors believe that the MAP-kinase pathway is involved. The inventors have used Western blot analysis to examine the MAPK pathway in breast cancer cells incubated in 2 mM glucose, 5.5 mM glucose, and 5.5 mM fructose for 48 hours. MEK mediated phosphorylation of the p44/42 MAP kinase (ERK) is the first step in this cascade and the inventors observed increased expression of phospho-MEK (pMEK) in MCF-7, and MDA-MB231 breast cancer cells grown in 5.5 mM fructose, in comparison to cells grown in 5.5, and 2 mM glucose. Activation of MEK, and subsequently ERK results in phosphorylation of $p90^{Rsk}$, which leads to transcriptional activation of CREB and AP1, which bind to cAMP or AP1 response elements respectively, activating gene transcription and promoting cellular growth. After 24 h incubation of breast cancer cells in 5.5 mM fructose, the inventors observed increased phospho-Rsk (pRsk), and phospho-CREB (pCREB), in comparison to cells grown in 5.5, and 2 mM glucose for the same time period. Furthermore, using an ELISA-based transbinding AP1 assay (Panomics), the inventors demonstrated a 3-fold increase in AP1 activation in 5.5 mM fructose-treated cells in comparison to a 2.2 fold increase in cells treated with 5.5 mM glucose (FIG. 12; *p<0.001). These results provide further insight into the mechanism(s) for the fructose-induced increased breast cancer proliferation that were seen.

Example 6

Characterization of the Mechanism(s) of Fructose-Enhanced Breast Cancer Proliferation In Vitro Firstly, ER-positive MCF-7, and ER-negative MDA-MB231 breast cancer cells are cultured in a range of concentrations of glucose, and fructose to confirm, and extend the findings that culture in fructose results in increased breast cancer growth. The data (FIG. 5) shows that breast cancer cells exhibit higher proliferative rates at all fructose concentrations between 2.5, and 25 mM.

Briefly, MCF-7, and MDA-MB231 cells (~10,000 per well) are first plated on to 96-well plates, in standard whole serum (10% FBS), high glucose (25 mM) DMEM medium. Cells are then incubated overnight in whole serum (10% FBS) low glucose (2 mM) DMEM. The following day, cells are changed to medium containing a range of glucose or fructose (5, 10, 25, 50, 75, & 100 mM) for times 24, 48, 72 and 96 h. Proliferative rates are measured in the cells using the MTS assay. Briefly, cells are incubated with 'One Solution' (containing-tetrazolium compound MTS and phenazine ethosulfate reagent) at 37° C. for 2 h. Absorbance (490 nm) which correlates closely with cell proliferation measured using Cell-Titer 96 AQueous One Solution Cell Proliferation Assay (MTS) according to manufacturer's instructions (Promega, Madison, Wis., USA). This rapid assay is ideal for these large numbers of samples, and quickly allows determination of optimal dose ranges, and treatment times for subsequent experiments. The focus is on physiologically relevant glucose & fructose concentrations (5-25 mM), to translate these findings to human breast cancer. Proliferative rates are also quantified by measurement of bromodeoxyuridine (BRDU) uptake in the fructose-, and glucose-treated cells. Breast cancer cells are also plated in 12-well dishes, incubated in a similar range of glucose, and fructose concentrations for 24-96 h, and aliquots of the fructose-, and glucose-treated cells then prepared for FACS analysis to measure cell-cycle profiles.

Example 7

Fructose/Glucose Uptake and Oxidative Phosphorylation

Two areas are important: (1) Increased GLUT expression resulting in increased fructose uptake into the cell; and (2) Increased expression of key glycolytic enzymes, particularly fructokinase-1, and inducible phosphofructokinase-2, that result in increased oxidative phosphorylation.
GLUT Expression As noted above, a family of glucose-uptake and transporter (GLUT) proteins regulate cellular glucose uptake, and previous studies have demonstrated increased GLUT expression in cancer, including the fructose-selective GLUT-5 (Zamora-Leon S P, Dolde D W, Concha I I, Rivas C I, Delgado-Lopez F, Baselga J, Nualart F, Cartos-Vera J. Expression of the fructose transporter GLUT5 in human breast cancer. Proc Natl Acad Sci 93: 1847-52, 1996; Macheda M L, Rogers S, and Best J D. Molecular and cellular regulation of glucose transporter (GLUT) proteins in cancer. J Cellular Physiol 202: 654-662, 2005; Smith T A D. Facilitative glucose transporter expression in human cancer tissue. Brit J Biomed Sci 56(4): 285-292, 1999; Rogers S, Docherty S E, Slavin J L, Henderson and Best J D. Differential expression of GLUT12 in breast cancer and normal breast tissue. Cancer Letters 193(2): 225-233, 2003). Increased GLUT-mediated fructose uptake, thereby increasing substrate availability, contributes to increased proliferation. Therefore, breast cancer GLUT expression is examined RT-PCR and Western blot analysis in the fructose- and glucose-treated breast cancer cells. While not wishing to be bound by any particular theory, it is believed that the increased fructose-mediated proliferation is due to enhanced GLUT-5-trafficked fructose uptake, and fructose is able to self-regulate its own transporter. SiRNA approaches are employed to silence GLUT-5 expression in the breast cancer cells and to determine the alteration in increased growth rates observed in the fructose-treated breast cancer cells. In parallel experiments, vectors harboring GLUT-5 are transiently transfected into MCF-7, and MDA-MB231 cells. Increased GLUT-5 expression are confirmed by Western blot, and the effects of increased GLUT-5 expression on breast cancer cell growth rates across a range of fructose and glucose concentrations examined.
Oxidative Phosphorylation Three approaches are used to examine oxidative phosphorylation in the fructose-treated and glucose-treated breast cancer cells. Firstly, several key glycolytic enzymes following breast cancer fructose-, or glucose-treatment, is quantitated using RT-PCR, and Northern blot analysis. While not wishing to be bound by any particular theory, it is believed that there is increased glycolysis, and hence oxidative phosphorylation in the fructose-versus glucose-treated cells, one would expect that expression of the key glycolytic enzyme phospho-fructokinase-1 is increased in the fructose-treated breast cancer cells, compared to the glucose-treated cells. Briefly, after glucose- or fructose-treatment, total RNA (1-2 µg) from the MCF-7, and MDA-MB231 breast cancer cells are treated with DNAse I, at 37° C. for 30 min and reverse transcribed using SuperScript First-Strand Synthesis system for RT-PCR (Invitrogen). Specific oligonucleotide primer pairs are used to amplify phospho-fructokinase-1 expression in the glucose- or fructose-treated cells (PFK-1: SEQ ID NO: 3 (3'agcctccctatccaggaaaa) and SEQ ID NO: 4 (5'tagacag-cagccaggacctt)) using polymerase chain reaction (PCR). PCR for 18S is performed as an internal control on both RT positive and negative samples to confirm cDNA product integrity. Aliquots of the PCR products are electrophoresed on 1% agarose gels and stained with ethidium bromide to visualize PCR products. Band intensity is quantified using scanning densitometry.

While not wishing to be bound by any particular theory, it is believed that the increased glycolysis is due to increased cancer fructose kinase-1 (FK-1), and inducible phosphofructokinase-2 (iFPK-2) activity. Northern blot analysis is used to quantify FK-1, and iPFK-2/FBPase-2. Briefly, total RNA is extracted from the fructose-, or glucose-treated MCF-7, and MDA-MB231 breast cancer cells in Trizol, and Northern blot analyses using full-length FK-1, or iPFK-2/FBPase-2 [α-32P]dCTP-random primer labeled cDNA as probes, performed by standard procedures (Heaney A P, Singson R, McCabe C J, Nelson V, Nakashima M, Melmed S. Pituitary Tumor Transforming Gene: a novel marker in colorectal tumors. Lancet 355:716-719, 2000). RNA integrity is verified by observing the rRNA bands in ethidium bromide gels under UV, and the level of mRNA is quantified by densitometric scanning of the autoradiograms and corrected for 18s rRNA expression (Sambrook J, Fristsch E F, and Maniatis T. Molecular Cloning: A Laboratory Manual, edited by Nolan C. Cold Spring Harbor, N.Y.: Cold Spring Harbor, p. 7.3-7.5, 1989).

If inducible phosphofructokinase-2 (iFPK-2) activity is increased, increased levels of the metabolite fructose-2,6 bis-phosphate (Fru-2, 6-P2) in the fructose-compared to glucose- or vehicle-treated cells may be observed. Therefore, Fru-2, 6-P2 levels are quantitated. Briefly, fructose-, or glucose-treated MCF-7, and MDA-MB231 cells are homogenized in 0.1 M NaOH, heated to 80° C. for 15 min, and centrifuged at 12,000 g for 5 min. Fru-2, 6-P2 is then determined in the supernatants by its ability to activate pyrophosphate-dependent iPFK-1 from potato tubers as described by Van Schaftingen et al. (Van Schaftingen E. Fructose 2,6-bisphosphate. Adv Enzymol Relat Areas Mol Biol 59: 315-395, 1987; Van Schaftingen E, Lederer B, Bartrons R, and Hers H G. A kinetic study of pyrophosphate: fructose-6-phosphate phosphotransferase from potato tubers. Application to a microassay of fructose 2,6-bisphosphate. Eur J Biochem 129: 191-195, 1982; Van Schaftingen E, Jett M F, Hue L, and Hers H G. Control of liver 6-phos-phofructokinase by fructose 2,6-biosphophate and other effectors. Proc Natl Acad Sci USA 78: 3483-3486, 1981). The glycolytic metabolites are then measured spectrophotometrically in neutralized perchloric extracts, using standard enzymatic methods.

As discussed above, fructose can potentially bypass the rate-limiting step (catalyzed by PFK-1) of glycolysis, if it is metabolized directly to fructose-1-phosphate by the enzyme fructokinase-1. The inventors' data demonstrates that breast cancer MCF-7 cells express FK-1 mRNA. Therefore, Northern blot is used to quantify fructokinase-1, and fructose 1-P aldolase mRNA levels, the second enzyme in this pathway. The latter catalyzes the conversion of fructose-1-phosphate to dihydroxyacetone phosphate, and its presence confirms that breast cancer cells can traffic fructose directly into the lipogenesis pathway, bypassing regulatory controls that restrict glycolytic glucose trafficking. To determine the activity of fructokinase-1 (FK-1), fructose 1-phosphate levels, the metabolite of the FK-1 catalyzed reaction, are measured Fructose 1-phosphate is measured using a commercially available assay based on its conversion to fructose 1,6-bisphosphate by a bacterial fructose-1-phosphate kinase. Briefly, the open reading frame encoding *Escherichia coli* Fru1PK has been introduced in an expression plasmid (pET3a) based on the T7 promoter-driven system, and is used to overexpress the enzyme, and the preparation can be used in an enzymatic assay to measure specifically fructose 1-phosphate levels in cell or tissue extracts.

Thirdly, lactate production, as this is a key metabolite of glycolysis, and as noted previously serum lactate levels correlate with several outcome measures in human cancer, is measured. For measurement of lactate production, cell suspensions attached to microcarriers are used. Briefly, after incubation of the breast cancer cells in fructose or glucose, cells are trypsinized, washed, and added to preswollen Cytodex-1 microcarriers (Pharmacia Biotech), and suspended in DMEM. To achieve a maximum yield of cells attached to microcarriers, the cultures are stirred for 5 min every 30 min. After 2 h, the medium is changed and the cultures stirred continuously at 60 rpm. Microcarrier cultures are then incubated for up to 48 h. Cells attached to microcarriers are then rinsed and suspended in Krebs bicarbonate buffer containing 2.5 mM CaCl2, 2% BSA, and 10 mM glucose prior to measurement of lactate production.

Expression vectors harboring full-length wild-type cDNA from iPFK-2/FBPase-2, and a truncated mutant iPFK-2/FBPase-2 that only exhibits bisphosphatase activity (pFBPase-2) are generated. Wt- and Mut-iPFK-2/FBPase-2 are transiently transfected into MCF-7, and MDA-MM231 cells, and expression is confirmed by RT-PCR analysis using specific sense and antisense Wt-, and Mut-primers (Darville M I. Crepin K M, Vandekerckhove J, Van-Damme J, Octave I N, Rider M H, March and M J, Hue L, and Rousseau G G. Complete nucleotide sequence coding for rat liver 6-phosphofructo-2-kinase/fructose-2,6-bis phosphatase derived from a cDNA clone. FEBS Lett 224: 317-321, 1987.). Wt-, and Mut-MCF-7, and MDA-MB231 transfectants are incubated in fructose, or glucose for 24 h, and effects of overexpression of the Wt-, or Mut-iPFK-2/FBPase-2 on proliferative rates are examined. As Wt-iPFK-2/FBPase-2 further increases Fru-2, 6-P2 levels to further induce PFK-1, and while not wishing to be bound by any particular theory, it is believed that breast cancer cells transfected with the Wt-iPFK-2/FBPase-2 will exhibit higher proliferative rates than vector-transfected cells, and the proliferative rates will be further increased by fructose-treatment. While not wishing to be bound by any particular theory, the inventors believe that Mut-iPFK-2/FBPase-2 expression drives glycolysis towards glycogen synthesis, reduces proliferative rates, and abrogates the fructose-induced breast cancer proliferative rates.

Example 8

Signal Transduction

Although it is likely that several signal transduction pathways are involved in fructose-mediated breast cancer proliferation, previous studies have demonstrated that ras-transformation in rat-1 fibroblasts led to increased F2, 6 BP levels, and aerobic glycolysis, and multiple potential binding sites for several ras-activated transcription factors, including myc, and nuclear factor kB have been identified on the iPFK-2 promoter (Norris J L and Baldwin A S Jr. Oncogenic ras enhances NF-κB transcriptional activity through Raf-dependent and Raf-independent mitogen-activated protein kinase signaling pathways. J Biol Chem 274: 13841-13846, 1999; Minchenko A, Leschinsky I, Opentanova I, Sang N, Srinivas V, Armstead V and Caro J. Hypoxia-inducible factor-1-mediated expression of the 6-phosphofructo-2-kinase/fructose-2,6-bisphosphatase-3 (PFKFB3) gene. Its possible role in the Warburg effect. J Biol Chem 277: 6183-6187, 2002). Therefore, while not wishing to be bound by any particular theory, the inventors believe that the MAP-kinase pathway is likely to be important. Several MAPK cascades have been identified including the extracellular signal-related kinase pathways (ERK 1/2, ERK5), and the stress activated kinase pathways (JNK/SAPK, p38 MAPK). As all MAPK pathways operate through sequential phosphorylation events, Western blot analysis using phospho-specific antibodies is employed to examine $p90^{RSK}$, CREB, c-fos, and ELK-3 levels in protein lysates harvested from MCF-7, and MDA-MB231 cells cultured in 2, 5, 10, and 25 mM fructose, and glucose for 24 h. Additionally, MCF-7, and MDA-MB231 cells are transiently transfected with CRE-luciferase, AP-1-luciferase, and SRE-luciferase reporter constructs. A β-Galactosidase reporter construct is co-transfected as a control. Following incubation of the transient transfectants in a range of glucose, and fructose concentrations as before (5, 10, & 25 mM) for 24 h, cell lysates are harvested, and luciferase activities measured, and normalized for p-Gal to correct for changes in cell number or transfection efficiency. All samples are analyzed in triplicate, a minimum of three separate experiments are conducted for each study outlined above, and statistically analyzed as described below. To further characterize the role of the MAP-kinase pathway in fructose-mediated breast cancer proliferation, proliferative rates in the fructose-, and glucose-treated breast cancer cells with, and without pharmacological inhibition of the MAPK-pathway using the specific MKK 1/2 and, MEK 1/2 inhibitors PD98059, and U0126, are compared. Additionally, plasmids encoding a dominant negative MAPK, or empty vector alone (Pearson G, Robinson F, Gibson T B, Xu B, Karandikar M, Berman K, Cobb M H. 2001. Mitogen-activated protein (MAP) kinase pathways: Regulation and physiological functions. *Endo Rev* 22: 153-183) are transiently co-transfected into MCF-7 and MDA-MB231 breast cancer cells before incubation in fructose or glucose. Dominant negative (DN) MAPK expression is confirmed by western blot, and proliferative rates in fructose-treated DN MAP-kinase expressing breast cancer cells compared with glucose-treated DN MAP-kinase expressing cells, and fructose-, and glucose-treated control vector transfected cells. Protein aliquots from fructose-, and glucose-treated breast cancer cells are also analyzed to examine activation of other signal transduction pathways, including the PI-3K/AKT and phospholipase-C-γ pathways, as these pathways are extremely important in breast cancer (Mills G B, Kohn E, Lu Y, Eder A, Fang X, Wang H, Bast R C, Gray J, Jaffe R, Hortobagyi G Linking molecular diagnostics to molecular therapeutics: targeting the PI3K pathway in breast cancer Semin Oncol. 30 (Suppl 16): 93-104, 2003).

Example 9

Determine Effects of Refined Fructose Consumption on In Vivo Breast Cancer Growth The effects of 10% and 20% added refined fructose and glucose on breast cancer development are examined. These percentages are chosen as they are conservative but meaningful equivalent to current human refined carbohydrate intake. Therefore, refined glucose or fructose is administered to mice overexpressing activated neu oncogene under the control of the mouse mammary tumor virus (MMTV) promoter. Effects of treatments on time to tumor development and tumor multiplicity are examined.

Example 10

Transgenic Mice

Female MMTV-erbB2 transgenic mice are purchased from the Jackson Laboratory. In this murine breast cancer model, the MMTV promoter from the mouse mammary tumor virus long terminal repeat causes the erbB2 gene to be expressed in the mammary gland. These animals reproducibly develop focal mammary tumors that arise spontaneously at 4 months, with a median incidence of 205 days. Mice are housed in animal facilities, in accordance with institutional care and use guidelines.

Example 11

Treatment and Data Collection

The mice receives a commercially purchased standard chow diet (Labdiet.com, certified rodent diet 5002), eat ~5 g per day, and receive a total daily intake of approximately 1700 Kcal, comprising 64.5% CHO, 11.8% fat, 23.5% protein, and 4.6% fiber. Mice also receive a fructose or glucose sugar solution containing 0.429 or 0.84 g fructose or glucose (diluted in 100 ml) which equate to 10% or 20% added refined carbohydrate respectively or vehicle daily from age 3 months to 12 months. Developing tumors in the fructose-, glucose-, and vehicle-fed mice are measured twice a week with electronic calipers, and tumor volumes determined by multiplying the square of the width (w) by the length (l) and dividing by two (i.e., $(w^2 l)/2$). Individual animal weights, tumor size and tumor location are recorded for each animal twice a week. Animals are euthanized when they develop tumors of 1000 mm3 or more or at the end of the experiment, at the same time of day (9 am) to limit temporal variations in glucose, insulin, and other parameters. Two hours before killing, the mice are injected intraperitoneally with bromodeoxyuridine (3 mg/mL) in phosphate-buffered saline, (100 μL/10 g body weight). The end of the experiment is defined as the time when all vehicle-treated mice have developed a tumor (usually at ~330 days of age). At that time, all remaining mice (vehicle-, glucose-, and fructose-treated) are killed, tumors resected, and studied as below.

Example 12

Histology and Biomarker Analysis—Breast Cancer

For histology, breast tumors are fixed in 10% formalin and embedded in paraffin. Tissue sections are mounted on slides and processed for hematoxylin-eosin staining. Immunohistochemical staining is performed for erbB2 to confirm tumor expression, and for proliferating cell nuclear antigen (PCNA & Ki-67) to compare tumor proliferative rates in the mice. Briefly, tissue sections are deparaffinized in xylene, rehydrated, endogenous peroxidase activity blocked, and non-specific binding reduced with goat serum. Sections are then incubated with one of the following antibodies: rabbit anti-c-erbB2 antibody (Neomarkers) (1:50), or monoclonal anti-PCNA Or Ki-67 (MIB-1) antibodies (1:200). Washed sections are incubated with biotinylated goat anti-rabbit antibody, incubated with the ABC kit (Vector labs), and 3-amino-9-ethylcarbazole to visualize the peroxidase complex. Levels of pRb are evaluated by visual assessment with a semiquantitative scoring system rating staining intensity (from 0 to 3). Staining for bromodeoxyuridine (BRDU) is performed with the DAKO Animal Research Kit system. Briefly, tissue sections are prepared, endogenous peroxidase blocked, and nonspecific binding reduced as before. BRDU are stained with a mouse anti-BRDU monoclonal antibody (DAKO). Slides are incubated with streptavidin-horseradish peroxidase, and visualized with diaminobenzidine chromagen. Counterstaining is performed with hematoxylin. Stained sections are reviewed, and scored by counting the positive and negative cells in 10 high-powered fields in tissue samples from 4 mice from each group. Results are expressed as an average percentage with 95% confidence intervals.

Example 13

Glucose, Insulin, IGF1, Lipid, and Inflammatory Cytokine Levels

Fructose-, glucose-, and vehicle-treated mice are fasted for 24 h (9 am-9 am) every 4 weeks, and at euthanasia, blood are collected by the tail clip method into chilled tubes for assay of glucose, insulin, lipid and inflammatory cytokine levels. Plasma glucose concentrations are determined using Glucotrend 2 (Roche Diagnostics); plasma insulin (Linco Res), and IGF-1 Phoenix Pharmaceuticals levels are measured using solid phase two site enzyme immunoassays; plasma triglyceride, free fatty acids, lactate, and p-hydroxybutyrate concentrations are analyzed using commercially available kits (Sigma Diagnostics). Serum inflammatory markers include C-reactive protein, IL-6 (R&D Systems), serum sialic acid, soluble intracellular and vascular adhesion molecules (sICAM-1, and sVCAM-1) (Bender MedSystems Inc), and amyloid A levels, and are assayed using commercially purchased ELISA based kits (R & D, Quantikine). All parameters are measured in triplicate in the breast cancer susceptible mice, and means compared between the fructose-, and glucose-, and vehicle-fed animals, at the various timepoints using ANOVA with Bon-Ferroni post t-tests for multiple comparisons. Time curves are graphed to compare trends in fasting glucose, insulin, lipid, and triglyceride levels, and inflammatory markers over the course of dietary treatment.

Example 14

Alternative Approaches

Allotypic graft tumors are generated by injecting cells derived from erbB2 Tg mice (NK), into the mammary gland of FVB/N mice (these are the background strain).

Example 15

Figure 13:
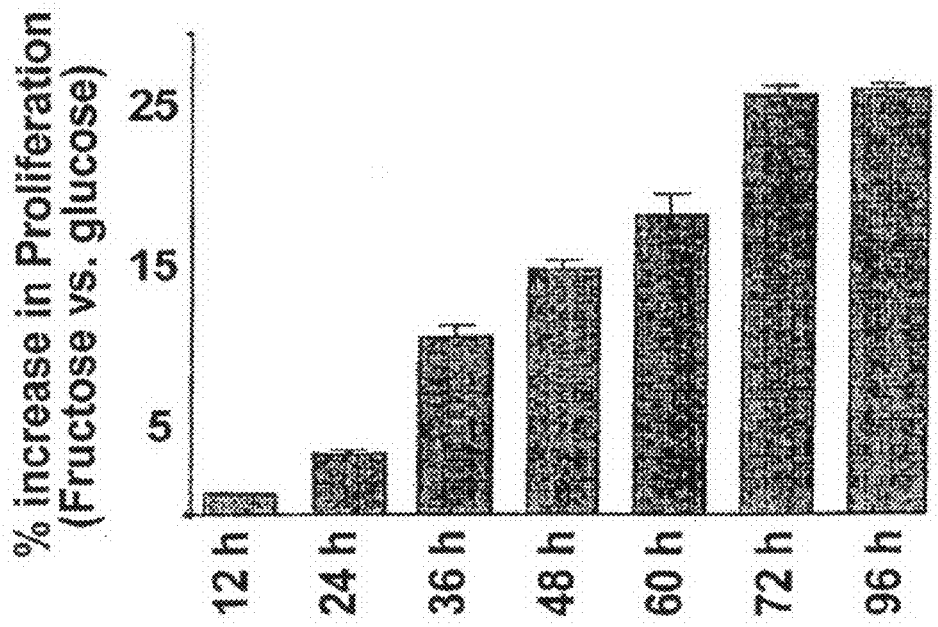
FIG. 13 depicts higher proliferation rates in pancreatic cancer cells in fructose (5.5 mM) than glucose (5.5 mM) containing medium in accordance with an embodiment of the present invention. PANC-1 cells were pre-incubated in 2 mM glucose, after which they were plated in 5.5 mM fructose or glucose for times between 12-72 h, after which proliferative rates were measured using an MTS assay. Proliferative rates are expressed as the percentage difference between cells grown in 5.5 mM fructose versus 5.5 mM glucose. p<0.01 for times >48 h.

Pancreatic Cancer Cells Exhibit Increased In Vitro Proliferation in Fructose in Comparison to Glucose Standard media for maintenance cancer cell line culture, including pancreatic cancer cells such as PANC-1 cells contain either low- (5-7 mM), or high- (12-25 mM) glucose concentrations. Clearly, apart from the setting of hyperglycemia, as in patients with diabetes, the glucose concentrations in which pancreatic cancer cells are maintained in vitro are much higher than normal physiological conditions, which range between 2-5 mM glucose. While the inventors did not wish to expose the cells to serum-free conditions, as is customary when testing potential "growth-factor" effects, the inventors sought to conduct the experiments under conditions that might ultimately be physiologically relevant to patients with pancreatic cancer. Therefore, the inventors first pretreated the pancreatic cancer cells overnight in standard DMEM medium containing low physiological glucose concentrations (2 mM glucose), and standard 10% fetal bovine serum. The pancreatic cancer cells were then incubated for times between 12, and 96 hours in standard DMEM medium containing 10% fetal bovine serum, and 5.5 mM glucose or 5.5 mM fructose. Proliferative rates were then measured in replicate (minimum of 6) aliquot wells of the pancreatic cancer cells, and the change (expressed as percent increase) in proliferative rates compared between cells grown in glucose, or fructose containing medium. As depicted in FIG. 13, PANC-1 pancreatic cancer cells began to exhibit higher proliferative rates in 5.5 mM fructose, compared to cells grown in 5.5 mM glucose by 24 h, the difference in proliferative rates continued to increase, reaching ~13% at 48 h, was maximal at 72 h, by which time pancreatic cancer cells demonstrated a 23% higher proliferative rate in 5.5 mM fructose than 5.5 mM glucose, but in otherwise identical conditions (p<0.01 for all times >48 h).

Figure 15A:
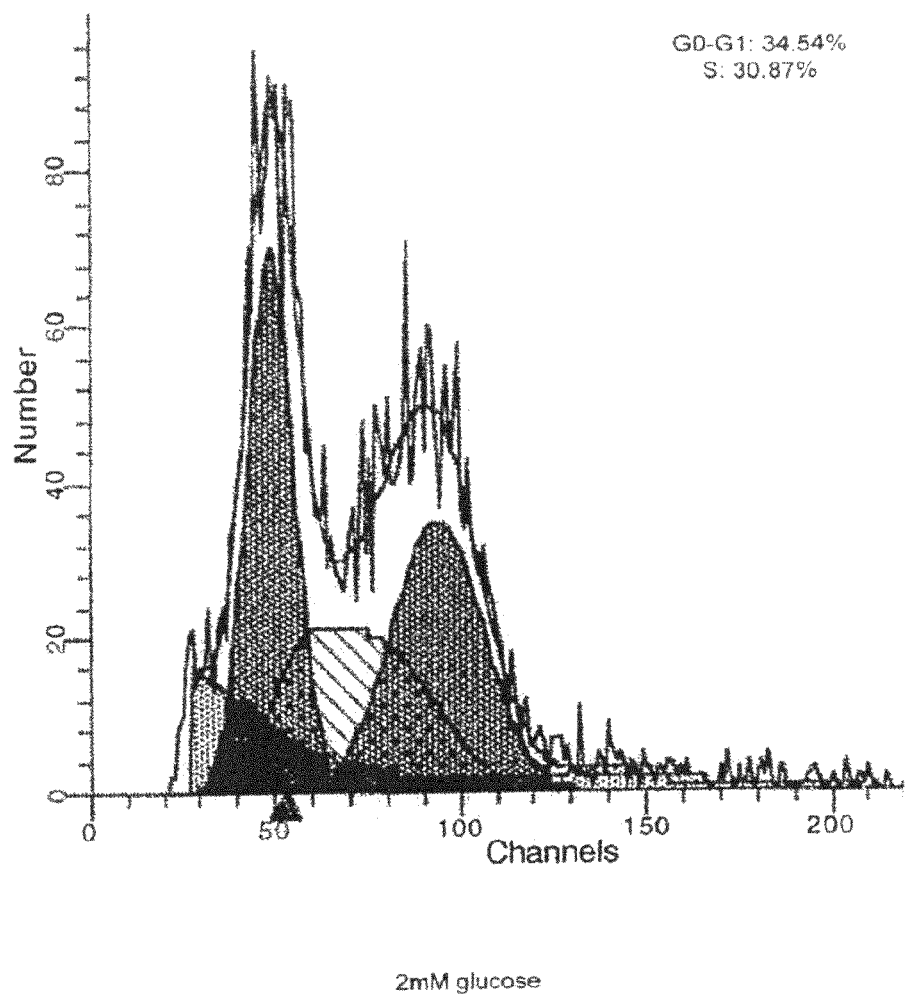
FIG. 15 depicts in the G0/G1 phase and the DNA synthesis (S) phase of pancreatic cells in glucose and fructose in accordance with an embodiment of the present invention. PANC-1 cells were plated in 2, and 5.5 mM glucose or 5.5 mM fructose for 48 h, after which cells were fixed in methanol, nuclei were stained with propidium iodide, and aliquots subjected to FACS analyzes.
Figure 15B:
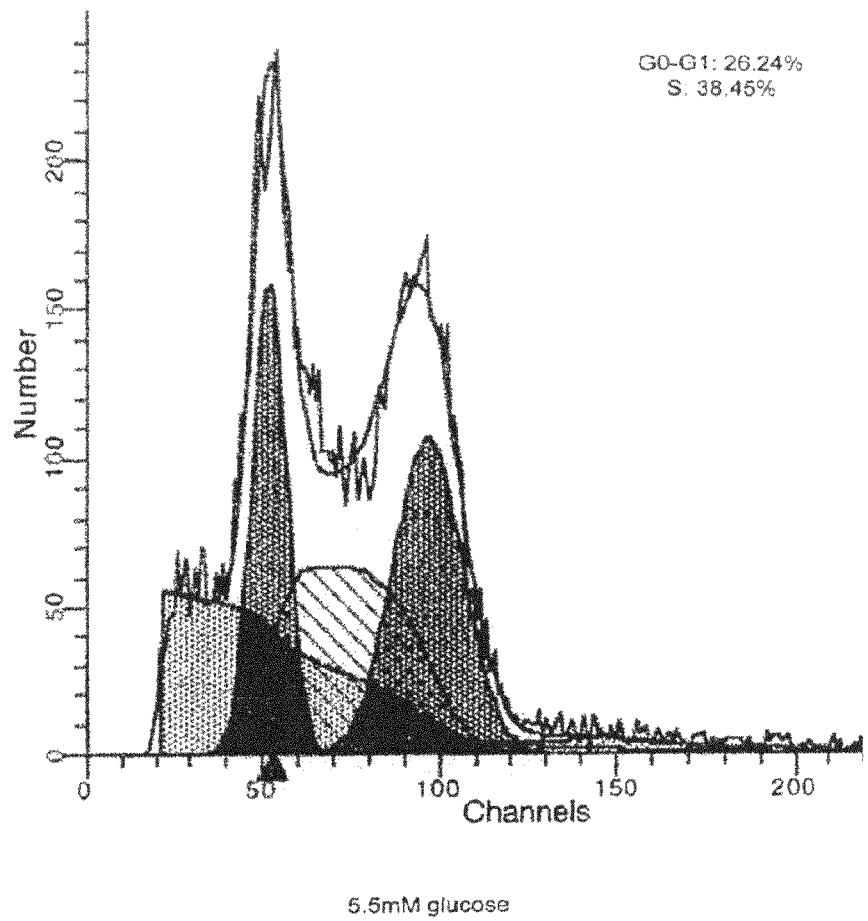
Figure 15C:
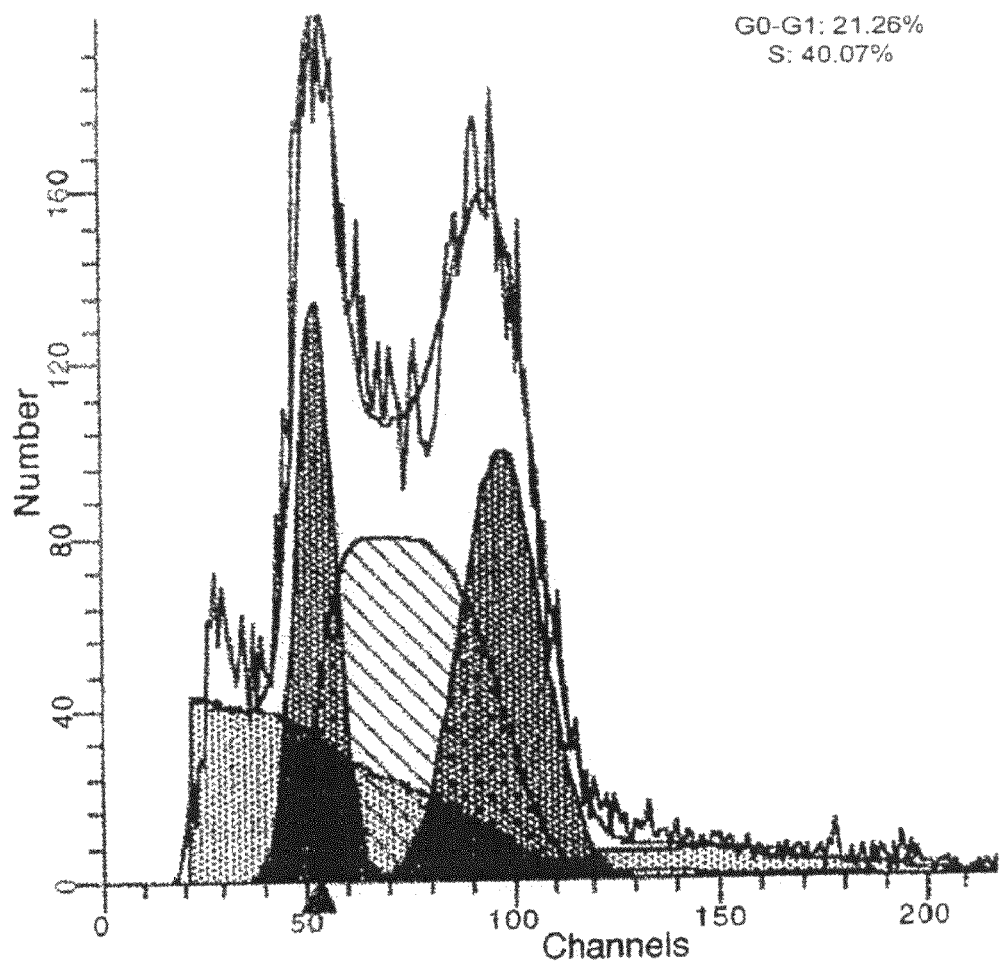

This first result intrigued the inventors, but given there is little documentation regarding physiological fructose concentrations, the inventors first considered that the "apparent" pro-proliferative effects of fructose were simply a consequence of the highly stylized in vitro experimental conditions, and that if the pancreatic cancer cells were cultured in higher glucose concentrations, this would result in similar proliferative rates to those the inventors observed following culture in 5.5 mM fructose. Therefore, in the next experiments, the inventors compared proliferative rates of the PANC-1 pancreatic cancer cells following culture for 72 h in a range of fructose, and glucose concentrations (2-25 mM). This timepoint was chosen as the inventors had seen maximal pancreatic cancer cell proliferation in 5.5 mM fructose at 72 h. As depicted in FIG. 14, higher glucose concentrations (up to 25 mM glucose) still did not result in the same magnitude of increase in pancreatic cancer cell proliferation as that which was induced by fructose concentrations from 5 mM upwards. In fact, cells grown for 72 hours in 5 mM fructose exhibited higher proliferative rates than cells grown for 72 h in 5-fold higher glucose concentrations (25 mM) (FIG. 14). The fructose-mediated increased pancreatic cancer proliferation was first demonstrable around 5 mM fructose, and interestingly not appearing to increase further with higher fructose levels. While not wishing to be bound by any particular theory, the inventors believe that this latter finding may be because the PANC-1 cells are proliferating at close to maximal capacity by 72 h, once they are exposed to comparatively low fructose concentrations (5 mM). MTS assay was employed to measure pancreatic cancer cell proliferative rates, which utilizes mitochondrial oxidation to quantify cell proliferation. As the inventors were examining carbohydrate-mediated effects, the inventors considered the change observed in proliferative rates, as measured by this assay, simply reflected changes in mitochondrial oxidation. Therefore, two additional methods were utilized to examine proliferative rates following fructose-treatment. Firstly, the inventors examined cell cycle profiles in the pancreatic cancer cells following culture in 5.5 mM glucose, or 5.5 mM fructose for 48 h, after which cells were fixed in methanol, and stained with propidium iodide prior to flow-activated cytometric analysis (FACS) to determine the percentage of cells in the resting G0/G1 phase, and the DNA synthesis (S) phase. If the sugars were inducing pancreatic cancer cell proliferation, the inventors would expect to see an increased percentage of cells in the S-phase, with a concordant reduced percentage of cells in the G0/G1 phase. As depicted in FIG. 15, following culture in 5.5 mM glucose, an increase of ~8% of cells in S-phase was observed, in comparison to PANC-1 cells cultured in 2 mM glucose, in keeping with some increase in cell proliferation. However, following incubation of the PANC-1 cells in 5.5 mM fructose, a more striking increase (~17%) in the percentage of PANC-1 cells in the proliferative S-phase (PANC-1: 2 mM glucose, 30.9%; 5.5 mM glucose, 38.5%; 5.5 mM fructose, 47%) was observed. In conjunction with increased S-phase population, a concordant reduction in cells in the resting G0/G1 (PANC-1: 2 mM glucose, 34.5%; 5.5 mM glucose, 26.2%; 5.5 mM fructose, 21.2%) was noted (FIG. 15), supporting the MTS assay data, and indicating that the pancreatic cancer cells exhibited higher proliferative rates when cultured in equivalent fructose and glucose concentrations.

Figure 16:
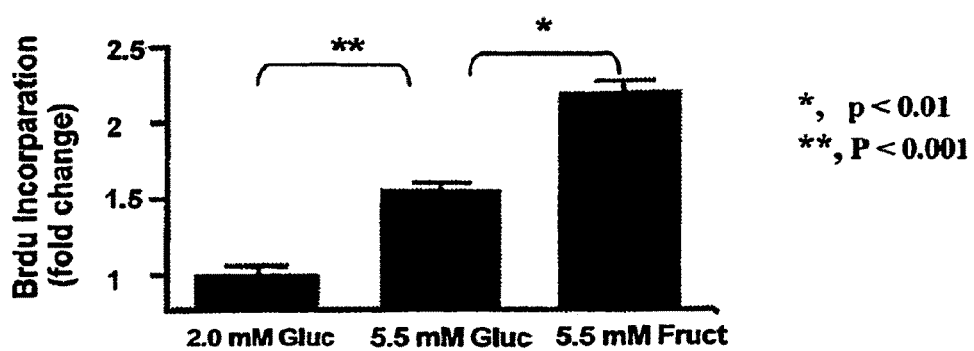
FIG. 16 depicts BRDU uptake following treatment with glucose or fructose in accordance with an embodiment of the present invention. PANC-1 cells were pre-incubated in 2 mM glucose prior to treatment with 5.5 mM glucose or fructose for 72 h. BRDU (0.01 mg/ml) was added to the medium at 48 h, and BRDU-uptake quantified at 72 h.

As a further measure of PANC-1 proliferative rates, the inventors compared bromodeoxyuridine (BRDU) uptake following PANC-1 cell treatment as before with 2 mM, and 5.5 mM glucose, or 5.5 mM fructose for 72 h. In the final 12 h, 10 µM BRDU was added to the glucose-, and fructose-treated cells, after which BRDU-positive cells were counted. As depicted in FIG. 16, in agreement with the other measures of pancreatic cancer cell proliferation, some increase in BRDU uptake was noted in the 5.5 mM glucose-treated pancreatic cancer cells in comparison to 2 mM glucose-treated cells. However, significantly higher BRDU-uptake (~75% higher than with 5.5 mM glucose) was noted in the PANC-1 cells which had been treated with 5.5 mM fructose in comparison to cells treated with 5.5 mM glucose, confirming that fructose leads to higher pancreatic cancer cell proliferation than equivalent glucose concentrations. A further question the inventors sought to address was would the fructose-induced pancreatic cancer proliferative rates be maintained if the PANC-1 cells were also exposed to, and able to utilize their customary culture glucose concentrations. Therefore, the inventors cultured PANC-1 cells for 72 h in a range of glucose concentrations (0-15 mM) admixed with a range of fructose concentrations (0-15 mM).

Figure 17:
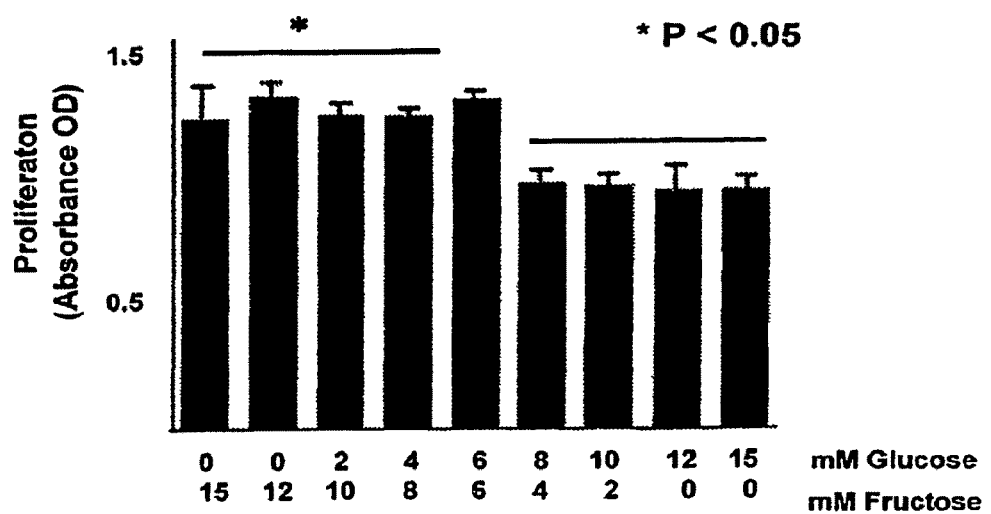
FIG. 17 depicts cell proliferation regardless of co-existent glucose concentration in accordance with an embodiment of the present invention. PANC-1 cells were pre-incubated in 2 mM glucose prior to treatment with a range of concentrations (0-15 mM) mixed with a range of fructose concentrations (0-15 mM) for 72 h. PANC-1 cell proliferative rates were then measured using the MTS assay (absorbance in arbitrary units).
Figure 18:
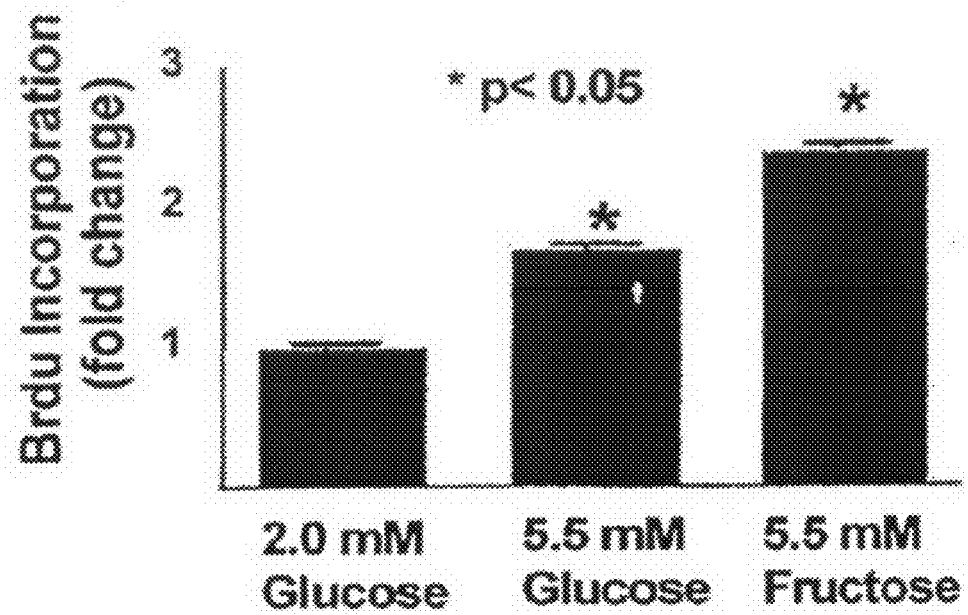
FIG. 18 depicts BRDU incorporation by pancreatic cells in accordance with an embodiment of the present invention. Freshly resected pancreatic cancers were mechanically and enzymatically dispersed, and cells were pre-incubated in 2 mM glucose prior to treatment with 5.5 mM glucose or fructose for 72 h. BRDU (10 μM) was added to the medium at 48 h, and BRDU-uptake quantified at 72 h.

As depicted in FIG. 17, once the PANC-1 cells were exposed to fructose concentrations of 6 mM and above, an increase in cell proliferation was noted, regardless of the co-existent glucose concentration. This suggested to the inventors that the pancreatic cancer cells were in some way able to distinguish glucose and fructose, and utilize the latter sugar in a different manner to lead to higher proliferative rates. Based on this series of experiments, the inventors concluded that fructose induced greater in vitro pancreatic cancer proliferative rates in comparison to equivalent, and even significantly higher glucose concentrations. As immortalized cell-lines, such as PANC-1 pancreatic cancer cells, can become dedifferentiated after repeated passages, and in order to translate these findings in the PANC-1 cells to patients with pancreatic cancer, the inventors also examined proliferative rates in primary cultures of fresh surgically resected pancreatic cancers, following incubation in 2 mM, and 5.5 mM glucose or 5.5 mM fructose. Briefly, after mechanical and enzymatic (trypsin and DNAse) disaggregation, aliquots of tumor cells were seeded in 6-well plates, and incubated in standard DMEM media with 10% fetal bovine serum, and 2 mM glucose, 5.5 mM glucose, or 5.5 mM fructose for 72 h. As before in the PANC-1 experiments, BRDU (10 μM) was added in the final 12 h of incubation in the sugars, following which BRDU-uptake was quantified. All 5 primary pancreatic cancers have exhibited higher proliferative rates in 5.5 mM fructose compared to 5.5 mM glucose, as illustrated in a representative tumor in FIG. 18.

Figure 19:
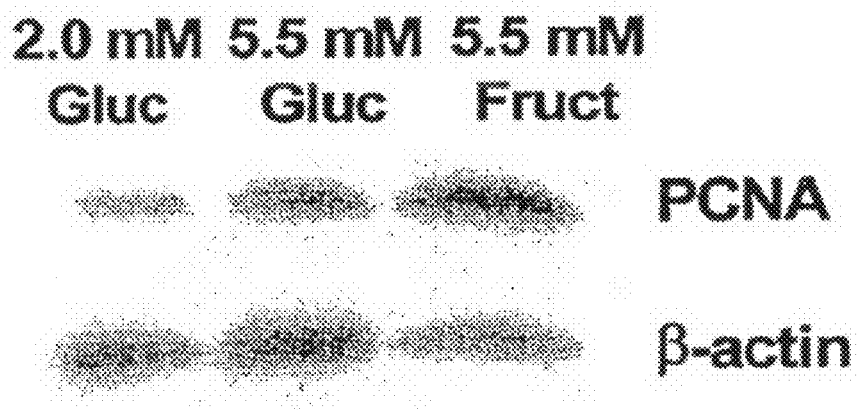
FIG. 19 depicts PCNA expression in accordance with an embodiment of the present invention. PANC-1 cells were plated in 2 mM, and 5.5 mM glucose, or 5.5 mM fructose for 48 h, after which proliferating cell nuclear antigen (PCNA) levels were measured by Western blot analysis.

Additionally, protein extracts were harvested in RIPA buffer from the PANC-1 cells following 2 mM, 5.5 mM glucose-, and fructose-treatment for 48 h, analyzed by Western blot, and immunoblotted using a specific monoclonal antibody to proliferating cell nuclear antigen (PCNA). As depicted in FIG. 19, some increased PCNA expression was observed in the PANC-1 cells following incubation in 5.5 mM glucose, compared to 2 mM glucose, in keeping with increased cell proliferation as the inventors had demonstrated with BRDU-uptake, and MTS assays. However, highest PCNA levels were observed in protein extracts derived from PANC-1 cells treated with 5.5 mM fructose, compared to 5.5 or 2 mM glucose, supporting the FACS and MTS proliferation assay findings, and confirming higher pancreatic cancer proliferative rates in equimolar fructose versus glucose.

Example 16

Figure 20:
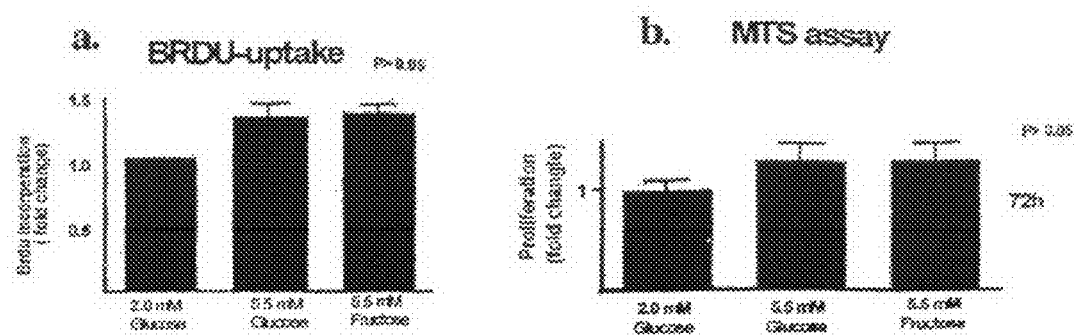
FIG. 20 depicts a degree of increased proliferation of normal pancreatic cells in accordance with an embodiment of the present invention. Freshly resected normal pancreas tissues were mechanically and enzymatically dispersed, and cells were pre-incubated in 2 mM glucose prior to treatment with 5.5 mM glucose or fructose for 72 h. BRDU (10 μM) was added to the medium at 60 h, and BRDU-uptake quantified at 72 h.

Normal Pancreatic Cells do not Exhibit Increased Proliferative Rates following Fructose-Treatment In the course of obtaining fresh surgically resected pancreatic cancer tissue, the inventors also obtained some peripherally adjacent "normal" pancreatic tissue and normal tissue from a patient undergoing pancreas resection for complications of chronic pancreatitis. The inventors studied 5 of these "normal" pancreas tissues, and although caveats may exist given that they were derived from pancreases which were involved with another disease entity, the inventors believe they offer a useful comparator for the tumors. Similar to the pancreatic cancers, normal pancreatic tissue was mechanically and enzymatically dispersed, and cells seeded into 6-well plates containing 2 mM glucose, 5.5 mM glucose, or 5.5 mM fructose for 72 h. As before, BRDU (100M) was added, after which BRDU-uptake was quantified. In parallel experiments, when sufficient normal pancreatic issue was available, proliferative rates following 72 h incubation in the sugars were also measured using the MTS proliferation assay. As depicted in FIGS. 20A and B, derived from two distinct representative normal pancreas tissues, the normal pancreas cells did demonstrate some increase in proliferation (measured by both BRDU-uptake (FIG. 20A) or MTS assay (FIG. 20B)) following incubation in 5.5 mM glucose, and 5.5 mM fructose, in comparison to proliferative rates seen in 2 mM glucose. However, contrary to what the inventors had observed in the PANC-1 cells and primary pancreatic cancer cells, proliferative rates did not differ significantly between normal pancreas cells incubated in 5.5 mM glucose or 5.5 mM fructose. These studies in normal pancreatic cells raise the intriguing possibility that the differential proliferative response to fructose versus glucose is restricted to transformed pancreatic cancer cells, and has important implications for therapeutic applications described herein.

Example 17

Pancreatic Cancer Cells Express Fructokinase-1, and Fructose-1-P Aldolase mRNA

Figure 21:
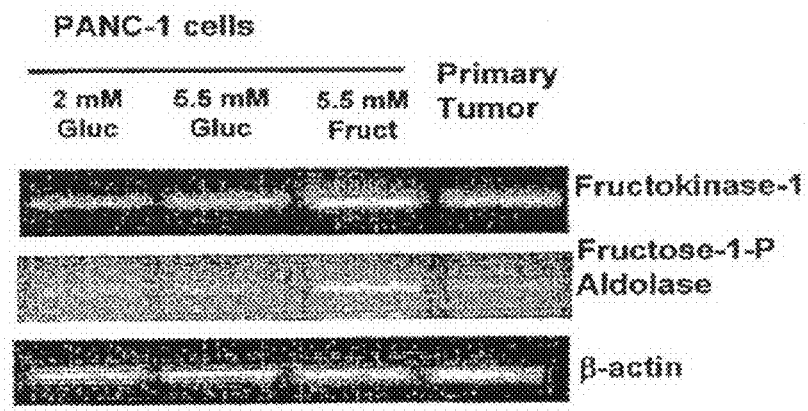
FIG. 21 depicts fructokinase-1 and fructose 1-P-adolase mRNA expression in PANC-1 cells in accordance with an embodiment of the present invention. RT-PCR fructokinase-1 (FK-1), and fructose 1-P-aldolase (FPA) mRNA expression in PANC-1 cells, and a human pancreatic cancer following 2 mM, or 5.5 mM glucose-, or 5.5 mM fructose-treatment.

Firstly, the inventors believed that pancreatic cancer cells may express fructokinase-1 and fructose-1-P aldolase, enzymes that would enable them to metabolize fructose to fructose-1-phosphate, allowing fructose to enter the TCA cycle downstream of the negative regulatory feedback of phosphofructokinase. To examine this, the inventors used RT-PCR analysis and specific primer pairs to examine fructokinase-1 (FK-1) and fructose-1-P aldolase (FPA) mRNA levels in glucose- or fructose-treated PANC-1 cells, and in surgically resected human pancreatic cancers. As depicted in FIG. 21, both PANC-1 cells, and the primary pancreatic cancers (representative tumor in lane 4) cultured in 2 mM, and 5.5 mM glucose, and 5.5 mM fructose did express FK-1, and FPA mRNA, enzymes that would potentially enable them to metabolize fructose to dihydroxyacetone phosphate, thereby bypassing key rate limiting steps to which glucose is subjected, to generate higher ATP levels for proliferation.

Example 18

Fructose-Treatment Increase Pancreatic Cancer GLUT-5 Expression

Figure 22:
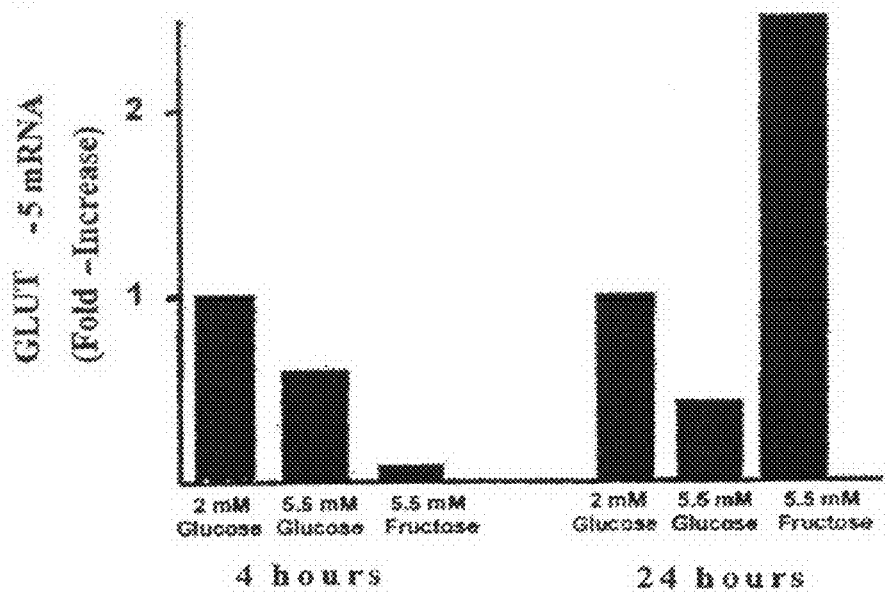
FIG. 22 depicts GLUT-2 mRNA levels in pancreatic cancer cells in accordance with an embodiment of the present invention. Quantitative real-time RT-PCR was used to measure GLUT-5 mRNA levels in pancreatic cancer cells (PANC-1), following culture in 2 mM glucose, 5.5 mM glucose, or 5.5 mM fructose for 4 h and 24 h.

A family of facilitative glucose/fructose transporter (GLUT) proteins regulate cellular sugar uptake, and previous studies have demonstrated increased cancer GLUT expression, including the fructose-selective GLUT-5 (Zamora-Leon S P, Dolde D W, Concha I I, Rivas C I, Delgado-Lopez F, Baselga J, Nualart F, Carlos-Vera J. Expression of the fructose transporter GLUT5 in human breast cancer. Proc Natl Acad Sci 93: 1847-52, 1996; Macheda M L, Rogers S, and Best J D. Molecular and cellular regulation of glucose transporter (GLUT) proteins in cancer. J Cellular Physiol 202: 654-662, 2005; Smith T A D. Facilitative glucose transporter expression in human cancer tissue. Brit J Biomed Sci 56(4): 285-292, 1999; Rogers S, Docherty S E, Slavin J L, Henderson and Best J D. Differential expression of GLUT12 in breast cancer and normal breast tissue. Cancer Letters 193(2): 225-233, 2003). Therefore, the inventors believed that if pancreatic cancer cells exhibited increased GLUT expression, this may increase carbohydrate (fructose) substrate availability, to mediate increased pancreatic cancer proliferation. Real-time RT-PCR was used to measure GLUT-5 mRNA expression following 2 mM, and 5.5 mM glucose-, and 5.5 mM fructose-treatment for 4 h, and 24 h respectively. GLUT-5 mRNA was expressed as the fold-change relative to GLUT-5 mRNA levels in 2 mM glucose-treated cells. As depicted in FIG. 22, at 4 h, GLUT-5 mRNA levels were low in both the 5.5 mM glucose-, and fructose-treated PANC-1 cells. In contrast, at 24 h, a dramatic increase in GLUT-5 mRNA levels following 5.5 mM fructose-treatment resulted, in comparison to GLUT-5 mRNA levels in 2 mM (1.5 fold higher) or 5.5 mM (1.75 fold higher) glucose-treated cells. This agrees with other studies which have reported fructose-induced GLUT-5 mRNA expression in colon cancer (74). Based on this finding, which requires confirmation in additional pancreatic cancer cell-lines, in addition to demonstration of GLUT-5 protein expression, the inventors have focused one of in vitro subaims to characterize the role of the fructose-selective GLUTs (GLUT-2, GLUT-5, and GLUT-7), particularly GLUT-5, in fructose-mediated pancreatic cancer proliferation.

Example 19

Fructose-Treatment Activates Pancreatic Cancer MAPK Signaling

Figure 23:
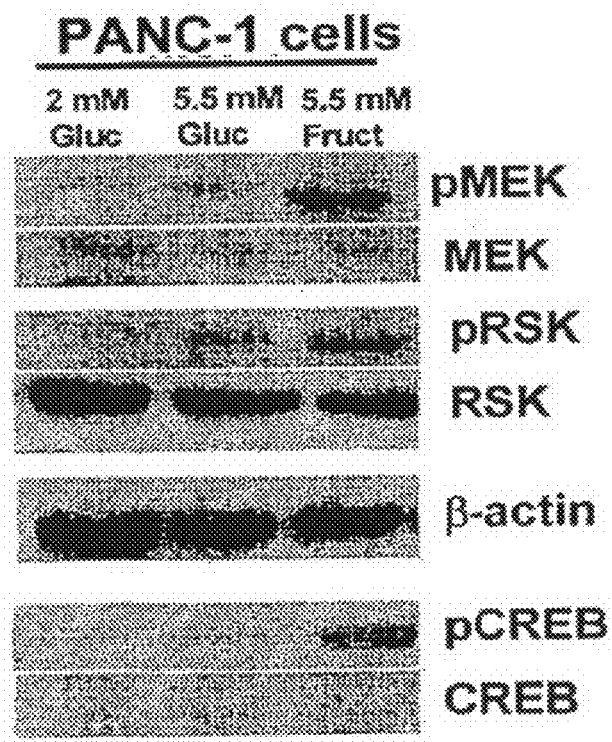
FIG. 23 depicts Western blot analysis examining MAPK pathway expression in accordance with an embodiment of the present invention. PANC-1 pancreatic cancer cells were incubated in 2 mM glucose, 5.5 mM glucose or 5.5 mM fructose for 48 hours, after which Western blot analysis on total protein lysates was employed to examine phosphorylated MEK (pMEK), pRSK, and pCREB, and corresponding total MEK, RSK, and CREB levels.

Several signal transduction pathways may be involved in fructose-mediated pancreatic cancer growth but given the importance of the MAPK pathway in proliferation, the inventors believed that MAPK was involved. In the MAPK pathway, MEK mediated phosphorylation of the p44/42 MAP kinase (ERK) is the first step in this cascade, which results in phosphorylation of p90$^{Rsk}$, leading to transcriptional activation of CREB, and AP1, activating gene transcription and promoting cellular growth. The inventors employed Western blot analysis to examine MAPK pathway expression in pancreatic cancer cells incubated in 2 mM glucose, 5.5 mM glucose, and 5.5 mM fructose for 48 hours. Levels of the active phosphorylated proteins, pERK, pRSK, and pMEK were normalized to total ERK, RSK, and MEK levels respectively, and compared between the fructose-, and glucose-treated PANC-1 cells. As depicted in FIG. 23, some phosphorylated-ERK, -RSK, and -MEK expression was observed in the PANC-1 cells incubated overnight in 2 mM glucose, and following 48 h incubation in 5.5 mM glucose, an increase in pERK, pRSK, and pMEK levels was observed. However, highest pERK, pRSK, and pMEK expression was demonstrated in PANC-1 cells incubated in 5.5 mM fructose, underpinning the role of the MAPK pathway in fructose-mediated pancreatic cancer cell proliferation.

Figure 24:
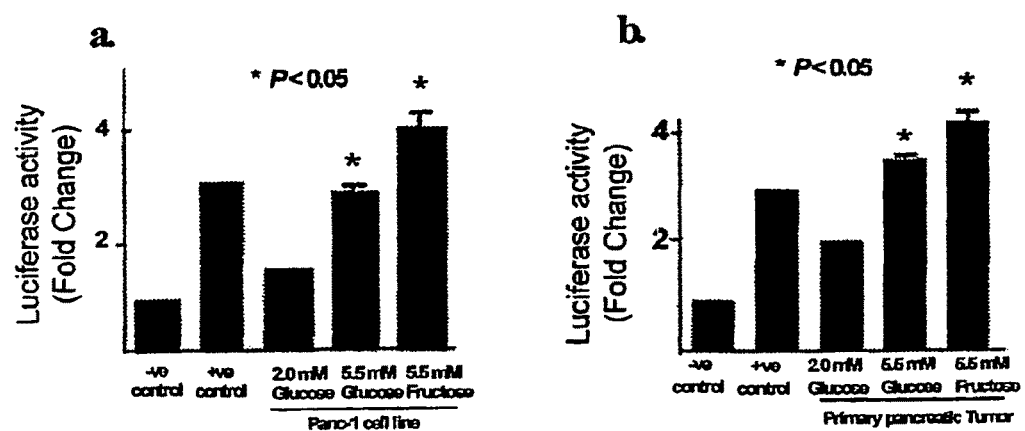
FIG. 24 depicts luciferase activity of PANC-1 cells and primary culture of surgically resected pancreatic tumor cells in accordance with an embodiment of the present invention.

In separate experiments PANC-1 cells, and primary cultures of surgically resected pancreatic tumors were incubated in 2 mM glucose, or 5.5 mM glucose or 5.5 mM fructose for 48 h, after which nuclear extracts were incubated with a biotinylated AP-1 probe in binding buffer. AP-1/AP1 probe complexes were next conjugated to a streptavidin-coated assay plate and detected using an AP-1 specific antibody, followed by binding of a horseradish-peroxidase conjugated secondary antibody, and detection by a colorimetric reagent. As depicted in FIG. 24a, low level background luciferase activity was demonstrated in vehicle-treated cells (negative control), and high-level luciferase activity was noted in the positive control, confirming the integrity of the assay.

Following incubation of the PANC-1 cells in 5.5 mM glucose, an approximate 2-fold increase in luciferase activity was noted in comparison to 2 mM glucose. Highest AP-1 luciferase reporter activity was observed in the PANC-1 cells that had been incubated in 5.5 mM fructose, which was approximately 40% higher than luciferase levels measured in the PANC-1 cells which had been incubated in 5.5 mM glucose, further demonstrating the importance of MAPK-signalling in fructose-mediated pancreatic cancer effects. In a primary culture of a pancreatic tumor, prepared as previously described (FIG. 24b), a 2.1-fold increase in AP-1 activation was observed in 5.5 mM fructose-treated cells, versus a 1.8 fold increase in 5.5 mM glucose-treated cells, compared to cells treated with 2 mM glucose. These results provide insight into the mechanism(s) of fructose-induced pancreatic cancer proliferation, and underscore the role of the MAPK pathway.

Example 20

Pancreatic Cancer Fructose Metabolism Differs Significantly from Glucose

Metabolism comprises anabolic (converting small molecules into big ones) and catabolic processes (converting food into useful energy), predicts the functional state of a cell, and analyzes the levels of the end products (metabolites) of anabolism and catabolism. Metabolic profiling using stable isotope tracer technology ([1,2-$^{13}$C] sugars) allows the measurement of the changing pattern of distribution of $^{13}$C carbons from [1,2-$^{13}$C] glucose in intracellular metabolic intermediates, and provides a simultaneous measure of carbon flow toward the pentose cycle, glycolysis, direct glucose oxidation, tricarboxylic acid (TCA) cycle and fatty acid synthesis (76,77). It also reveals specific flux changes in lactate, glutamate, nucleic acid ribose, palmitate and $CO_2$, and is a useful complement to the understanding of diseases, including cancer. The inventors employed [1,2-$^{13}C_2$] glucose, or [1,2-$^{13}C_2$] fructose stable isotope-based dynamic metabolic profiling (SiDMAP, Los Angeles, US) to track and quantify changes in glucose, and fructose carbon re-distribution among major metabolic pathways in pancreatic cancer cells (Lee W N, Boros L G, Puigjaner J, Bassilian S, Lim S, Cascante M. Mass istopomer study of transketolase-transaldolase pathways of the pentose cycle with [1,2-$^{13}C_2$]glucose. Am J Physiol 274:E843-51, 1998; Lee W N, Byerley L O, Bassilian S, Ajie H O, Clark I, Edmond J. Isotopomer study of lipogenesis in human hepatoma cells in culture: contribution of carbon and hydrogen atoms from glucose. Anal Biochem 226: 100-112). The principles of this methodology are outlined below in a series of schematics (FIGS. 25-27) illustrating how this technique tracked carbohydrate metabolism and the data generated. Essentially, there are three main ultimate metabolic fates for carbohydrates such as glucose or fructose. Firstly, as depicted in FIG. 25, once glucose, and/or fructose are taken into the cell via the GLUT transporters, they can enter glycolysis (common entry point being fructose 1,6 bisphosphate) to generate energy (ATP), and lactate.

Secondly, as depicted in FIG. 26, sugars can enter the tricarboxylic acid cycle (TCA) to result in fatty acid synthesis via Acyl-Coa, which in turn can be metabolized for energy (ATP) generation, and $CO_2$ release. Thirdly, as depicted in FIG. 27, carbohydrates can be utilized for nucleic acid synthesis via the enzyme transketolase in the pentose phosphate shunt. For the metabolic studies, 75% confluent cultures of PANC-1 cells ($3\times10^6$) were incubated for 24, and 72 h in 2 mM-, or 5.5 mM-[1,2-$^{13}C_2$] D-glucose-, or 5.5 mM [1,2-$^{13}C_2$] D-fructose (>99% purity, and 99% isotope enrichment for each carbon position) (Cambridge Isotope Labs, Massachusetts) -containing media (half unlabeled glucose/fructose, half labeled with the $^{13}$C tracer) in T75 culture flasks. These time points were chosen for the experiments, as previous studies have demonstrated that carbohydrate metabolism is most active within this time period. Where possible, these studies were also performed in primary pancreatic tumor, and normal pancreas cultures. After treatment, culture medium was collected, cells were washed twice in PBS, after which cell pellets were harvested, and mass spectral data were then obtained on a HP5973 mass selective detector connected to an HP6890 gas chromatograph. An HP-5 capillary column was used for the glucose, ribose and lactate analyses.

Example 21

Pancreatic Cancer Fructose Metabolism Differs Significantly from Glucose

As depicted in FIGS. 28 through 32, the metabolism of fructose and glucose in the pancreatic cancer cells differs significantly. Similar results were obtained for both the 24 h, and 72 h timepoints, and therefore, only the 72 h timepoint is depicted. Firstly, the contribution of glucose and fructose to glycolysis are discussed. Lactate is the main three-carbon product of glycolysis and it is readily secreted into the cell culture medium, therefore, it can be utilized for measurement of label incorporation into the three-carbon metabolite pool. Following glucose- or fructose treatment, lactate from the pancreatic cancer cell culture media (0.2 ml) was extracted by ethylene chloride after acidification with HCl, and then derivatized to its propylamine-heptafluorobutyrate ester form and the m/z 328 (carbons 1-3 of lactate) (chemical ionization, CI) were monitored for the detection of m1 (recycled lactate through the PC) and m2 (lactate produced by the Embden-Meyerhof-Parnas pathway) for the estimation of pentose cycle activity (Lee W N, Boros L G, Puigjaner J, Bassilian S, Lim S, Cascante M. Mass istopomer study of transketolase-transaldolase pathways of the pentose cycle with [1,2-13C2] glucose. Am J Physiol 274:E843-51, 1998). The m1/m2 ratios in lactate produced and released by the PANC-1 pancreatic adenocarcinoma cells were recorded in order to determine pentose cycle activity versus anaerobic glycolysis in response to glucose or fructose-treatment. As illustrated in FIG. 28, a large proportion of the $^{13}$C-labeled glucose entered glycolysis, and was metabolized to generate lactate (FIG. 28a), and $CO_2$ (FIG. 28b). In contrast, a comparatively small fraction of $^{13}$C-labeled fructose was metabolized to generate lactate and $CO_2$, resulting in a 34 fold lower lactate and $CO_2$ production for fructose in comparison to glucose. Secondly, the inventors examined fatty acid synthesis following glucose, and fructose-treatment. The incorporation of $^{13}$C from [1,2-$^{13}$C] glucose or fructose gives key information about the fraction of de novo lipogenesis in tumor cells and about glucose or fructose carbon contribution to acetyl-CoA for fatty acid synthesis. After glucose- or fructose-treatment of the pancreatic cancer cells, palmitate, stearate, cholesterol and oleate were extracted after saponification of cell pellets in 30% KOH and 100% ethanol using petroleum ether. Fatty acids were converted to their methylated derivative using 0.5N methanolic-HCl, and palmitate, stearate and oleate were monitored at m/z 270, m/z 298 and m/z 264, respectively, with the enrichment of 13C labeled acetyl units to reflect synthesis, elongation and desaturation of the new lipid fraction as determined by mass isotopomer distribution analysis (MIDA) of different isotopomers (Lee W N, Byerley L O, Bassilian S, Ajie H O, Clark I, Edmond J. Isotopomer study of lipogenesis in human hepatoma cells in culture: contribution of carbon and hydrogen atoms from glucose. Anal Biochem 226: 100-112; Lee W N, Lim S, Bassilian S, Bergner E A, Edmond J Fatty acid cycling in human hepatoma cells and the effects of trogiitazone. J Biol Chem 273: 20929-20934 1994). As demonstrated in FIG. 29, a significant proportion of glucose metabolism contributed to fatty acid synthesis (FAS) as evidenced by the high levels of glucose-derived $^{13}$C-labeled palmitate (FIG. 29a), stearate (FIG. 29b), and acetyl CoA (FIG. 29c), but comparatively less of the $^{13}$C-labeled fructose was metabolized for FAS generating palmitate (FIG. 29a), stearate (FIG. 29b), or acetyl-CoA/(FIG. 29c).

Ribose and deoxyribose synthesis, the building blocks of nucleotides, following glucose, and fructose-treatment were also compared. $^{13}$C incorporation from glucose or fructose into RNA ribose or DNA deoxyribose indicates changes in nucleic acid synthesis rates through the respective branches of the pentose cycle. Following the [1,2-$^{13}$C$_2$]D-glucose-, or [1, 2-$^{13}$C$_2$]D-fructose-treatments, RNA ribose was isolated by acid hydrolysis of cellular RNA after Trizol purification of cell extracts. Total RNA was quantified by spectrophotometric determination, in triplicate cultures. Ribose was then derivatized to its aldonitrile acetate form using hydroxylamine in pyridine with acetic anhydride (Supelco, Bellefonte, Pa.) before mass spectral analyses. The ion cluster was monitored around the m/z 256 (carbons 1-5 of ribose) (chemical ionization, CI) and m/z 217 (carbons 3-5 of ribose) and m/z 242 (carbons 1-4 of ribose) (electron impact ionization, EI) to determine molar enrichment and the positional distribution of $^{13}$C in ribose. Ribose molecules labeled with a single $^{13}$C atom on the first carbon position (ml) recovered from RNA were used to gauge the ribose fraction produced by direct oxidation of glucose or fructose through the G6PD pathway. Ribose molecules labeled with $^{13}$C on the first two carbon positions (m2) were used to measure the fraction produced by transketolase. Doubly labeled ribose molecules (m2 and m4) on the fourth and fifth carbon positions were used to measure molar fraction produced by triose phosphate isomerase and transketolase. In contrast to the relatively lower contribution of 5.5 mM fructose to glycolysis, and to fatty acid synthesis in comparison to glucose, as depicted in FIGS. 28, and 29, the metabolic studies demonstrated that $^{13}$C-labeled 5.5 mM fructose was preferentially metabolized in the PANC-1 pancreatic cancer cells via the pentose phosphate shunt to a greater extent than glucose. As noted above, the pentose phosphate shunt comprises two pathways; the oxidative pathway, which is regulated by glucose-6-phosphate dehydrogenase (G6PDH), which shuttles 5-carbon sugars back to the glycolytic pathway, and the non-oxidative pathway, which is regulated by the enzyme transketolase (TKK), which drives nucleic acid synthesis by generation of xylulose-5-phosphate from fructose-6-phosphate, and glyceraldehyde-3-phosphate. Characterization of the individual contribution of each sugar to the oxidative (G6PDH), and non-oxidative (TKK) pathways of the pentose phosphate shunt revealed that whereas 5.5 mM glucose was metabolized primarily via the oxidative component of the pentose phosphate shunt (FIG. 30, first set of bars; glucose), 5.5 mM fructose was preferentially metabolized by TKK (FIG. 30, second set of bars; fructose) contributing significantly to nucleic acid synthesis compared to 5.5 mM glucose.

In separate studies, the inventors treated primary cultures of 4 pancreatic adenocarcinomas, and 3 normal pancreas tissues with the [1,2-$^{13}$C$_2$]D-glucose-, or -fructose-tracers as before for 72 h, and carried out metabolic studies. A representative experiment is depicted in FIG. 31, and demonstrates that while normal pancreas tissue (left panel) effectively oxidizes both 5.5 mM glucose, and fructose to generate $CO_2$, the utilization of fructose and glucose for oxidation in the pancreatic cancer (right panel) is remarkably different, with significantly higher glucose oxidation than fructose. In regard to the BRDU-uptake studies in normal pancreas tissues, these metabolic results also suggest the differential utilization of fructose versus glucose may be restricted to transformed pancreatic cells.

These fascinating metabolic results demonstrated for the first time that metabolism of fructose by pancreatic cancer cells was strikingly different to that of glucose. Although both sugars were utilized to some extent in glycolysis, fatty acid, and nucleic acid synthesis, there are differences in the metabolism of glucose, and fructose, at least at these concentrations, and times, by pancreatic cancer cells. Whereas a considerable proportion of administered glucose was metabolized via glycolysis, and fatty acid synthesis, fructose was in large part metabolized by the non-oxidative pentose phosphate shunt to synthesize nucleic acids. These results also indicated that the mechanism of fructose-mediated increased growth may be more complex and interesting. These results provided important insights into fructose-mediated increased pancreatic cancer cell proliferation, and proposed an important role for the enzyme transketolase.

Example 22

Pancreatic Cancer Cells Utilize Fructose for Purine Synthesis

Based on the metabolic studies which led the inventors to believe that fructose was metabolized in pancreatic cancer cells in large part to generate nucleic acids, the inventors devised a series of experiments to examine nucleic acid synthesis in the pancreatic cancer cells following either glucose or fructose-treatment. PANC-1 cells were incubated as before in 5.5 mM glucose or fructose for 24 h, following an ELISA-based fluorimetric assay (Amplex Red Uric acic/uricase assay kit, Invitrogen) was employed to measure uricase activity in conditioned medium derived from the pancreatic cancer cells (Shi Y, Evans J E, Rock K L. Molecular identification of a danger signal that alerts the immune system to dying cells Nature 425, 516-21, 2003). Uricase activity correlates highly with uric acid production, a purine by-product of nucleic acid synthesis. Briefly, in the assay, uricase catalyzes the conversion of uric acid to allantoin, hydrogen peroxide ($H_2O_2$), and carbon dioxide. The $H_2O_2$ then, in the presence of horseradish peroxidase, reacts stoichiometrically with Amplex Red reagent to generate the red-fluorescent oxidation product, resorufin. Fluoresence was measured in a fluorescence microplate reader using excitation at 530 nm and detection at 590 nm, and the assay can detect levels as low as 100 nM uric acid. As demonstrated in FIG. 32, uricase activity in conditioned medium harvested at 96, and 120 h from the fructose-treated PANC-1 cells were ~20%, and ~50% higher than levels measured in conditioned medium derived from the glucose-treated PANC-1 cells at the same timepoints, p<0.01. These results demonstrated increased pancreatic cancer cell uric acid production after fructose-treatment, and as uric acid is a by-product of purine metabolism, this observation further supported the notion that fructose was metabolized to a greater extent than glucose to generate nucleic acids.

Example 23

Fructose-treatment Increases Pancreatic Cancer Transketolase Expression and Activity As noted previously, the metabolic studies indicated that the enzyme transketolase (TKK) was important in the metabolism of fructose via the pentose phosphate pathway to increase nucleic acid synthesis. The inventors believe that fructose-treatment of pancreatic cancer cells led to an increase in TKK-driven nucleic acid synthesis, and thus fructose-treatment would result in an increase in either PANC-1 TKK expression and/or activity in comparison to equivalent glucose concentrations. Western blot analysis on protein lysates derived from fructose-, and glucose-treated PANC-1 cells were performed (5.5 mM fructose, and glucose for 24, and 48 h as per previous protocol) using a specific TKK antibody, and compared TKK expression in the fructose-, and glucose-treated PANC-1 cells. As depicted in FIG. 33, TKK expression at 24 h, and 48 h in protein lysates derived from 5.5 mM glucose-treated PANC-1 cells was increased in comparison to expression in 2 mM glucose-treated cells. However, highest TKK expression was observed after 5.5 mM fructose treatment at 24 h, and 48 h, and TKK levels were almost 2-fold higher in 5.5 mM fructose-treated, in comparison to 5.5 mM glucose-treated cells (p<0.01). To measure TKK activity, a validated method which calculates TKK enzyme activity from the catalysis of the oxidation of NADH was used (Berrone E, Beltramo E, Solimine C, Ape A U, Porta M. Regulation of intracellular glucose and polyol pathway by thiamine and benfotiamine in vascular cells cultured in high glucose. J Biol Chem. 7; 281:9307-13. 2006; Comin-Anduix B, Boros L G, Marin S, Boren J, Callol-Massot C, Centelles J J, Torres J L, Agell N, Bassilian S, Cascante M. Fermented wheat germ extract inhibits glycolysis/pentose cycle enzymes and induces apoptosis through poly(ADP-ribose) polymerase activation in Jurkat T-cell leukemia tumor cells. J Biol Chem. 277:46408-14. 2002; De La Haba G, Leder I G, and Racker E. J. Biol. Chem. 214, 409-426 1995). Briefly, following treatment with 2 mM glucose, 5.5 mM glucose, and 5.5 mM fructose as before, PANC-1 cells were lysed in Tris-based protein lysis buffer, sonicated, spun, and supernatants collected. 100 µl of the latter supernatant fractions were added to a mixture containing 15 mmol/L ribose 5-phosphate, 50 µmol/L NADH, 0.1 molar Tris-HCL, and 200 units/ml glycerol-3-phosphate dehydrogenase. After gentle mixing the absorbance of the mixture was measured at 10 min intervals for 2 h at 340 nm. Transketolase activity was then derived from the difference in absorbance at 10, and 80 minutes, and expressed as nmol/min/million cells. As depicted in FIG. 34, TKK activity in protein lysates derived from 5.5 mM glucose-treated PANC-1 cells was not increased at 24 h, some increased TKK activity was observed following 48, and 72 h 5.5 mM glucose-treatment, but this TKK activity was not significantly different when compared to the 2 mM glucose-treated cells. In contrast, a striking increase in PANC-1 TKK activity was demonstrated at all three timepoints (24, 48, and 72 h) following 5.5 mM fructose-treatment, which was 2-fold higher at 24 h, maximally induced (3-fold higher) at 48 h, and 1.7-fold higher at 72 h, in comparison to the activity measured in the 5.5 mM glucose-treated PANC-1 cells. The transketolase (TKK) enzyme requires nicotinamide adenine dinucleotide (NAD) as a cofactor, a source of which is thiamine. The inventors believe that the addition of oxythiamine, a thiamine inhibitor may abrogate fructose-stimulated pancreatic cancer proliferation if TKK was a key in fructose-mediated pancreatic cancer cell growth. Thus, PANC-1 cells were incubated in 2, and 5.5 mM glucose, and 5.5 mM fructose as before for 72 h, with vehicle ($H_2O$)), and a range of oxythiamine concentrations (0.5 to 2 mM). Pancreatic cancer proliferation rates were then measured using the MTS assay (FIG. 35). Fructose-treatment (5.5 mM for 72 h) resulted in increased PANC-1 cell proliferative rates in comparison to those observed following 5.5 mM or 2 mM glucose-treatment. Addition of oxythiamine (0.5 mM) inhibited glucose-induced and fructose-induced PANC-1 proliferation, and supports the inventors' belief that the enzyme TKK is important for fructose-induced pancreatic cancer cell proliferation, addition of even low oxythiamine concentrations (0.5 mM) virtually abolished the fructose-mediated increase in pancreatic cancer cell proliferation, which also supports the inventors' belief that the enzyme transketolase is implicated in fructose-mediated increased pancreatic cancer growth.

Example 24

Fructose is Detectable in Human Serum

The normal circulating concentrations of fructose are unknown. To gain insight as to the potential relevance of the in vitro studies which demonstrate a pro-proliferative effect of fructose at concentrations above 4-5 mM, the inventors developed a sensitive, and specific ELISA-based assay to measure fructose levels in human sera, and tissue fluids. Briefly, aliquots (20 µl) of fructose standards (0.1, 0.5, 1, 2, 4, 6, and 8 mM) or unknown serum samples were mixed with 5 µl of a stock solution (125 U/ml) of the enzyme fructose dehydrogenase (Sigma) in 175 µl citric acid (0.05 M) phosphate (0.09 M) buffer (pH 4.5), and 20 µl of 3-(4,5-dimethylthiazol-2yl)-2,5-diphenyltetrazolium bromide (MTT), and phenazine methosulfate (Promega), incubated for 30 minutes, after which absorbance at 570 nM was recorded in a 96-well spectrophotometer. In additional studies, the inventors confirmed that the assay did not cross-react with glucose, ribose, mannose or xylose, and additional controls included fructose standard samples with added glucose, which confirmed that the assay could specifically detect the sugar fructose. As the first analysis, in accordance with institutional review board guidelines, the inventors obtained 32 serum samples randomly selected from anonymous inpatients at Cedars-Sinai Medical Center. The inventors also measured glucose in these same samples using standard glucose oxidase based methods. No details of medical condition were known for these patients, and as depicted in FIG. 36, in 24 of these 32 patients, serum fructose was greater than 5 mM. This intriguing result prompted the inventors to examine serum fructose levels in two other settings. Firstly, the inventors drew fasting blood samples from 6 patients with pancreatic cancer on the morning of surgical tumor resection. As depicted in FIG. 37a, 4 of these 6 patients had fasting serum fructose levels >5 mM, and two patients had serum fructose concentrations of ~12 mM. The significance of these findings in pancreatic cancer patients is at this point unclear, but the inventors believe that the fructose-mediated pro-proliferative effects seen in pancreatic cancer cells in vitro are of significance, given the circulating fructose concentrations the inventors measured. In a further experiment, 3 normal volunteers fasted for 10 hours, an indwelling cannula was placed in a forearm vein, baseline fasting blood drawn, after which they drank two cans of regular soda, which contained 76 g of sugars, almost exclusively high fructose corn syrup. This source of carbohydrate was chosen to approximate to equivalent glucose concentrations used in a standard 75 g glucose tolerance test, and to bear relevance that dietary sources of high content refined fructose may pose an independent risk factor for pancreatic cancer growth. As depicted in FIG. 37b, although mean fasting fructose level was 2.66 mM, within 15 minutes after drinking the two sodas, mean serum fructose levels rose to 16.5 mM, peaked at 30 minutes at 17 mM, and then fell gradually with a similar excursion to glucose, but serum levels remained higher than 5 mM for the 2 hour duration of blood sampling. Interestingly, although the source of sugar consumed contained an almost equivalent concentration of glucose, since high fructose corn syrup is 55% fructose, and 45% glucose, serum glucose concentrations did not exhibit the same increase across the carbohydrate tolerance test. These data may suggest that the capacity to counterbalance high glucose loads is better than that to counter high fructose loads.

Example 25

Characterize the Mechanism(s) of Fructose-Enhanced Pancreatic Cancer Proliferation In Vitro The inventors have performed the experiments in the primary tumor pancreatic cancer PANC-1 cell-line. As the inventors have also observed similar fructose-mediated effects on proliferation, MAPK-activation, and similar metabolic profiles in primary cultures of freshly resected pancreatic tumors, the inventors believe that the PANC-1 cell is a good model to study fructose-mediated effects in pancreatic cancer. Extending the studies, and examining proliferative rates and metabolic profiles in pancreatic cancer cell lines of various phenotypes may be done. These include MiaPaCa-2, another primary pancreatic cancer cell line, ASPC-1, and HPAF II, pancreatic cancer cell lines derived from ascitic fluid, and Capan1, and Hs766T, both derived from pancreatic cancer metastases. Additionally, the immortalized epithelial cell line derived from normal human pancreatic ducts HPDE6, which has previously been shown to maintain the phenotypic, and genotypic characteristics of normal human pancreatic ducts (85) may be used. For proliferation assays, the pancreatic cells (~10,000 per well) will be plated onto 96-well plates, in standard 10% FBS, high glucose (25 mM) DMEM medium. Cells are then incubated overnight in 10% FBS, low glucose (2 mM) DMEM, then switched to medium containing a range of glucose or fructose concentrations (2.5, 5, 7.5, 10, 15, 25, 50, 75, & 100 mM) for times 24, 48, 72 & 96 h. Proliferative rates are measured using CeliTiter 96 AQueous One Solution Cell Proliferation Assay (MTS), according to manufacturers instructions (Promega, Madison, Wis., USA). This rapid assay is ideal for these large numbers of samples and will quickly allow for the determination of optimal dose ranges and treatment times for subsequent experiments. Proliferative rates are also quantified by BRDU-uptake in the fructose-, and glucose-treated cells, as employed in the studies. Following the glucose-, and fructose-treatments, aliquots of the pancreatic cancer cells will also be prepared for FACS analysis to characterize cell-cycle profiles, determining the percentage of cells in the resting G0/G1 phase, and the proliferative DNA synthesis- (S-) phase. In separate studies, pancreatic cancer cells, primary pancreatic cancers, and normal pancreas cultures will be treated with the $[1,2-^{13}C_2]$D-glucose-, or -fructose-tracers as before for 72 h, and submitted for metabolic studies.

Example 26

Fructose-Enhanced Pancreatic Cancer Proliferation Involves MAPK Activation

Based on the results demonstrating higher pMEK, pRsk, and pCREB expression, and greater AP-1 luciferase activity in PANC-1 pancreatic cancer cells following fructose-treatment in comparison to glucose-treatment, the inventors believe that the MAPK pathway is a key mediator of fructose-induced pancreatic cancer growth. This hypothesis will be tested by examining pancreatic cancer MAPK signaling following glucose, and fructose-treatment in a variety of pancreatic cancer cells of different phenotypes, and normal pancreatic epithelial cells. Briefly, pancreatic cancer cells are seeded in 6-well plates, and treated with a range of glucose, and fructose concentrations (2, 5, 7.5, 10, 12.5, and 15 mM) for a range of times (6, 12, 24, 48, 72, and 96 h), after which aliquots of protein are harvested in RIPA buffer, and western blot analysis employed to measure activation of the MAPK pathway. Image analysis, with densitometric quantitation of immunoblots, is used to measure activation of the MAPK components. For example, the ratio of levels of phosphorylated CREB are corrected for total CREB levels, for each of the treatments, and times and then used to compare the responsivity of the MAPK pathway to the different sugars in the cell-lines of different phenotypic origins. While not wishing to be bound by any particular theory, the inventors believe that the pancreatic cancer cell-lines with more aggressive phenotypes, such as Capan1, and Hs766T, exhibits greater MAPK activation in response to fructose-treatment, in comparison to the primary pancreatic cancer cell lines such as PANC-1. Pharmacological and molecular approaches to regulate MAPK signaling, and examine the effects on proliferation of the pancreatic cancer cells are used. Firstly, the specific MAPK inhibitor, PD 98059 (10-7 to 10-5M), which is added to the pancreatic cancer cells in combination with the glucose-, and fructose-treatments is used. In a second approach, zinc-inducible plasmids encoding dominant negative (DN−) MAPK cDNA is employed to downregulate MAPK expression in the cell lines which exhibit comparatively high level MAPK expression following fructose-treatment.

Example 27

Preferential Fructose-Utilization for Nucleic Acid Synthesis is Due to GLUT-5-mediated Increased Substrate Availability One question that arises from the metabolic results is how fructose, a "substrate" leads to increased nucleic acid synthesis, activation of MAPK signal transduction, and ultimately increased pancreatic cancer cell proliferation. While not wishing to be bound by any particular theory; the inventors believe that the difference in structure of fructose (a ketone), and glucose (an aldehyde) plays a role. Analysis of the metabolic pathway of fructose reveals that fructose can readily be converted to fructose-6-phosphate by hexokinase, thereby allowing rapid entry into the pentose phosphate shunt to generate nucleic acids, whereas glucose must first be converted to glucose-6-phosphate, and then converted to fructose-6-phosphate by an isomerase. Increased fructose-mediated nucleic acid synthesis may be a consequence of the molecular structure of fructose, serving as a ketone donor. Thus, efforts to reduce cellular availability of fructose may result in reduced pancreatic cancer proliferative rates as well as the proliferative rates of other cancers. Both glucose and fructose gain entry to the cell via active transport assisted by a family of glucose uptake and transport proteins (GLUT 1-12). Three of the GLUT proteins (GLUT 2, 5 & 7) show specificity for fructose uptake, and GLUT-5 appears to be the predominant fructose-transport protein, as reported in several solid tumors. No studies have focused on pancreatic cancer. Real-time quantitative RT-PCR is used to measure expression of all twelve GLUT mRNA's (GLUT 1-12) following treatment with a range of glucose, and fructose-concentrations (2, 5, 7.5, 10, 12.5, and 15 mM) for a range of times (6, 12, 24, 48, 72, and 96 h). As depicted in the data, FIG. 22, the inventors have already demonstrated that pancreatic cancer GLUT-5 mRNA expression is significantly increased following fructose-treatment, and the second hypothesis proposes that altered GLUT-5 expression facilitates increased pancreatic cancer fructose-uptake, thereby increasing availability of fructose substrate for pro-proliferative actions in the pancreatic cancer cells. Molecular approaches to overexpress (using Zn-regulatable GLUT-5 expressing plasmids) or silence GLUT-5 expression (using siRNA approaches) are used and then effects of these manipulations on fructose-, and glucose-mediated pancreatic cancer cell proliferation, transketolase action (expression and activity), and nucleic acid synthesis (determined by uricase activity, and RNA synthesis by metabolic studies using the $[1,2-^{13}C_2]$D-glucose-, or -fructose-tracers using the methods employed in the data) are examined. To knock-down GLUT-5 expression, the SureSilencing system (Superarray Bioscience Corp) which utilizes four distinct interfering RNA's to the target is used. These SiRNA's also include an EGFP-tag sequence so clones can be FACS fluorescence sorted. Other silencing systems known in the art may also be used. Single cell clones (e.g., 30-50) are expanded and GLUT-5 expression is examined in the pancreatic cancer cells by western blot, to generate stable pancreatic cancer GLUT-5 knockout cells. SiRNA approaches to silence other GLUT members that are induced by fructose, or Zn-inducible vectors to overexpress these other fructose-selective GLUT's in the pancreatic cancer cells are used. Effects on growth rates observed in the fructose-treated pancreatic cancer cells are also determined. Silenced or increased GLUT expression are confirmed by Western blot, and the effects of altered GLUT expression on pancreatic cancer cell growth rates across a range of fructose and glucose concentrations are examined. The non-fructose selective GLUT proteins GLUT-1, and GLUT-3 are employed as negative controls in the knock-out, and overexpression experiments.

Example 28

Fructose-Induced Pancreatic Cancer Proliferation Requires Transketolase

The inventors believe that transketolase is required for fructose-induced cancer proliferation as demonstrated by increased pancreatic cancer transketolase expression (FIG. 33) and activity (FIG. 34) following fructose-treatment, in comparison to glucose-treatment. Pharmacological and molecular approaches to modify transketolase expression and to examine effects of altered transketolase activity on fructose-mediated pancreatic cancer proliferative rates are used. The data demonstrates that comparatively low (0.5 mM) concentrations of the competitive thiamine inhibitor, oxythiamine, almost completely abrogate fructose-induced pancreatic cancer proliferative rates (FIG. 35). A broader range of oxythiamine concentrations (0.01, 0.005, 0.1, 0.25, and 0.5 mM) on fructose-, and glucose-induced pancreatic cancer proliferative rates in the pancreatic cancer cell lines of different phenotypes are used. SureSilencing system, utilizing 4 distinct interfering TKK RNA's to block transketolase expression is employed and FACS sorted single cell clones (e.g., 30-50) are expanded, and TKK expression is examined by western blot. Clones (a minimum of 5 in each category below) with a range of levels of TKK expression are selected (absent TKK, low TKK, moderate TKK, normal TKK levels), treated with 5.5 mM glucose, or 5.5 mM fructose as before, and proliferative rates, and metabolic profiles are compared between the TKK silenced and wild-type pancreatic cancer cells.

Example 29

Determine Effects of Refined Fructose Consumption on In Vivo Pancreatic Cancer Growth The effects of 10% and 20% added refined fructose and glucose on pancreatic cancer development are examined. These percentages are chosen as they are conservative but meaningful equivalent to current human refined carbohydrate intake. Therefore, refined glucose or fructose is administered to mice inoculated subcutaneously with PANC-1 pancreatic cancer cells. Effects of treatments on time to tumor development, and tumor multiplicity are examined.

Example 30

Pancreatic Cancer Xenograft Tumor Model in Nu/Nu Mice

Female athymic Nu/Nu mice are purchased from Jackson Laboratories. PANC-1 cells ($3 \times 10^6$) are inoculated subcutaneously on the flank of the mice, under isoflurane anesthesia, in accordance with institutional animal care and use guidelines. These animals reproducibly develop flank pancreatic tumors between 4-5 weeks. The mice receive a commercially purchased standard chow diet (Labdiet.com, certified rodent diet 5002), eat ~5 g per day, and receive a total daily intake of approximately 1700 Kcal, comprising 64.5% CHO, 11.8% fat, 23.5% protein, and 4.6% fiber. Mice also receive a fructose or glucose sugar solution containing 0.42 g or 0.84 g fructose or glucose (diluted in 100 ml) which equate to 10% or 20% added refined carbohydrate respectively or vehicle daily from age 3 months to 12 months. Developing tumors in the fructose-, glucose-, and vehicle-fed mice are measured twice a week with electronic calipers, and tumor volumes determined by multiplying the square of the width (w) by the length (l) and dividing by two (i.e., $(w^2 l)/2$). Individual animal weights, tumor size and tumor location will be recorded for each animal twice a week. Animals are euthanized when they develop tumors of 1000 mm$^3$ or more or at the end of the experiment, at the same time of day to limit temporal variations in glucose, insulin, and other parameters. Two hours before killing, the mice are injected intraperitoneally with bromodeoxyuridine (3 mg/mL) in phosphate-buffered saline, (100 µL/10 g body weight). The end of the experiment is defined as the time when all vehicle-treated mice have developed a tumor. At that time, all remaining mice (vehicle-, glucose-, and fructose-treated) are, tumors resected, and studied.

Example 31

Histology and Biomarker Analysis—Pancreatic Cancer

For histology, pancreatic tumors are fixed in formalin and paraffin-embedded. Tissue sections are processed for immunohistochemical staining for the proliferative markers, PCNA, and Ki-67 to compare tumor proliferative rates derived from the fructose-, and glucose-treated mice. Briefly, tissue sections are deparaffinized in xylene, rehydrated, endogenous peroxidase activity blocked, non-specific binding reduced with goat serum, after which sections are incubated with antibodies to PCNA or Ki-67 (MIB-1) (1:200). Washed sections are incubated with biotinylated goat anti-mouse antibody, incubated with the ABC kit (Vector labs), and 3-amino-9-ethylcarbazole to visualize the peroxidase complex. Levels of immunostaining are evaluated by visual assessment with a semiquantitative scoring system rating staining intensity (from 0 to 3). Staining for bromodeoxyuridine (BRDU) is performed with the DAKO Animal Research Kit system. Briefly, tissue sections are prepared, as above, and BRDU stained with a mouse anti-BRDU monoclonal antibody (DAKO), slides incubated with streptavidin-horseradish peroxidase, and visualized with diaminobenzidine chromagen. Counterstaining is performed with hematoxylin, sections are scored by counting the positive and negative cells in 10 high-powered fields in tissue samples from 4 mice in each group. Results are expressed as the mean percentage with 95% CI.

Example 32

Glucose, Insulin, IGF1, Lipid, and Inflammatory Cytokine Levels

Fructose-, glucose-, and vehicle-treated mice will be fasted for 24 h every 4 weeks, and blood will be collected by the tail clip method into chilled tubes for assay of glucose, insulin, lipid and inflammatory cytokine levels. Blood will also be collected at euthanasia. Plasma glucose concentrations will be determined using Glucotrend 2 (Roche Diagnostics); plasma insulin (Linco Res), and IGF-1 Phoenix Pharmaceuticals levels are measured using solid phase two site enzyme immunoassays; plasma triglyceride, free fatty acids, lactate, and phydroxybutyrate concentrations are analyzed using commercially available kits (Sigma Diagnostics). Serum inflammatory markers include C-reactive protein, IL-6 (R&D Systems), serum sialic acid, soluble intracellular and vascular adhesion molecules (sICAM-1, and sVCAM-1) (Bender MedSystems Inc), and amyloid A levels, and are assayed using commercially purchased ELISA based kits (R & D, Quantikine). All parameters are measured in triplicate in the pancreatic cancer cell innoculated mice, and means compared between the fructose-, and glucose-, and vehicle-fed animals, at the various timepoints using ANOVA with Bon-Ferroni post t-tests for multiple comparisons. Time curves are graphed to compare trends in fasting glucose, insulin, lipid, and triglyceride levels, and inflammatory markers across the dietary treatment.

While the description above refers to particular embodiments of the present invention, it should be readily apparent to people of ordinary skill in the art that a number of modifications may be made without departing from the spirit thereof. The accompanying claims are intended to cover such modifications as would fall within the true spirit and scope of the invention. The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

What is claimed is:

1. A method for diagnosing cancer in a mammal, comprising:

administering a detectable quantity of a radiolabeled fructose or deoxyfructose to the mammal; and imaging the mammal at least 180 minutes after administering the detectable quantity of the radiolabeled fructose or deoxyfructose to the mammal to detect a signal from the radiolabel from the fructose or deoxyfructose, wherein a presence of a higher accumulation of the signal in comparison to noncancerous tissue of the same type indicates a presence of cancer in the mammal, and the absence of a higher accumulation of the signal in comparison to noncancerous tissue of the same type indicates the absence of cancer in the mammal.

2. The method of claim 1, wherein the mammal has intolerance to glucose.

3. The method of claim 1, wherein the radiolabeled fructose or deoxyfructose is metabolized and/or utilized for nucleic acid synthesis.

4. The method of claim 1, wherein the radiolabel of the radiolabeled fructose or the radiolabeled deoxyfructose is a radioactive isotope of fluorine, iodine, gallium, technetium, indium or copper.

5. The method of claim 1, wherein the radiolabel of the radiolabeled fructose or the radiolabeled deoxyfructose is a radioactive isotope of fluorine.

6. The method of claim 1, wherein the radiolabel of the radiolabeled fructose or the radiolabeled deoxyfructose is on the first and/or the second carbon atom of the radiolabeled fructose or the radiolabeled deoxyfructose.

7. The method of claim 1, wherein the deoxyfructose is deoxyfluorofructose.

8. The method of claim 7, wherein the deoxyfluorofructose is 1-deoxy-1-fluoro-fructose.

9. The method of claim 7, wherein the deoxyfluorofructose is 1-deoxy-2-fluoro-fructose.

10. The method of claim 1, wherein imaging the mammal comprises imaging the mammal after at least 4 hours, at least 24 hours, at least 36 hours, or at least 48 hours after administering the detectable quantity of radiolabeled fructose or the radiolabeled deoxyfructose.

11. The method of claim 1, wherein imaging the mammal comprises imaging the mammal after the radiolabeled fructose or deoxyfructose is utilized by the cell for nucleic acid synthesis.

12. The method of claim 1, wherein imaging the mammal comprises using a technique selected from the group consisting of positron emission tomography (PET), computed tomography, magnetic resonance imaging, and combinations thereof.

13. A method for diagnosing cancer in a mammal, comprising:
administering a detectable quantity of a radioactive fructose or deoxyfructose to the mammal; and
imaging the mammal at least 180 minutes after administering the detectable quantity of the radioactive fructose or deoxyfructose to the mammal to detect a radioactive signal from the fructose or deoxyfructose,
wherein a presence of a higher accumulation of the signal in comparison to noncancerous tissue of the same type indicates the presence of cancer in the mammal, and the absence of a higher accumulation of the signal in comparison to noncancerous tissue of the same type indicates the absence of cancer in the mammal.

14. The method of claim 13, wherein the radioactive fructose or deoxyfructose is metabolized and/or utilized for nucleic acid synthesis.

15. The method of claim 13, wherein the radioactive fructose or deoxyfructose comprises a radioactive carbon isotope at the first and/or the second carbon atom.

16. The method of claim 13, wherein imaging the mammal comprises imaging the mammal after the radioactive fructose or deoxyfructose is utilized for nucleic acid synthesis.

17. The method of claim 13, wherein imaging the mammal comprises using a technique selected from the group consisting of positron emission tomography (PET), computed tomography, magnetic resonance imaging and combinations thereof.

18. The method of claim 14, wherein the radioactive fructose or deoxyfructose comprises a $^{13}C$ isotope.

19. A method for diagnosing cancer in a mammal, comprising:
administering a detectable quantity of radiolabeled 1-deoxy-1-fluoro-fructose; and
imaging the mammal at least 180 minutes after administering the detectable quantity of the radiolabeled 1-deoxy-1-fluoro-fructose to the mammal to detect a signal from the radiolabel from the 1-deoxy-1-fluoro-fructose,
wherein a presence of a higher accumulation of the signal in comparison to noncancerous tissue of the same type indicates a presence of cancer in the mammal, and the absence of a higher accumulation of the signal from the radiolabel or radioactive signal in comparison to noncancerous tissue of the same type indicates the absence of cancer in the mammal.

20. The method of claim 19, wherein imaging the mammal comprises imaging the mammal after at least 4 hours, at least 24 hours, at least 36 hours, or at least 48 hours after administering the detectable quantity of 1-deoxy-1-fluoro-fructose.

21. The method of claim 19, wherein imaging the mammal comprises imaging the mammal after the 1-deoxy-1-fluoro-fructose is utilized by the cell for nucleic acid synthesis.

22. The method of claim 19, wherein imaging the mammal comprises using a technique selected from the group consisting of positron emission tomography (PET), computed tomography, magnetic resonance imaging, and combinations thereof

23. The method of claim 19, wherein the 1-deoxy-1-fluoro-fructose is 1-deoxy-1-[$^{18}F$] fluoro-D-fructose.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: Primer

<400> SEQUENCE: 1
atcgtctgtg tagaccgtcc                                               20

<210> SEQ ID NO 2
<211> LENGTH: 20
<212> TYPE: DNA
<213> ORGANISM: Artificial
<220> FEATURE:
<223> OTHER INFORMATION: Primer

<400> SEQUENCE: 2
aagtgcttgg ccacatcttt                                               20

<210> SEQ ID NO 3
<211> LENGTH: 20
<212> TYPE: DNA
<213> ORGANISM: Artificial
<220> FEATURE:
<223> OTHER INFORMATION: Primer

<400> SEQUENCE: 3
aaaaggacct atccctccga                                               20

<210> SEQ ID NO 4
<211> LENGTH: 20
<212> TYPE: DNA
<213> ORGANISM: Artificial
<220> FEATURE:
<223> OTHER INFORMATION: Primer

<400> SEQUENCE: 4
tagacagcag ccaggacctt                                               20
```